US008030007B2

(12) United States Patent
El Shami et al.

(10) Patent No.: US 8,030,007 B2
(45) Date of Patent: Oct. 4, 2011

(54) METHOD FOR THE DETECTION OF ENDOMETRIOSIS USING AN ME-2 ANTIGEN

(75) Inventors: A. Said El Shami, Camarillo, CA (US);
Bruce Campbell, Calabasas, CA (US);
Dennis Sustarsic, Seal Beach, CA (US);
Niver Sahakian, Encino, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 13/040,130

(22) Filed: Mar. 3, 2011

(65) Prior Publication Data

US 2011/0201129 A1    Aug. 18, 2011

Related U.S. Application Data

(60) Continuation of application No. 11/593,975, filed on Nov. 6, 2006, now abandoned, which is a division of application No. 10/887,540, filed on Jul. 7, 2004, now abandoned.

(51) Int. Cl.
*G01N 33/53* (2006.01)
(52) U.S. Cl. ...... 435/7.1; 435/7.92; 435/7.93; 435/7.94; 435/7.95; 530/853; 530/868; 514/9.8
(58) Field of Classification Search .................. None
See application file for complete search history.

(56) References Cited

U.S. PATENT DOCUMENTS

| | | |
|---|---|---|
| 4,489,166 A | 12/1984 | Joshi |
| 5,618,680 A | 4/1997 | Miron et al. |
| 5,843,673 A | 12/1998 | Sharpe-Timms |
| 5,877,284 A | 3/1999 | Lyttle |
| 6,165,767 A | 12/2000 | Lal et al. |
| 6,294,662 B1 | 9/2001 | Tabibzadeh |
| 6,376,201 B2 | 4/2002 | Miron et al. |
| 6,387,629 B1 | 5/2002 | Schneider et al. |
| 6,525,187 B1 | 2/2003 | El Shami et al. |
| 6,531,277 B2 | 3/2003 | Timms |
| 6,540,980 B1 | 4/2003 | Blumenthal et al. |
| 6,645,725 B2 | 11/2003 | Yeaman |
| 6,777,182 B2 | 8/2004 | Baban et al. |
| 6,780,594 B2 | 8/2004 | Hess-Stumpp et al. |
| 7,049,069 B2 | 5/2006 | Chegini et al. |
| 7,122,322 B2 | 10/2006 | Timms |
| 2001/0044158 A1 | 11/2001 | Yeaman |
| 2002/0192647 A1 | 12/2002 | Smith |
| 2007/0184444 A1 | 8/2007 | Abbas et al. |
| 2007/0224201 A1 | 9/2007 | Wu et al. |

FOREIGN PATENT DOCUMENTS

| | | |
|---|---|---|
| DE | 100 48 633 A1 | 4/2002 |
| EP | 0 387 027 A2 | 12/1990 |
| EP | 1 130 123 A2 | 9/2001 |
| EP | 1 191 107 A3 | 3/2002 |
| WO | 92/16535 A1 | 10/1992 |
| WO | 94/28021 A1 | 12/1994 |
| WO | 97/35016 A1 | 9/1997 |
| WO | 99/04265 A2 | 1/1999 |
| WO | 99/49037 A2 | 9/1999 |
| WO | 99/63116 A2 | 12/1999 |
| WO | 00/43789 A1 | 7/2000 |
| WO | 00/63675 A1 | 10/2000 |
| WO | 00/75321 A2 | 12/2000 |
| WO | 01/32920 A2 | 5/2001 |
| WO | 02/068579 A2 | 9/2002 |
| WO | 2004/030615 A2 | 4/2004 |
| WO | 2004/087874 A2 | 10/2004 |

OTHER PUBLICATIONS

Ballinger, et al., "Identification of CHIP: a Novel Tetratricopeptide Repeat-Containing Protein That Interacts with Heat Shock Proteins and Negatively Regulates Chaperone Functions", Mol. Cell Biol., 19:4535-4545 (1999).
Brosens, et al., "Is laparoscopy the gold standard for the diagnosis of endometriosis?", Eur. J. Obstet. Gynecol. Repro. Biol., 88:117-119 (2000).
Brosens, et al., "Noninvasive diagnosis of endometriosis: the role of imaging and markers", Obstet. Gynecol. Clin. North Am., 30(1):95-114 (2003).
Canavan, et al., "Managing endometriosis: Strategies to minimize pain and damage", Postgrad. Med., 107(3):213-224 (2000).
Coxhead, et al., "Familial inheritance of endometriosis in a British population. A case control study", J. Obstet. Gyn., 13:42-44 (1993).
Galfre, et al., "Antibodies to major histocompatibility antigens produced by hybrid cell lines", Nature, 266:550-552 (1977).
Gosselin, et al., "Insights into the physiopathology of endometriosis—novel diagnostic and therapeutic approaches", Curr. Opin. Endo. & Metabol. Invest. Drugs, 1(1):31-43 (1999).
Husby, et al., "Diagnostic delay in women with pain and endometriosis", Acta Obstet. Gynecol Scand., 82:649-653 (2003).
Koninckx, "Is mild endometriosis a disease? Is mild endometriosis a condition occurring intermittently in all women?", Hum. Reprod., 9(12):2202-2211 (1994).
Mahnke, et al., "Vascular endothelial growth factor and interleukin-6 in peritoneal fluid of women with endometriosis". Fertil. Steril., 73(1): 166-170 (2000).
Matalliotakis, et al., "A Randomized Comparison of Danazol and Leuprolide Acetate Suppression of Serum-Soluble CD23 Levels in Endometriosis", Obstet. Gynecol., 95:810-813 (2000).
Mol, et al., "The performance of CA-125 measurement in the detection of endometriosis: a meta-analysis", Fertil. Steril., 70(6):1101-1108 (1998).

(Continued)

*Primary Examiner* — Michael Szperka
(74) *Attorney, Agent, or Firm* — Kevin Stein

(57) ABSTRACT

A method for diagnosing endometriosis in a human subject comprising the steps of detecting a test amount of an antibody that specifically binds to SEQ ID NO: 6 polypeptide or a truncated peptide comprising an epitope of SEQ ID NO: 6 in a sample from the subject; and comparing the test amount with a normal range of the antibody in a control sample from a subject who does not suffer from endometriosis, whereby a test amount above the normal range provides a positive indication in the diagnosis of endometriosis.

7 Claims, 30 Drawing Sheets

OTHER PUBLICATIONS

Oi, et al., "Immunoglobin-Producing Hybrid Cell Lines", in B.B. Mishell, et al. (eds), "Selected Methods in Cellular Immunology", W.H. Freeman, San Francisco, CA, pp. 351-372 (1980).

Pillai, et al., "Antibodies to Endometrial Transferrin and Alpha 2-Heremans Schmidt (HS) Glycoprotein in Patients with Endometriosis", Am. J. Reprod. Immunol., 35:483-494 (1996).

Pillai, et al., "Effects of Antibodies to Transferrin and Alpha 2-HS Glycoprotein on in Vitro Sperm Motion: Implications in Infertility Associated with Endometriosis", Am. J. Reprod. Immunol., 39:235-242 (1998).

Redwine., "Was Sampson wrong?", Fertil. Steril., 78(4):686-693 (2002).

Scanlan, et al., "Characterization Of Human Colon Cancer Antigens Recognized By Autologous Antibodies", Int. J. Cancer. 76:652-658 (1996).

Sharkey, et al., "Vascular Endothelial Growth Factor Expression in Human Endometrium is Regulated by Hypoxia", J. Clin. Endocrinol. Metab., 85(1):402-409 (2000).

Sharpe-Timms. et al., "Endometriotic Lesions Synthesize and Secrete a Haptoglobin-Like Protein", Biol. Reprod., 58:986-994 (1998).

Shulman, et al., "A better cell line for making hybridomas secreting specific antibodies", Nature, 276:269-270 (1978).

Thomas, et al., "Evidence that Endometriosis Behaves in a Malignant Manner", Gynecol. Obstet. Invest., 50(supp. 1) 2-10 (2000).

Van Voorhis, et al., "Autoantibodies and infertility: a review of the literature", J. Reprod. Immunol., 33:239-256 (1997).

Vigano, et al., "Endometrial Release of Soluble Intercellular Adhesion Molecule 1 and Endometriosis: Relationship to the Extent of the Disease". Obstet. Gynecol., 95(1):115-118 (2000).

Wolin, et al., "The Ro 60 kDa autoantigen comes into focus: Interpreting epitope mapping experiments on the basis of structure", Autoimmunity Reviews, 5:367-372 (2006).

Colman, "Effects of amino acid sequence changes on antibody-antigen interations", Research in Immunol., 145:33-36 (1994).

Harlow, et al., "Using Antibodies: A Laboratory Manual", Cold Spring Harbor Laboratory Press. Cold Spring Harbor, New York, pp. 75-76 (1999).

OM protein, protein search using sw model. Run May 31, 2006, 03:23-21. pp. 1-3.

Accession No. BC007545.1 (GI No. 14043118, first seen in NCBI May 15, 2001 4:50 pm).

Accession No. AF129086.1 (GI No. 4928063, first seen at NCBI Jun. 10, 1999 12:07 am).

Accession No. NM_005861.2 (GI No. 56181386, first seen at NCBI Jun. 10, 1999 9:01 am).

Accession No. AF432221.1 (GI No. 19851935, first seen at NCBI Apr. 1, 2002 12:19 am).

Accession No. AAK61242.1 (GI No. 14336710, first seen at NCBI Jun. 11, 2001 3:07 pm).

Accession No. AAD33400.1 (GI No. 4928064, first seen at NCBI Jun. 1, 1999 12:07 am).

Accession No. AAC18038.1 (GI No. 3170178, first seen at NCBI Jun. 2, 1998 12:21 am).

Figure 1A-1. Isolated ME-5 cDNA sequence

SEQUENCE LISTING
GENERAL INFORMATION:
NUMBER OF SEQ ID NOS. 9
SEQUENCE CHARACTERISTICS:
SEQ ID NO 1
LENGTH: 1302
TYPE: DNA
ORGANISM: Homo sapiens
FEATURE: SEQUENCE: 1

```
CCGGGAATGAAGGGCCAAGGATCGCGGGCTCGGGCTGCGGGGCTCCGGCTGCGGGCGCTGGGCCGCGAGGCGCGGAGCTTGGGAGCGGAGCCCA
                                                                                          94
GGCCCTTACTTCCCGGTTCCTAGCGCCCGAGCCCGACGCCCCGAGGCCGACGCCCGCGACCCGGCGCTCCGCGCCTCGAACCCTCGCCTCGGGT

GGCCGTGCCGCGCGGCGCATGAAGGGCAAGGAGGAGAAGGAGGGCGGCGCACGGCTGGGCGCTGGGGGCGGAAGCCCCGAGAAGAGCCCGAGCG
                                                                                          188
CCGGCACGGCGCGCCGCGTACTTCCCGTTCCTCGTCTTCCTCCCGCCGCGTGCCGACCCGCGACCGCCGCCTTCGGGGCTCTTCTCGGGCTCGC

CGCAGGAGCTCAAGGAGCAGGGCAATCGTCTGTTCGTGGGCCGAAAGTACCCGGAGGCGGCGGCCTGCTACGGCGCGCGGATCACCCGGAACCC
                                                                                          282
GCGTCCTCGAGTTCCTCGTCCCGTTAGCAGACAAGCACCCGGCTTTCATGGGCCTCCGCCGCCGGACGATGCCGGCGCGCTAGTGGCCTTGGG

GCTGGTGGCCGTGTATTACAGCAACCGGGCCTTGTGCTACCTGAAGATGCAGCAGCACGAGCAGGCCCTGGCCGACTGCCGGCGCGCCCTGGAG
                                                                                          376
CGACCACCGGCACATAATGTGGTTGGCCCGGAACACGATGGACTTCTACGTCGTCGTGCTCGTCCGGGACCGGCTGACGGCCGCGCGGGACCTC

CTGGACGGGCAGTCTGTGAAGGCGCACTTCTTCCTGGGGCAGTGCCAGCTGGAGATGGAGAGCTATGATGAGGCCATCGCCAATCTGCAGCGAG
                                                                                          470
GACCTGCCCGTCAGACACTTCCGCGTGAAGAAGGACCCCGTCACGGTCGACCTCTACCTCTGATACTACTCCGGTAGCGGTTAGACGTCGCTC

CTTACAGCCTGGCCAAGGAGCAGCGGCTGAACTTCGGGGACGACATCCCCAGCGCTCTTCGAATCGCGAAGAAGAAGCGCTGGAACAGCATTGA
                                                                                          564
GAATGTCGGACCGGTTCCTCGTCGCCGACTTGAAGCCCCTGCTGTAGGGGTCGCGAGAAGCTTAGCGCTTCTTCTTCGCGGACCTTGTCGTAACT

GGAGCGGCGCATCCACCAGGAGAGCGAGCTGCACTCCTACCTCTCCAGGCTCATTGCCGCGGAGCGTGAGAGGGAGCTGGAAGAGTGCCAGCGA
                                                                                          658
CCTCGCCGCGTAGGTGGTCCTCTCGCTCGACGTGAGGATGGAGAGGTCCGAGTAACGGCGCCTCGCACTCTCCCTCGACCTTCTCACGGTCGCT

AACCACGAGGGTGATGAGGACGACAGCCACGTCCGGGCCCAGCAGGCCTGCATTGAGGCCAAGCACGACAAGTACATGGCGGACATGGACGAGC
                                                                                          752
TTGGTGCTCCCACTACTCCTGCTGTCGGTGCAGGCCCGGGTCGTCGGACGTAACTCCGGTTCGTGCTGTTCATGTACCGCCTGTACCTGCTCG

TTTTTTCTCAGGTGGATGAGAAGAGGAAGAAGCGAGACATCCCCGACTACCTGTGTGGCAAGATCAGCTTTGAGCTGATGCGGGAGCCGTGCAT
                                                                                          846
AAAAAAGAGTCCACCTACTCTTCTCCTTCTTCGCTCTGTAGGGGCTGATGGACACACCGTTCTAGTCGAAACTCGACTACGCCCTCGGCACGTA

CACGCCCAGTGGGATCACCTACGACCGCAAGGACATCGAGGAGCACCTGCAGCGTGTGGGTCATTTTGACCCCGTGACCCGGAGCCCCCTGACC
                                                                                          940
GTGCGGGTCACCCGTAGTGGATGCTGGCGTTCCTGTAGCTCCTCGTGGACGTCGCACACCCAGTAAAACTGGGGCACTGGGCCTCGGGGACTGG
```

Figure 1A-2. Isolated ME-5 cDNA sequence

```
CAGGAACAGCTCATCCCCAACTTGGCTATGAAGGAGGTTATTGACGCATTCATCTCTGAGAATGGCTGGGTGGAGGACTACTGAGGTTCCCTGC
------------------------------------------------------------------------------------------------ 1034
GTCCTTGTCGAGTAGGGGTTGAACCGATACTTCCTCCAATAACTGCGTAAGTAGAGACTCTTACCGACCCACCTCCTGATGACTCCAAGGGACG

CCTACCTGGCGTCCTGGTCCAGGGGAGCCCTGGGCAGAAGCCCCGGCCCTATACATAGTTTATGTTCCTGGCCACGCCGACCGCTTCCCCCA
------------------------------------------------------------------------------------------------ 1128
GGATGGACCGCAGGACCAGGTCCCCTCGGGACCCGTCTTCGGGGGCCGGGGATATGTATCAAATACAAGGACCGGTGGGGCTGGCGAAGGGGGT

AGTTCTGCTGTTGGACTCTGGACTGTTTCCCCTCTCAGCATCGCTTTTGCTGGGCCGTGATCGTCCCCCTTTGTGGGCTGGAAAAGCAGGTGAG
------------------------------------------------------------------------------------------------ 1222
TCAAGACGACAACCTGAGACCTGACAAAGGGGAGAGTCGTAGCGAAAACGACCCGGCACTAGCAGGGGGAAAACACCCGACCTTTTCGTCCACTC

GGTGGGCTGGGCTGAGGCCATTGCCGCCACTATCTGTGTAATAAAATCCGTGAGCACGAAAAAAAAAAAAAAAAAAAAAAAA
------------------------------------------------------------------------------------------------ 1302
CCACCCGACCCGACTCCGGTAACGGCGGTGATAGACACATTATTTTAGGCACTCGTGCTTTTTTTTTTTTTTTTTTTTTTTT
```

Figure 1B. Deduced ME-5 coding sequence.

SEQUENCE LISTING
GENERAL INFORMATION:
NUMBER OF SEQ ID NOS: 9
SEQUENCE CHARACTERISTICS:
SEQ ID NO 2
LENGTH: 912
TYPE: DNA
ORGANISM: Homo sapiens
FEATURE: SEQUENCE: 2

```
ATGAAGGGCAAGGAGGAGAAGGAGGGCGGCGCACGGCTGGGCGCTGGCGGCGGAAGCCCCGAGAAGAGCCCGAGCGCGCAGGAGCTCAAGGAGC
------------------------------------------------------------------------------------------------ 94
TACTTCCCGTTCCTCCTCTTCCTCCCGCCGCGTGCCGACCCGCGACCGCCGCCTTCGGGGCTCTTCTCGGGCTCGCGCGTCCTCGAGTTCCTCG

AGGGCAATCGTCTGTTCGTGGGCCGAAAGTACCCGGAGGCGGCGGCCTGCTACGGCCGCGCGATCACCCGGAACCCGCTGGTGGCCGTGTATTA
------------------------------------------------------------------------------------------------ 188
TCCCGTTAGCAGACAAGCACCCGGCTTTCATGGGCCTCCGCCGCCGGACGATGCCGGCGCGCTAGTGGGCCTTGGGCGACCACCGGCACATAAT

CACCAACCGGGCCTTGTGCTACCTGAAGATGCAGCAGCACGAGCAGGCCCTGGCCGACTGCCGGCGCGCCCTGGAGCTGGACGGGCAGTCTGTG
------------------------------------------------------------------------------------------------ 282
GTGGTTGGCCCGGAACACGATGGACTTCTACGTCGTCGTGCTCGTCCGGGACCGGCTGACGGCCGCGCGGGACCTCGACCTGCCCGTCAGACAC

AAGGCGCACTTCTTCCTGGGGCAGTGCCAGCTGGAGATGGAGAGCTATGATGAGGCCATCGCCAATCTGCAGCGAGCTTACAGCCTGGCCAAGG
------------------------------------------------------------------------------------------------ 376
TTCCGCGTGAAGAAGGACCCCGTCACGGTCGACCTCTACCTCTCGATACTACTCCGGTAGCGGTTAGACGTCGCTCGAATGTCGGACCGGTTCC

AGCAGCGGCTGAACTTCGGGGACGACATCCCCAGCGCTCTTCGAATCGCGAAGAAGAAGCGCTGGAACAGCATTGAGGAGCGGCGCATCCACCA
------------------------------------------------------------------------------------------------ 470
TCGTCGCCGACTTGAAGCCCCTGCTGTAGGGGTCGCGAGAAGCTTAGCGCTTCTTCTTCGCGACCTTGTCGTAACTCCTCGCCGCGTAGGTGGT

GGAGAGCGAGCTGCACTCCTACCTCTCCAGGCTCATTGCCGCGGAGCGTGAGAGGGAGCTGGAAGAGTGCCAGCGAAACCACGAGGGTGATGAG
------------------------------------------------------------------------------------------------ 564
CCTCTCGCTCGACGTGAGGATGGAGAGGTCCGAGTAACGGCGCCTCGCACTCTCCCTCGACCTTCTCACGGTCGCTTTGGTGCTCCCACTACTC

GACGACAGCCACGTCCGGGCCCAGCAGGCCTGCATTGAGGCCAAGCACGACAAGTACATGGCGGACATGGACGAGCTTTTTTCTCAGGTGGATG
------------------------------------------------------------------------------------------------ 658
CTGCTGTCGGTGCAGGCCCGGGTCGTCCGGACGTAACTCCGGTTCGTGCTGTTCATGTACCGCCTGTACCTGCTCGAAAAAAGAGTCCACCTAC

AGAAGAGGAAGAAGCGAGACATCCCCGACTACCTGTGTGGCAAGATCAGCTTTGAGCTGATGCGGGAGCCGTGCATCACGCCCAGTGGCATCAC
------------------------------------------------------------------------------------------------ 752
TCTTCTCCTTCTTCGCTCTGTAGGGGCTGATGGACACACCGTTCTAGTCGAAACTCGACTACGCCCTCGGCACGTAGTGCGGGTCACCGTAGTG

CTACGACCGCAAGGACATCGAGGAGCACCTGCAGCGTGTGGGTCATTTTGACCCCGTGACCCGGAGCCCCTGACCCAGGAACAGCTCATCCCC
------------------------------------------------------------------------------------------------ 846
GATGCTGGCGTTCCTGTAGCTCCTCGTGGACGTCGCACACCCAGTAAAACTGGGGCACTGGGCCTCGGGGGACTGGGTCCTTGTCGAGTAGGGG

AACTTGGCTATGAAGGAGGTTATTGACGCATTCATCTCTGAGAATGGCTGGGTGGAGGACTACTGA
------------------------------------------------------------- 912
TTGAACCGATACTTCCTCCAATAACTGCGTAAGTAGAGACTCTTACCGACCCACCTCCTGATGACT
```

Figure 1C. Deduced ME-5 amino acid sequence.

SEQUENCE LISTING
GENERAL INFORMATION:
NUMBER OF SEQ ID NOS: 9
SEQUENCE CHARACTERISTICS:
SEQ ID NO 3
LENGTH: 303
TYPE: PRT
ORGANISM: Homo sapiens
FEATURE: SEQUENCE: 3

| | |
|---|---|
| MKGKEEKEGGARLGAGGGSPEKSPSAQELKEQGNRLFVGRKYPEAAACYG | 50 |
| RAITRNPLVAVYYTNRALCYLKMQQHEQALADCRRALELDGQSVKAHFFL | 100 |
| GQCQLEMESYDEAIANLQRAYSLAKEQRLNFGDDIPSALRIAKKKRWNSI | 150 |
| EERRIHQESELHSYLSRLIAAERERELEECQRNHEGDEDDSHVRAQQACI | 200 |
| EAKHDKYMADMDELFSQVDEKRKKRDIPDYLCGKISFELMREPCITPSGI | 250 |
| TYDRKDIEEHLQRVGHFDPVTRSPLTQEQLIPNLAMKEVIDAFISENGWV | 300 |
| EDY | 303 |

Figure 2A-1. Isolated ME-2 cDNA sequence

SEQUENCE LISTING
GENERAL INFORMATION:
NUMBER OF SEQ ID NOS: 9
SEQUENCE CHARACTERISTICS:
SEQ ID NO 4
LENGTH: 1353
TYPE: DNA
ORGANISM: Homo sapiens
FEATURE: SEQUENCE: 4

```
CTGACATGCAGCCCTCTGGACCCCGAGGTTGGACCCTACTGTGACACACCTACCATGCGGACACTCTTCAACCTCCTCTGGCTTGCCCTG
----------+---------+---------+---------+---------+---------+---------+---------+---------+  90
GACTGTACGTCGGGAGACCTGGGGCTCCAACCTGGGATGACACTGTGTGGATGGTACGCCTGTGAGAAGTTGGAGGAGACCGAACGGGAC

GCCTGCAGCCCTGTTCACACTACCCTGTCAAAGTCAGATGCCAAAAAAGCCGCCTCAAAGACGCTGCTGGAGAAGAGTCAGTTTTCAGAT
----------+---------+---------+---------+---------+---------+---------+---------+---------+  180
CGGACGTCGGGACAAGTGTGATGGGACAGTTTCAGTCTACGGTTTTTTCGGCGGAGTTTCTGCGACGACCTCTTCTCAGTCAAAAGTCTA

AAGCCGGTGCAAGACCGGGGTTTGGTGGTGACGGACCTCAAAGCTGAGAGTGTGGTTCTTGAGCATCGCAGCTACTGCTCGGCAAAGGCC
----------+---------+---------+---------+---------+---------+---------+---------+---------+  270
TTCGGCCACGTTCTGGCCCCAAACCACCACTGCCTGGAGTTTCGACTCTCACACCAAGAACTCGTAGCGTCGATGACGAGCCGTTTCCGG

CGGGACAGACACTTTGCTGGGGATGTACTGGGCTATGTCACTCCATGGAACAGCCATGGCTACGATGTCACCAAGGTCTTTGGGAGCAAG
----------+---------+---------+---------+---------+---------+---------+---------+---------+  360
GCCCTGTCTGTGAAACGACCCCTACATGACCCGATACAGTGAGGTACCTTGTCGGTACCGATGCTACAGTGGTTCCAGAAACCCTCGTTC

TTCACACAGATCTCACCCGTCTGGCTGCAGCTGAAGAGACGTGGCCGTGAGATGTTTGAGGTCACGGGCCTCCACGACGTGGACCAAGGG
----------+---------+---------+---------+---------+---------+---------+---------+---------+  450
AAGTGTGTCTAGAGTGGGCAGACCGACGTCGACTTCTCTGCACCGGCACTCTACAAACTCCAGTGCCCGGAGGTGCTGCACCTGGTTCCC

TGGATGCGAGCTGTCAGGAAGCATGCCAAGGGCCTGCACATAGTGCCTCGGCTCCTGTTTGAGGACTGGACTTACGATGATTTCCGGAAC
----------+---------+---------+---------+---------+---------+---------+---------+---------+  540
ACCTACGCTCGACAGTCCTTCGTACGGTTCCCGGACGTGTATCACGGAGCCGAGGACAAACTCCTGACCTGAATGCTACTAAAGGCCTTG

GTCTTAGACAGTGAGGATGAGATAGAGGAGCTGAGCAAGACCGTGGTCCAGGTGGCAAAGAACCAGCATTTCGACGGCTTCGTGGTGGAG
----------+---------+---------+---------+---------+---------+---------+---------+---------+  630
CAGAATCTGTCACTCCTACTCTATCTCCTCGACTCGTTCTGGCACCAGGTCCACCGTTTCTTGGTCGTAAAGCTGCCGAAGCACCACCTC

GTCTGGAACCAGCTGCTAAGCCAGAAGCGCGTGGGCCTCATCCACATGCTCACCCACTTGGCCGAGGCTCTGCACCAGGCCCGGCTGCTG
----------+---------+---------+---------+---------+---------+---------+---------+---------+  720
CAGACCTTGGTCGACGATTCGGTCTTCGCGCACCCGGAGTAGGTGTACGAGTGGGTGAACCGGCTCCGAGACGTGGTCCGGGCCGACGAC

GCCCTCCTGGTCATCCCGCCTGCCATCACCCCCGGGACCGACCAGCTGGGCATGTTCACGCACAAGGAGTTTGAGCAGCTGGCCCCCGTG
----------+---------+---------+---------+---------+---------+---------+---------+---------+  810
CGGGAGGACCAGTAGGGCGGACGGTAGTGGGGGCCCTGGCTGGTCGACCCGTACAAGTGCGTGTTCCTCAAACTCGTCGACCGGGGGCAC
```

Figure 2A-2. Isolated ME-2 cDNA sequence

```
CTGGATGGTTTCAGCCTCATGACCTACGACTACTCTACAGCGCATCAGCCTGGCCCTAATGCACCCCTGTCCTGGGTTCGAGCCTGCGTC
----------+---------+---------+---------+---------+---------+---------+---------+---------+ 900
GACCTACCAAAGTCGGAGTACTGGATGCTGATGAGATGTCGCGTAGTCGGACCGGGATTACGTGGGGACAGGACCCAAGCTCGGACGCAG

CAGGTCCTGGACCCGAAGTCCAAGTGGCGAAGCAAAATCCTCCTGGGGCTCAACTTCTATGGTATGGACTACGCGACCTCCAAGGATGCC
----------+---------+---------+---------+---------+---------+---------+---------+---------+ 990
GTCCAGGACCTGGGCTTCAGGTTCACCGCTTCGTTTTAGGAGGACCCCGAGTTGAAGATACCATACCTGATGCGCTGGAGGTTCCTACGG

CGTGAGCCTGTTGTCGGGGCCAGGTACATCCAGACACTGAAGGACCACAGGCCCCGGATGGTGTGGGACAGCCAGGCCTCAGAGCACTTC
----------+---------+---------+---------+---------+---------+---------+---------+---------+ 1080
GCACTCGGACAACAGCCCCGGTCCATGTAGGTCTGTGACTTCCTGGTGTCCGGGGCCTACCACACCCTGTCGGTCCGGAGTCTCGTGAAG

TTCGAGTACAAGAAGAGCCGCAGTGGGAGGCACGTCGTCTTCTACCCAACCCTGAAGTCCCTGCAGGTGCGGCTGGAGCTGGCCCGGGAG
----------+---------+---------+---------+---------+---------+---------+---------+---------+ 1170
AAGCTCATGTTCTTCTCGGCGTCACCCTCCGTGCAGCAGAAGATGGGTTGGGACTTCAGGGACGTCCACGCCGACCTCGACCGGGCCCTC

CTGGGCGTTGGGGTCTCTATCTGGGAGCTGGGCCAGGGCCTGAACTACTTCTACGACCTGCTCTAGGTGGXCATTGCGGCCTCCGCGGTG
----------+---------+---------+---------+---------+---------+---------+---------+---------+ 1260
GACCCGCAACCCCAGAGATAGACCCTCGACCCGGTCCGGACTTGATGAAGATGCTGGACGAGATCCACCCGTAACGCCGGAGGCGCCAC

GACGTGTTCTTTTCTAATGCCATGGAGTGAGTGAGCAGGTGTGAAATACAGGCCTCCACTCCGTTTGCTGTGAAAAAAAAAAAAAAAAAA
----------+---------+---------+---------+---------+---------+---------+---------+---------+ 1350
CTGCACAAGAAAAGATTACGGTACCTCACTCACTCGTCCACACTTTATGTCCGGAGGTGAGGCAAACGACACTTTTTTTTTTTTTTTTTT

AAA
---+ 1353
TTT
```

Figure 2B-1. Deduced ME-2 coding sequence

SEQUENCE LISTING
GENERAL INFORMATION:
NUMBER OF SEQ ID NOS: 9
SEQUENCE CHARACTERISTICS:
SEQ ID NO 5
LENGTH: 1182
TYPE: DNA
ORGANISM: Homo sapiens
FEATURE: SEQUENCE: 5

```
ATGCGGACACTCTTCAACCTCCTCTGGCTTGCCCTGGCCTGCAGCCCTGTTCACACTACCCTGTCAAAGTCAGATGCCAAAAAGCCGCCTCA
                                                                                            93
TACGCCTGTGAGAAGTTGGAGGAGACCGAACGGGACGGACGTCGGGACAAGTGTGATGGGACAGTTTCAGTCTACGGTTTTTTCGGCGGAGT

AAGACGCTGCTGGAGAAGAGTCAGTTTTCAGATAAGCCGGTGCAAGACCGGGGTTTGGTGGTGACGGACCTCAAAGCTGAGAGTGTGGTTCTT
                                                                                            186
TTCTGCGACGACGTCTTCTCAGTCAAAAGTCTATTCGGCCACGTTCTGGCCCCAAAGCCACCACTGCCTGGAGTTTCGACTCTCACACCAAGAA

GAGCATCGCAGCTACTGCTCGGCAAAGGCCCGGGACAGACACTTTGCTGGGGATGTACTGGGCTATGTCACTCCATGGAACAGCCATGGCTAC
                                                                                            279
CTCGTAGCGTCGATGACGAGCCGTTTCCGGGCCCTGTCTGTGAAACGACCCCTACATGACCCGATACAGTGAGGTACCTTGTCGGTACCGATG

GATGTCACCAAGGTCTTTGGGAGCAAGTTCACACAGATCTCACCCGTCTGGCTGCAGCTGAAGAGACGTGGCCGTGAGATGTTTGAGGTCACG
                                                                                            372
CTACAGTGGTTCCAGAAACCCTCGTTCAAGTGTGTCTAGAGTGGGCAGACCGACGTCGACTTCTCTGCACCGGCACTCTACAAACTCCAGTGC

GGGCTCCACGACGTGGACCAAGGGTGGATGCGAGCTGTCAGGAAGCATGCCAAGGGCCTGCACATAGTGCCTCGGCTCCTGTTTGAGGACTGG
                                                                                            465
CCCGAGGTGCTGCACCTGGTTCCCACCTACGCTCGACAGTCCTTCGTACGGTTCCCGGACGTGTATCACGGAGCCGAGGACAAAGTCCTGACC

ACTTACGATGATTTCCGGAACGTCTTAGACAGTGAGGATGAGATAGAGGAGCTGAGCAAGACCGTGGTCCAGGTGGCAAAGAACCAGCATTTC
                                                                                            558
TGAATGCTACTAAAGGCCTTGCAGAATCTGTCACTCCTACTCTATCTCCTCGACTCGTTCTGGCACCAGGTCCACCGTTTCTTGGTCGTAAAG

GACGGCTTCGTGGTGGAGGTCTGGAACCAGCTGCTAAGCCAGAAGCGCGTGGGCCTCATCCACATGCTCACCCACTTGGCCGAGGCTCTGCAG
                                                                                            651
CTGCCGAAGCACCACCTCCAGACCTTGGTCGACGATTCGGTCTTCGCGCACCCGGAGTAGGTGTACGAGTGGGTGAAGCGGCTCCGAGACGTG

CAGGCCCGGCTGCTGGCCCTCCTGGTCATCCCGCCTGCCATCACCCCCGGGACCGACCAGCTGGGCATGTTCACGCACAAGGAGTTTGAGCAG
                                                                                            744
GTCCGGGCCGACGACCGGGAGGACCAGTAGGGCGGACGGTAGTGGGGCCCTGGCTGGTCGACCCGTACAAGTGCGTGTTCCTCAAACTCGTC

CTGGCCCCCGTGCTGGATGGTTTCAGCCTCATGACCTACGACTACTCTACAGCGCATCAGCCTGGCCCTAATGCACCCCTGTCCTGGGTTCGA
                                                                                            837
GACCGGGGCACGACCTACCAAAGTCGGAGTACTGGATGCTGATGAGATGTCGCGTAGTCGGACCGGGATTACGTGGGGACAGGACCCAAGCT
```

Figure 2B-2. Deduced ME-2 coding sequence

```
GCCTGCGTCCAGGTCCTGGACCCGAAGTCCAAGTGGCGAAGCAAAATCCTCCTGGGGCTCAACTTCTATGGTATGGACTACGCGACCTCCAAG
CGGACGCAGGTCCAGGACCTGGGCTTCAGGTTCACCGCTTCGTTTTAGGAGGACCCCGAGTTGAAGATACCATACCTGATGCGCTGGAGGTTC ──── 930

GATGCCCGTGAGCCTGTTGTCGGGGCCAGGTACATCCAGACACTGAAGGACCACAGGCCCCGGATGGTGTGGGACAGCCAGGCCTCAGAGCAC
CTACGGGCACTCGGACAACAGCCCCGGTCCATGTAGGTCTGTGACTTCCTGGTGTCCGGGGCCTACCACACCCTGTCGGTCCGGAGTCTCGTG ──── 1023

TTCTTCGAGTACAAGAAGAGCCGCAGTGGCAGGCACGTCGTCTTCTACCCAACCCTGAAGTCCCTGCAGGTGCGGCTGGAGCTGGCCCGGGAG
AAGAAGCTCATGTTCTTCTCGGCGTCACCCTCCGTGCAGCAGAAGATGGGTTGGACTTCAGGGACGTCCACGCCGACCTCGACCGGGCCCTC ──── 1116

CTGGGCGTTGGGGTCTCTATCTGGGAGCTGGGCCAGGGCCTGAACTACTTCTACGACCTGCTCGAG
GACCCGCAACCCCAGAGATAGACCCTCGACCCGGTCCCGGACTTGATGAAGATGCTGGACGAGATC ────→ 1182
```

Figure 2C. Deduced ME-2 amino acid sequence.

SEQUENCE LISTING
GENERAL INFORMATION:
NUMBER OF SEQ ID NOS: 9
SEQUENCE CHARACTERISTICS:
SEQ ID NO 6
LENGTH: 393
TYPE: PRT
ORGANISM: Homo sapiens
FEATURE: SEQUENCE: 6

| | |
|---|---|
| MRTLFNLLWLALACSPVHTTLSKSDAKKAASKTLLEKSQF | 40 |
| SDKPVQDRGLVVTDLKAESVVLEHRSYCSAKARDRHFAGD | 80 |
| VLGYVTPWNSHGYDVTKVFGSKFTQISPVWLQLKRRGREM | 120 |
| FEVTGLHDVDQGWMRAVRKHAKGLHIVPRLLFEDWTYDDF | 160 |
| RNVLDSEDEIEELSKTVVQVAKNQHFDGFVVEVWNQLLSQ | 200 |
| KRVGLIHMLTHLAEALHQARLLALLVIPPAITPGTDQLGM | 240 |
| FTHKEFEQLAPVLDGFSLMTYDYSTAHQPGPNAPLSWVRA | 280 |
| CVQVLDPKSKWRSKILLGLNFYGMDYATSKDAREPVVGAR | 320 |
| YIQTLKDHRPRMVWDSQASEHFFEYKKSRSGRHVVFYPTL | 360 |
| KSLQVRLELARELGVGVSIWELGQGLNYFYDLL | 393 |

Figure 3A-1. Isolated EPP-2 DNA Sequence

SEQUENCE LISTING
GENERAL INFORMATION:
NUMBER OF SEQ ID NOS: 9
SEQUENCE CHARACTERISTICS:
SEQ ID NO 7
LENGTH: 891
TYPE: DNA
ORGANISM: Homo sapiens
FEATURE: SEQUENCE: 7

```
CGGAAGACGAGGGCGGCGAGGTCGGGTTCCGGGCGCTTGGAGAAGATGGTGCTGCGGCGGCTGCTGGCCGCCCTGCTGCACAGCCCGCAG
----------+---------+---------+---------+---------+---------+---------+---------+---------+ 90
GCCTTCTGCTCCCGCCGCTCCAGCCCAAGGCCCGCGAACCTCTTCTACCACGACGCCGCCGACGACCGGCGGACGACGTGTCGGGCGTC

CTGGTGGAACGTCTGTCAGAGTCGCGGCCTATCCGACGTGCGGCGCAGCTCACGGCCTTCGCACTGCTGCAGGCCCAGCTGCGGGGCCAG
----------+---------+---------+---------+---------+---------+---------+---------+---------+ 180
GACCACCTTGCAGACAGTCTCAGCGCCGGATAGGCTGCACGCCGCGTCGAGTGCCGGAAGCGTGACGACGTCCGGGTCGACGCCCCGGTC

GACGCGGCCCGCCGGCCTGCAGGACCTCGCGGCTGGGCCCGTGGGCTCCCTGTGCCGCCGCGCTGAGCGATTTAGAGACGCCTTCACCCAG
----------+---------+---------+---------+---------+---------+---------+---------+---------+ 270
CTGCGCCGGGCGGCGGACGTCCTGGAGCGCCGACCCGGGCACCGAGGGACACGGCGGCGCGACTCGCTAAATCTCTGCGGAAGTGGGTC

GAGCTACGCCGCGGCCTCCGAGGCCGCTCGGGGCCACCACCAGGTAGCCAGAGGGGCCCTGGCGCAAACATTTAATCCTGGGCTGTGCGG
----------+---------+---------+---------+---------+---------+---------+---------+---------+ 360
CTCGATGCGGCGCCGGAGGCTCCGGCGAGCCCCGGTGGTGGTCCATCGGTCTCCCCGGGACCGCGTTTGTAAATTAGGACCCGACACGCC

GGCCGAAGCCGCTTGCTTTTCCTTCCGGGCTCTACAGTGGCATCAATGTGGAGGGGTCATTCCGGGCACTGCGCGCGGCTTCGAATCCCG
----------+---------+---------+---------+---------+---------+---------+---------+---------+ 450
CCGGCTTCGGCGAACGAAAAGGAAGGCCCGAGATGTCACCGTAGTTACACCTCCCCAGTAAGGCCCGTGACGCGCGGCCGAAGCTTAGCGC

ACTGGGATTGTTGGCCTGCAGACATCCCACGCATAAGAGCCTAGGCCAGACCGCCCGCTCCGTTGAAGTCTTGTGATTGGACAAGACACA
----------+---------+---------+---------+---------+---------+---------+---------+---------+ 540
TGACCCTAACAACCGGACGTCTGTAGGGTGCGTATTCTCGGATCCGGTCTGGCGGGCGAGGCAACTTCAGAACACTAACCTGTTCTGTGT

GTGTGGAGAAAGACCCCTAAGCCTAACAGAGATGAAGGTAGGCTGGGTCCAGACACGGCACCTACGGAGAGCCACGGACCGAAGCCAGAG
----------+---------+---------+---------+---------+---------+---------+---------+---------+ 630
CACACCTCTTTCTGGGATTCGGATTGTCTCTACTTCCATCCGACCCAGGTCTGTGCCGTGGATGCCTCTCGGTGCCTGGCTTCGGTCTC

AGCCTTTCCTCTGCAAGTGGGACTGAAACTCTTGACAGATGCTGCTCAATCTGACTGGTATAGCAGGACAGTTAATTCCAGGGACGATAT
----------+---------+---------+---------+---------+---------+---------+---------+---------+ 720
TCGGAAAGGAGACGTTCACCCTGACTTTGAGAACTGTCTACGACGAGTTAGACTGACCATATCGTCCTGTCAATTAAGGTCCCTGCTATA
```

Figure 3A-2. Isolated EPP-2 DNA Sequence

```
GGATGAAAAGACAACCCTACAGCTGCCAAATTCCTTTGATTAAATGTGTGAGCTGGTTGATAGGCATGAGTGTGATACTTCTCAGGCAAG
----------+---------+---------+---------+---------+---------+---------+---------+---------+  810
CCTACTTTTCTGTTGGGATGTCGACGGTTTAAGGAAACTAATTTACACACTCGACCAACTATCCGTACTCACACTATGAAGAGTCCGTTC

ATGTGTTAAGAATACCGGGGACTGTAGGCCTATGGTAATAATAAACACGTATTTTATGAAAAAAAAAAAAAAAAAAAAAAA
----------+---------+---------+---------+---------+---------+---------+---------+  891
TACACAATTCTTATGGCCCCTGACATCCGGATACCATTATTATTTGTGCATAAAATACTTTTTTTTTTTTTTTTTTTTTTT
```

Figure 3B. Deduced EPP-2 DNA Sequence

SEQUENCE LISTING
GENERAL INFORMATION:
NUMBER OF SEQ ID NOS: 9
SEQUENCE CHARACTERISTICS:
SEQ ID NO 8
LENGTH: 300
TYPE: DNA
ORGANISM: Homo sapiens
FEATURE: SEQUENCE: 8

```
ATGGTGCTGCGGCGGCTGCTGGCCGCCCTGCTGCACAGCCCGCAGCTGGTGGAACGTCTGTCAGAGTCGCGGCCTATCCGACGTGCGGCGCAGC
-------------------------------------------------------------------------------------------- 94
TACCACGACGCCGCCGACGACCGGCGGGACGACGTGTCGGGCGTCGACCACCTTGCAGACAGTCTCAGCGCCGGATAGGCTGCACGCCGCGTCG

TCACGGCCTTCGCACTGCTGCAGGCCCAGCTGCGGGGCCAGGACGCGGCCCGCCGCCTGCAGGACCTCGCGGCTGGGCCCGTGGGCTCCCTGTG
-------------------------------------------------------------------------------------------- 188
AGTGCCGGAAGCGTGACGACGTCCGGGTCGACGCCCCGGTCCTGCGCCGGGCGGCGGACGTCCTGGAGCGCCGACCCGGGCACCCGAGGGACAC

CCGCCGCGCTGAGCGATTTAGAGACGCCTTCACCCAGGAGCTACGCCGCGGCCTCCGAGGCCGCTCGGGGCCACCACCAGGTAGCCAGAGGGGC
-------------------------------------------------------------------------------------------- 282
GGCGGCGCGACTCGCTAAATCTCTGCGGAAGTGGGTCCTCGATGCGGCGCCGGAGGCTCCGGCGAGCCCCGGTGGTGGTCCATCGGTCTCCCCG

CCTGGCGCAAACATTTAA
------------------ 300
GGACCGCGTTTGTAAATT
```

Figure 3C. Deduced EPP-2 Amino Acid Sequence

SEQUENCE LISTING
GENERAL INFORMATION:
NUMBER OF SEQ ID NOS: 9
SEQUENCE CHARACTERISTICS:
SEQ ID NO 9
LENGTH: 99
TYPE: PRT
ORGANISM: Homo sapiens
FEATURE: SEQUENCE: 9

MVLRRLLAALLHSPQLVERLSESRPIRRAAQLTAFALLQAQLRGQDAARR 50

LQDLAAGPVGSLCRRAERFRDAFTQELRRGLRGRSGPPPGSQRGPGANI 99

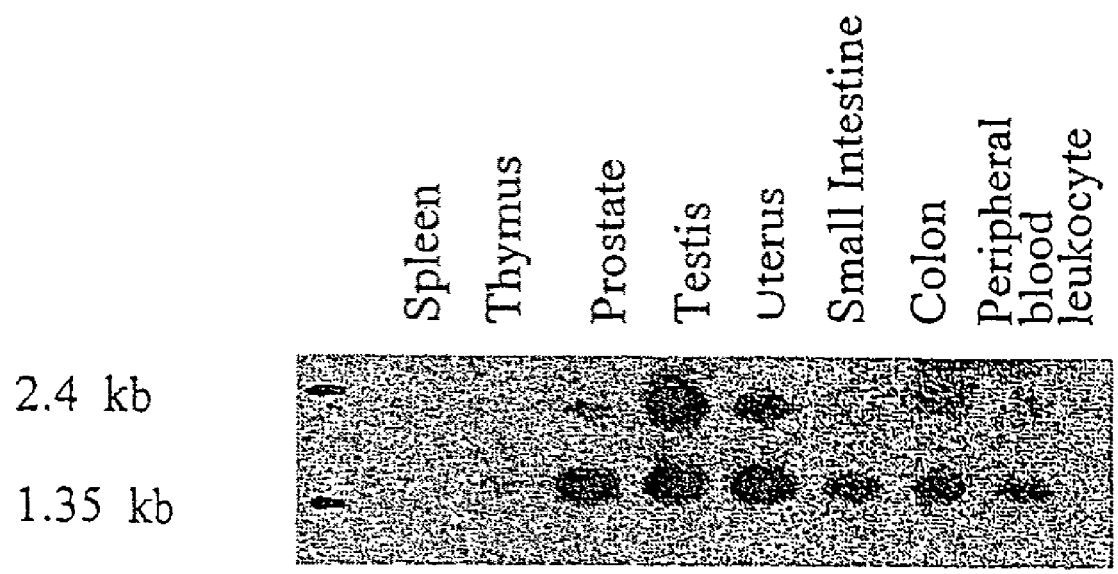
Figure 4. ME-5 Northern Blot.

Figure 5. ME-2 Northern Blot.
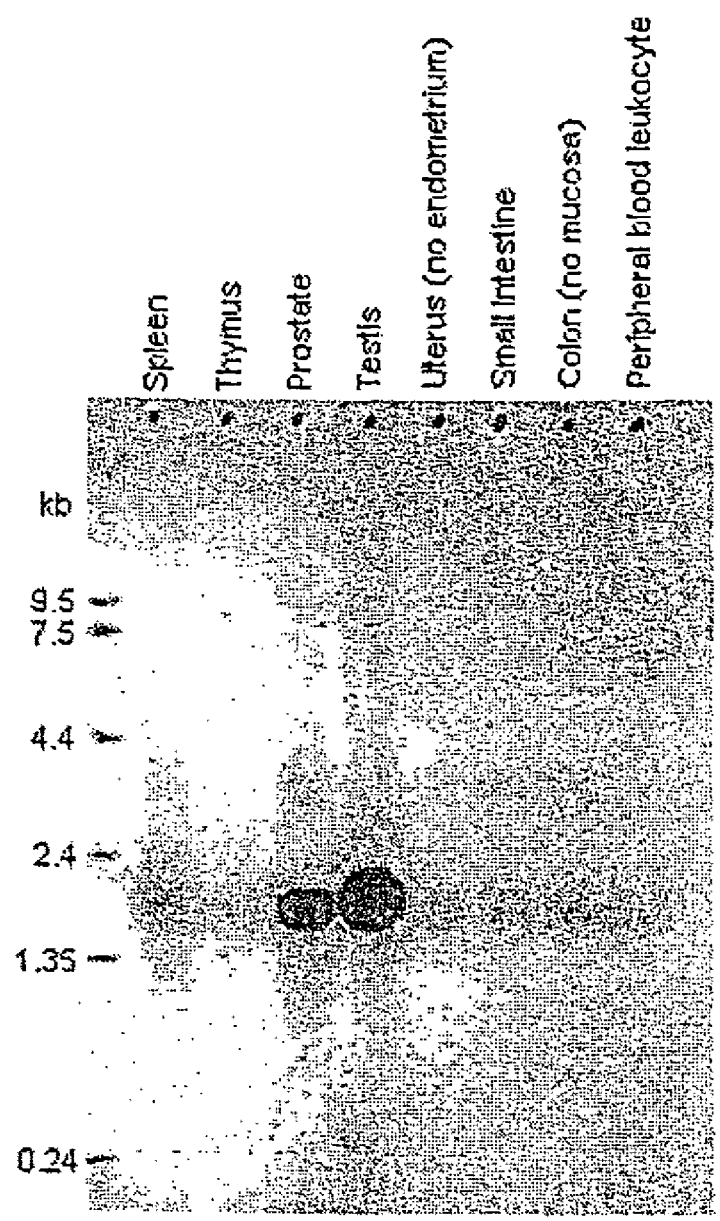

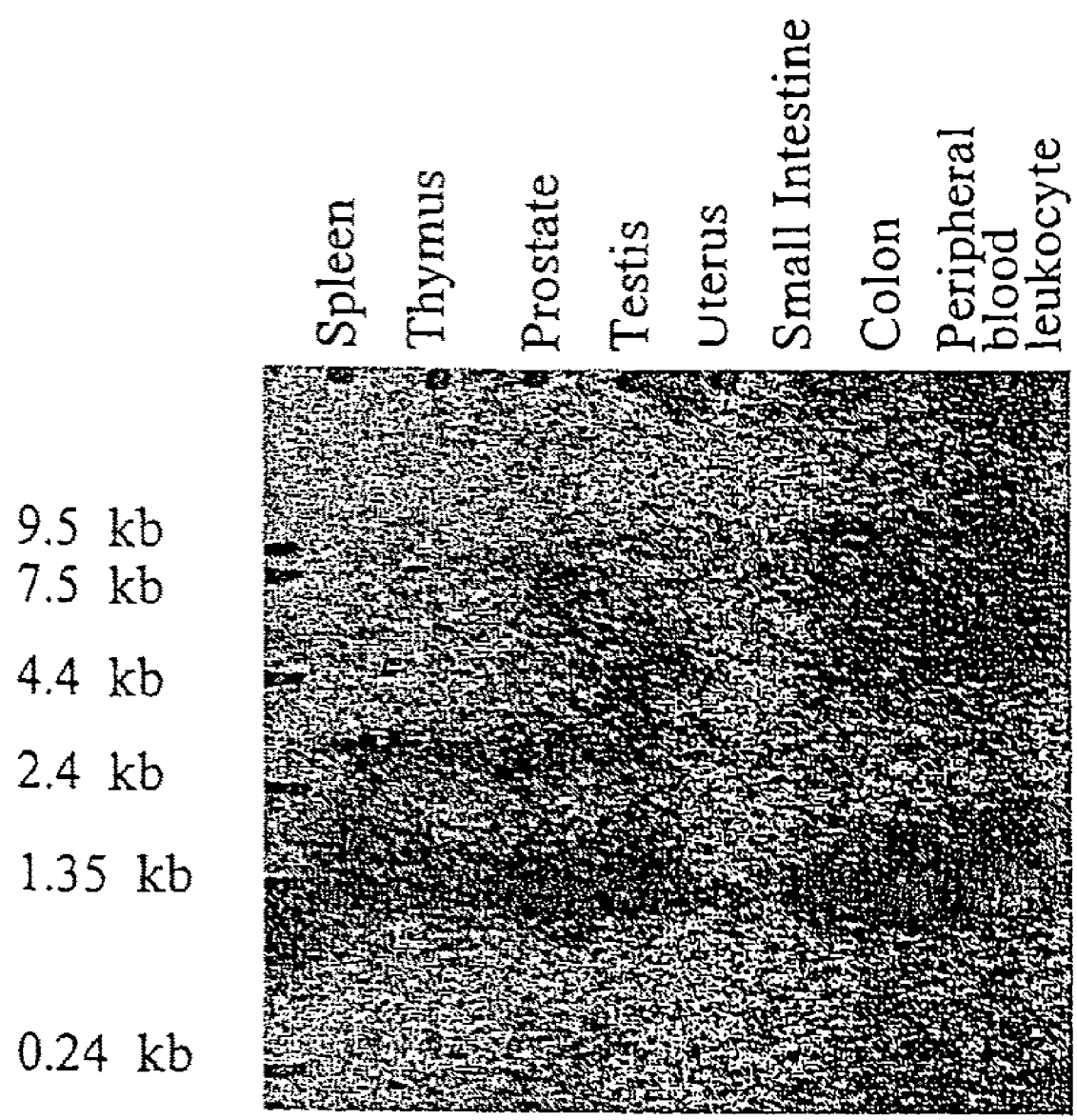
Figure 6. EPP-2 Northern blot.

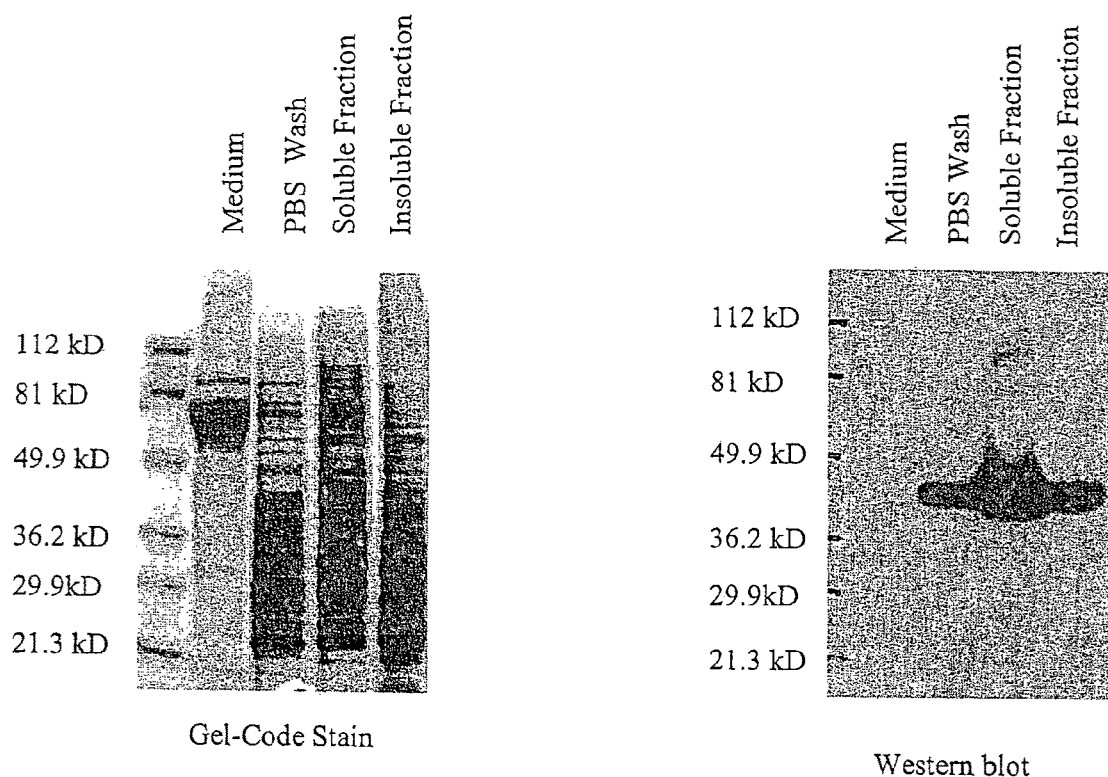
Figure 7. Recombinant ME-5 expression in insect cells.

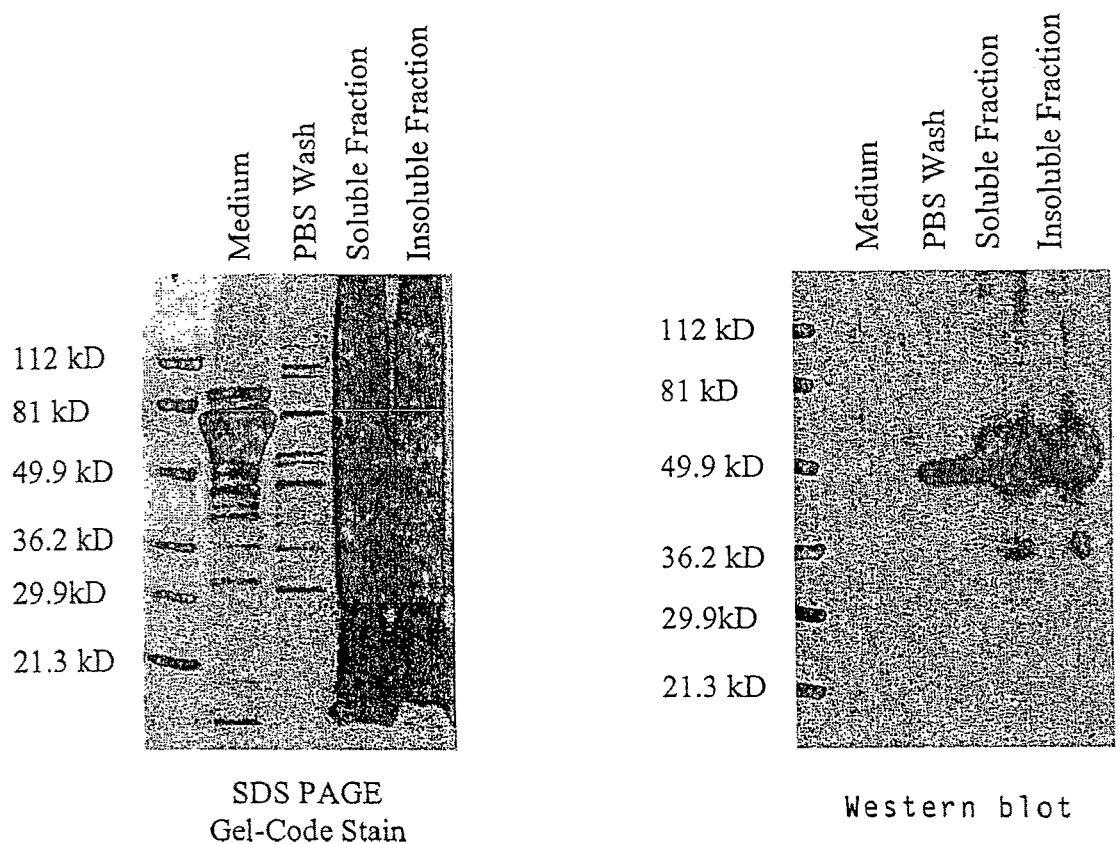
Figure 8. Recombinant ME-2 Expression In Insect Cells

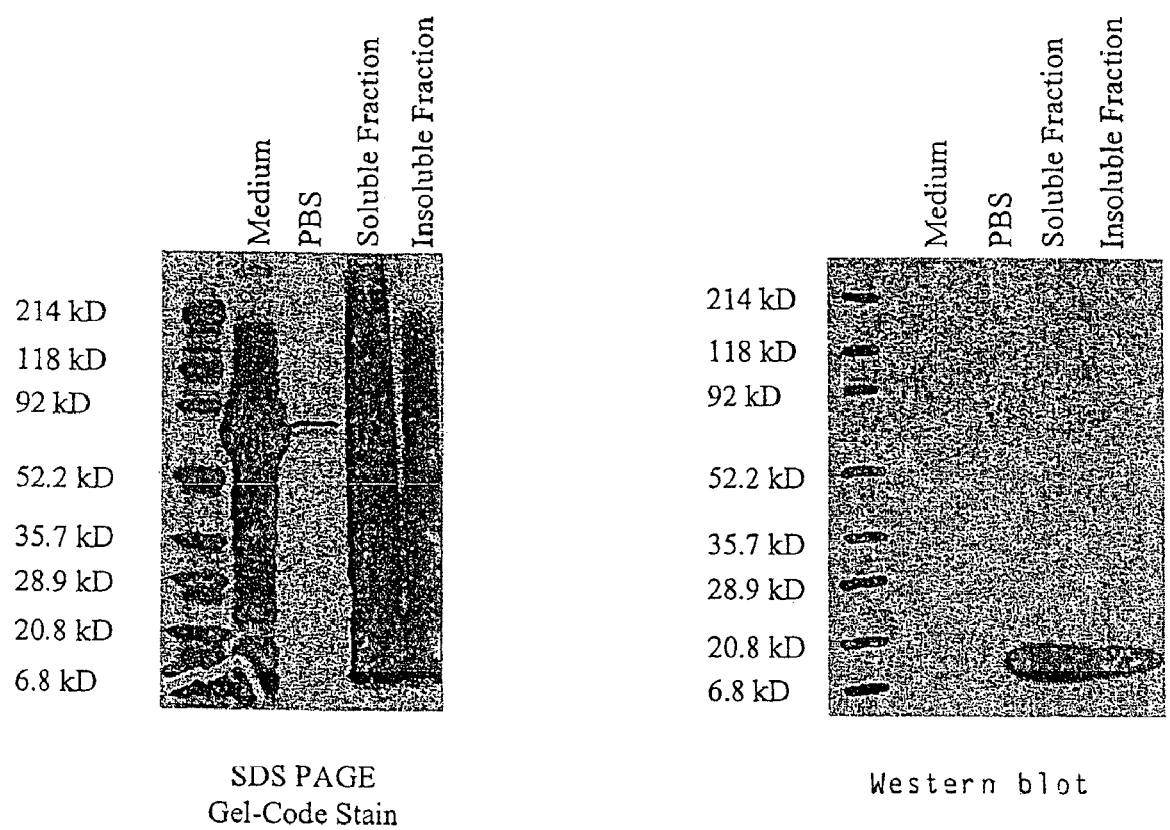
Figure 9. Recombinant EPP-2 expression in insect cells.

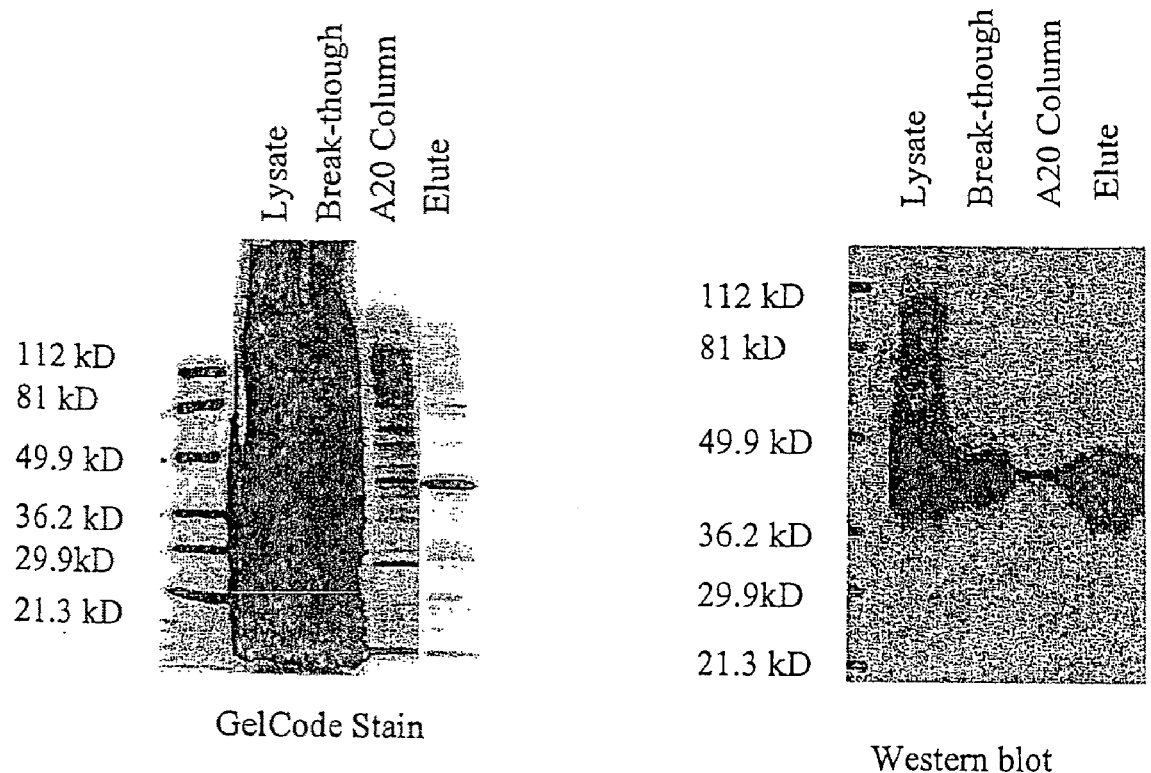
Figure 10. Recombinant ME-5 purification from insect cells

Figure 11. Recombinant ME-2 Purification from Insect Cells
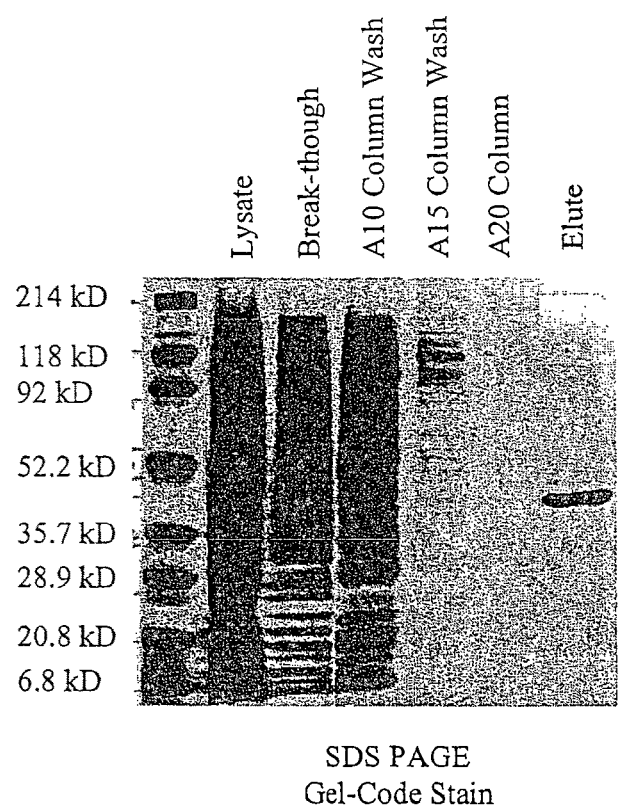
SDS PAGE
Gel-Code Stain
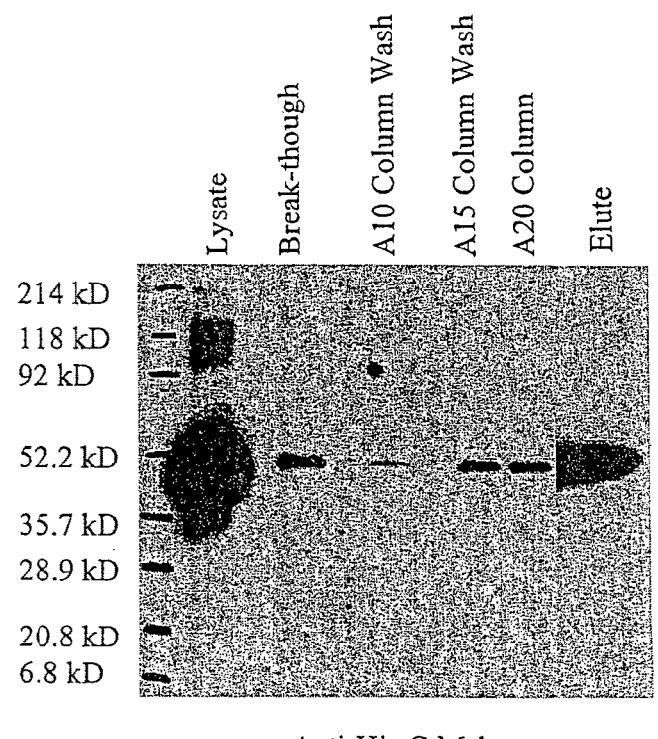
Anti-His G Mab

Figure 12. Recombinant EPP-2 purification from insect cells.
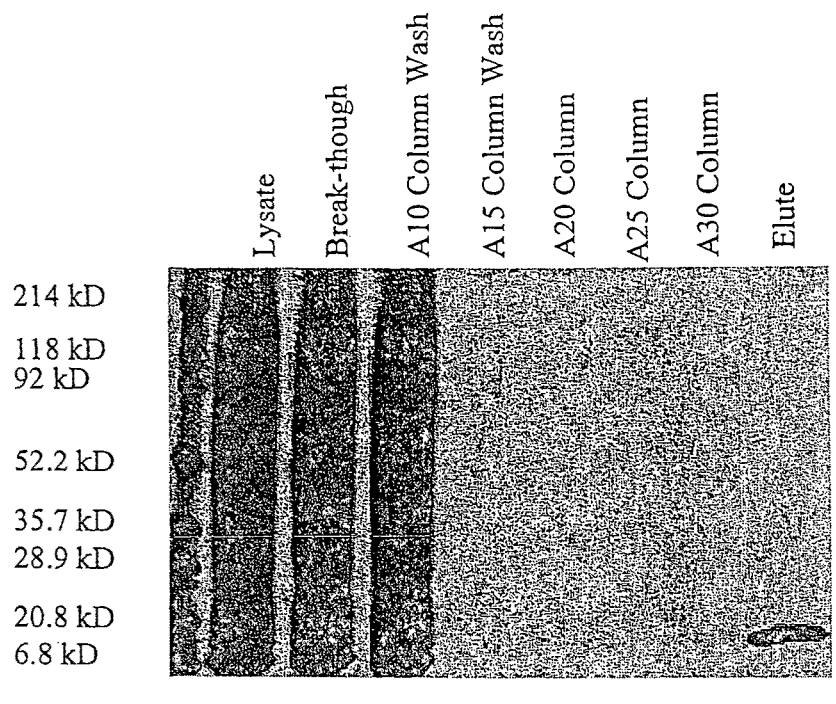
SDS PAGE
Gel-Code Stain
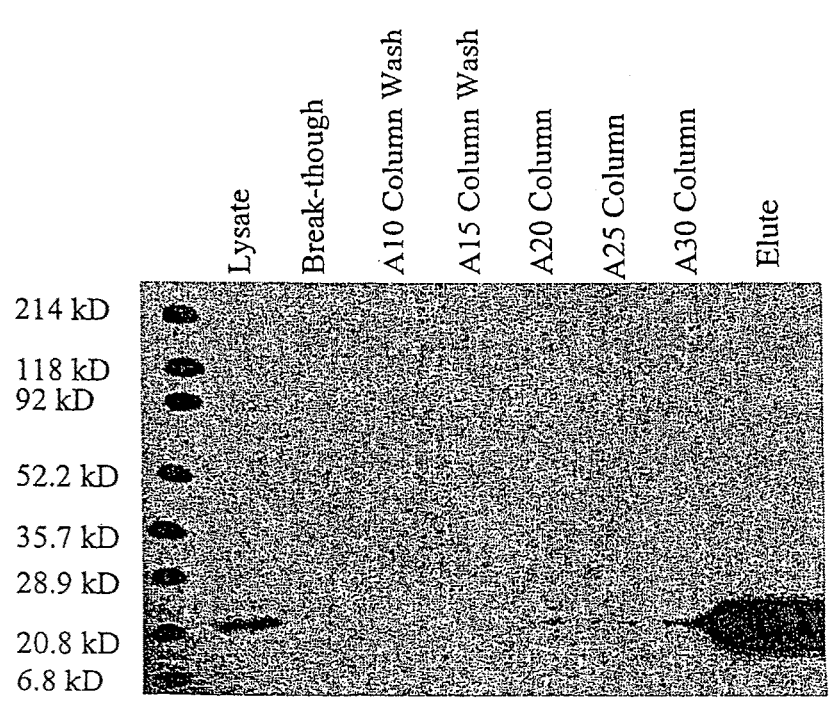
Anti-His G Mab

Figure 13. Identification of native ME-5 antigen
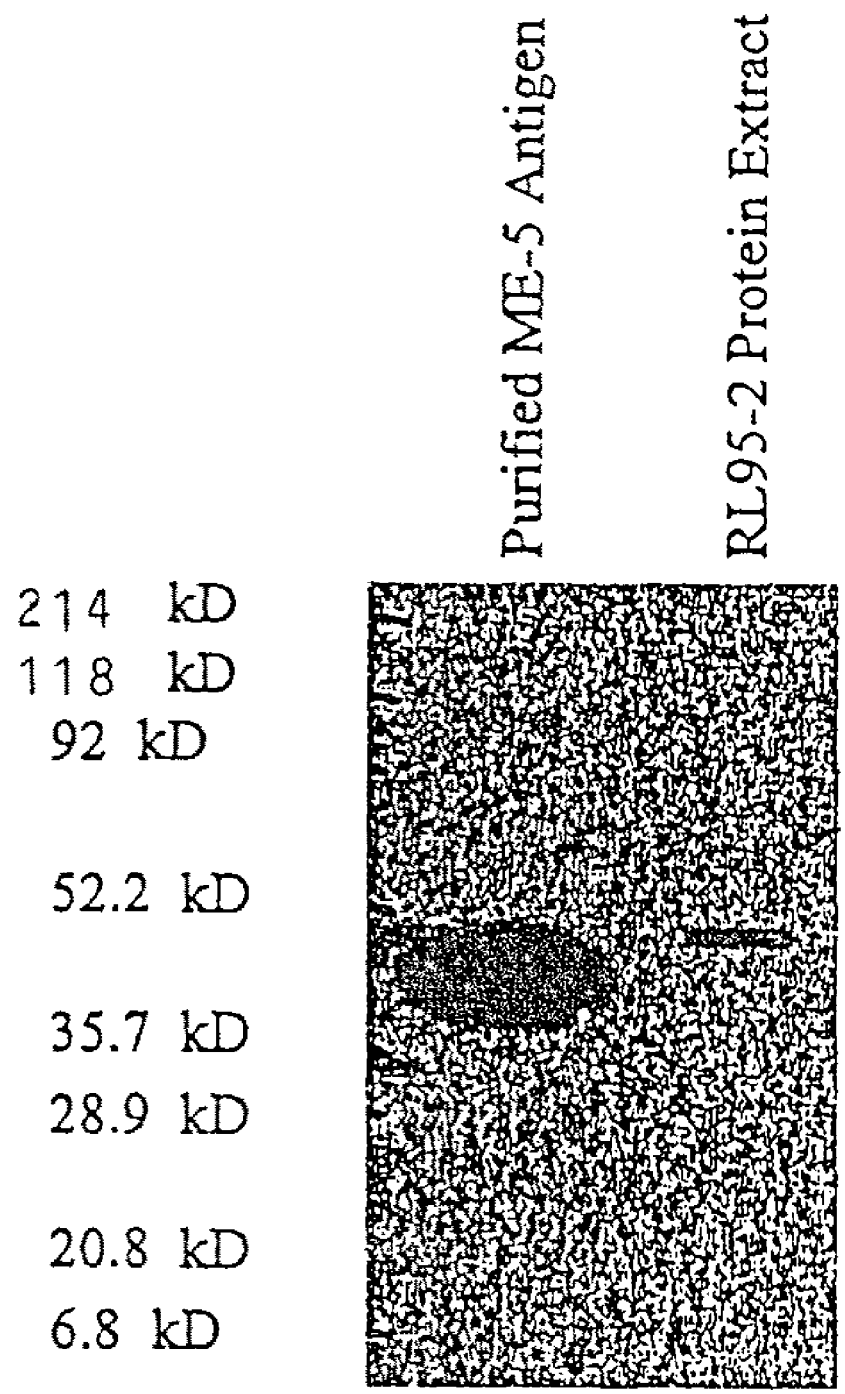

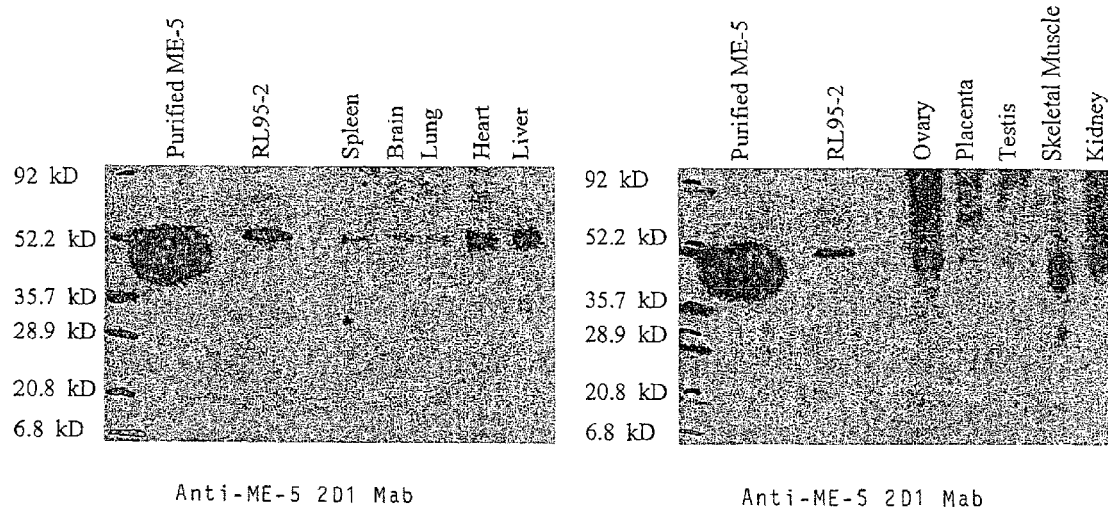
Figure 14. Tissue Distribution of native ME-5 protein.

Figure 15A. Reactivity of control sera with recombinant ME-5 on lineblots.
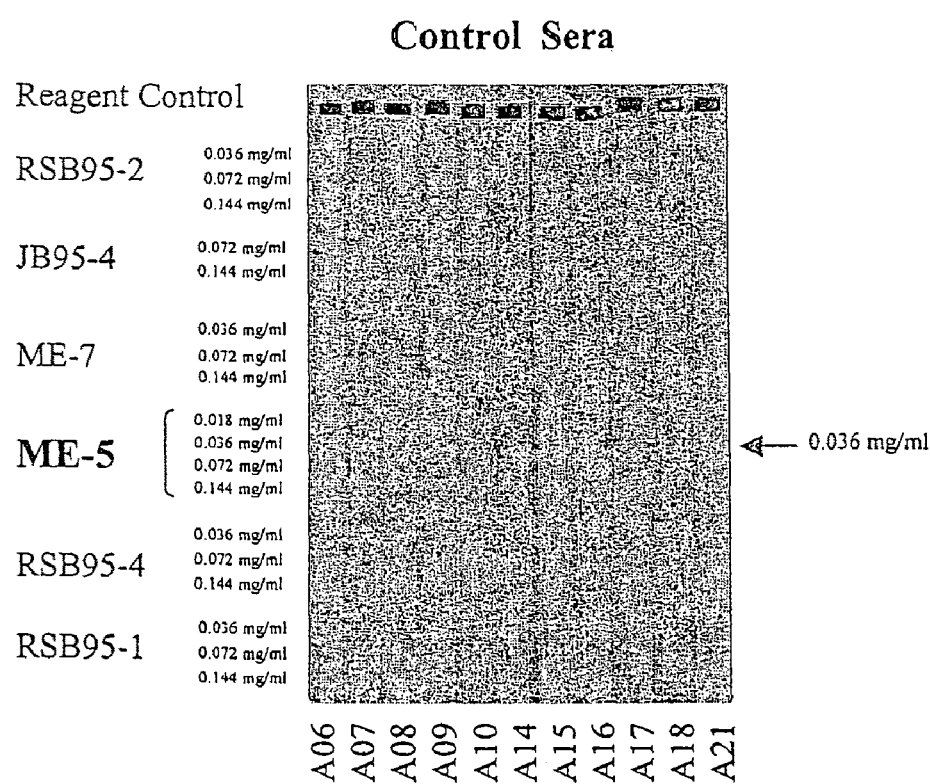

Figure 15B. Reactivity of endometriosis patient sera with recombinant ME-5 antigen on line blots.
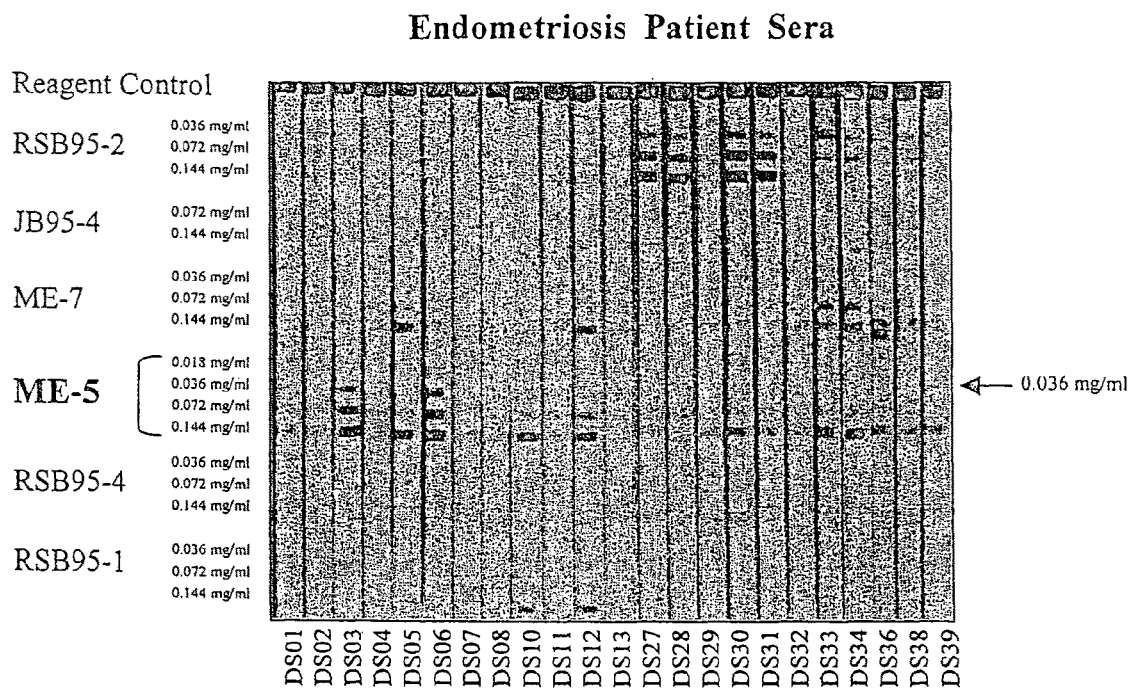

Figure 16A. Reactivity of control sera with recombinant ME-2 on line blots.
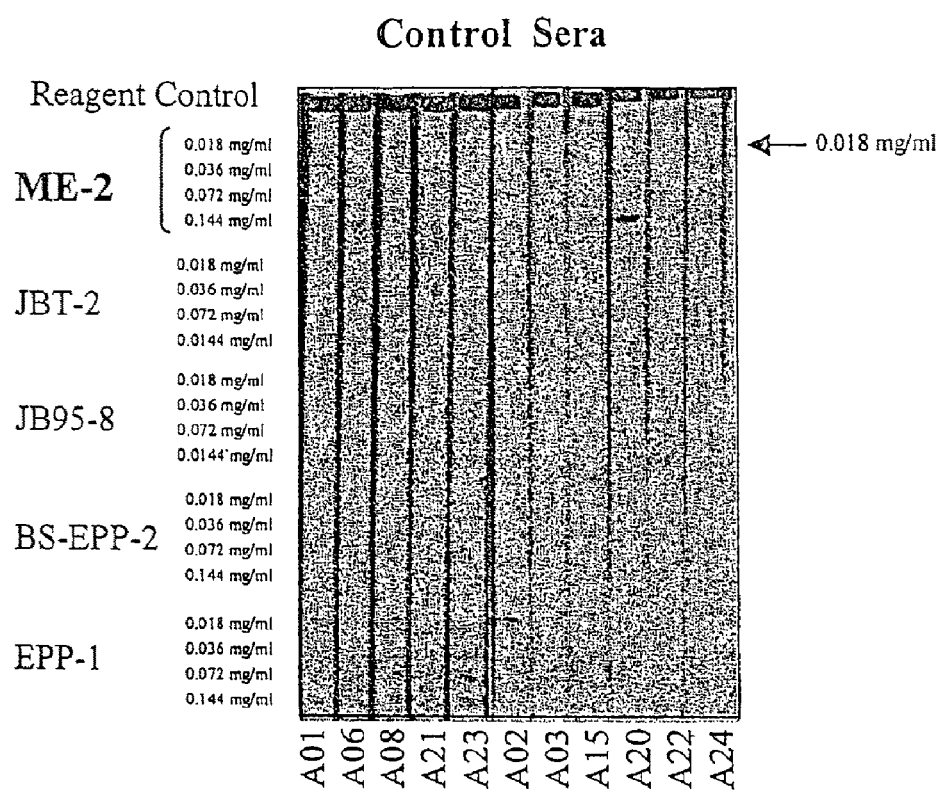

Figure 16B. Reactivity of endometriosis patients sera with recombinant ME-2 on line blots.
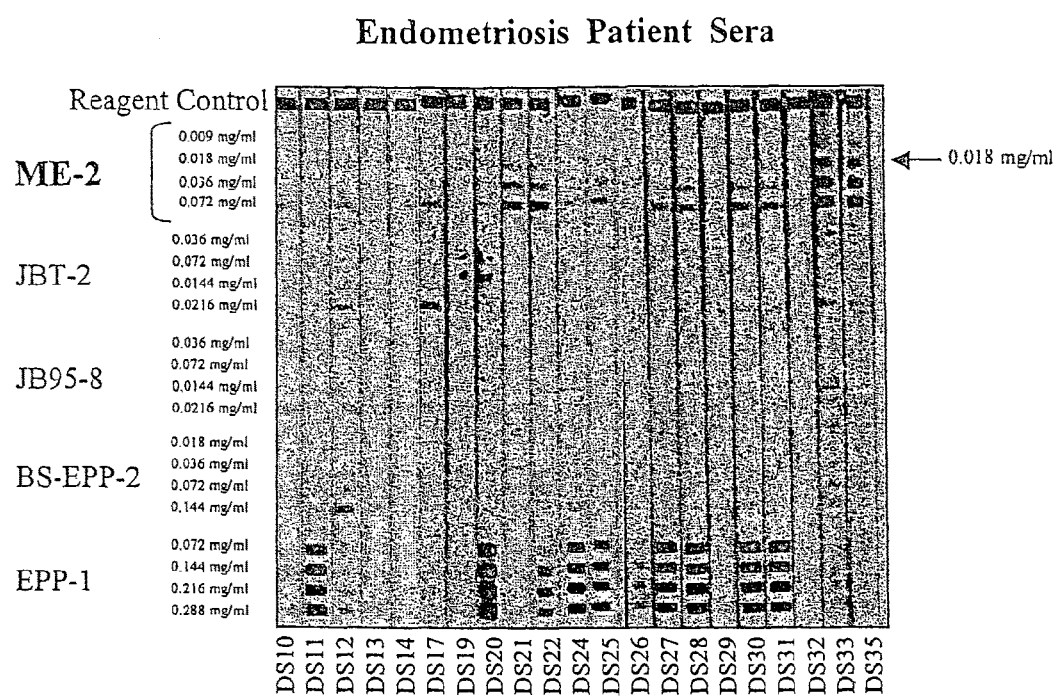

Figure 17A. Reactivity of control sera with recombinant EPP-2 on line blots.
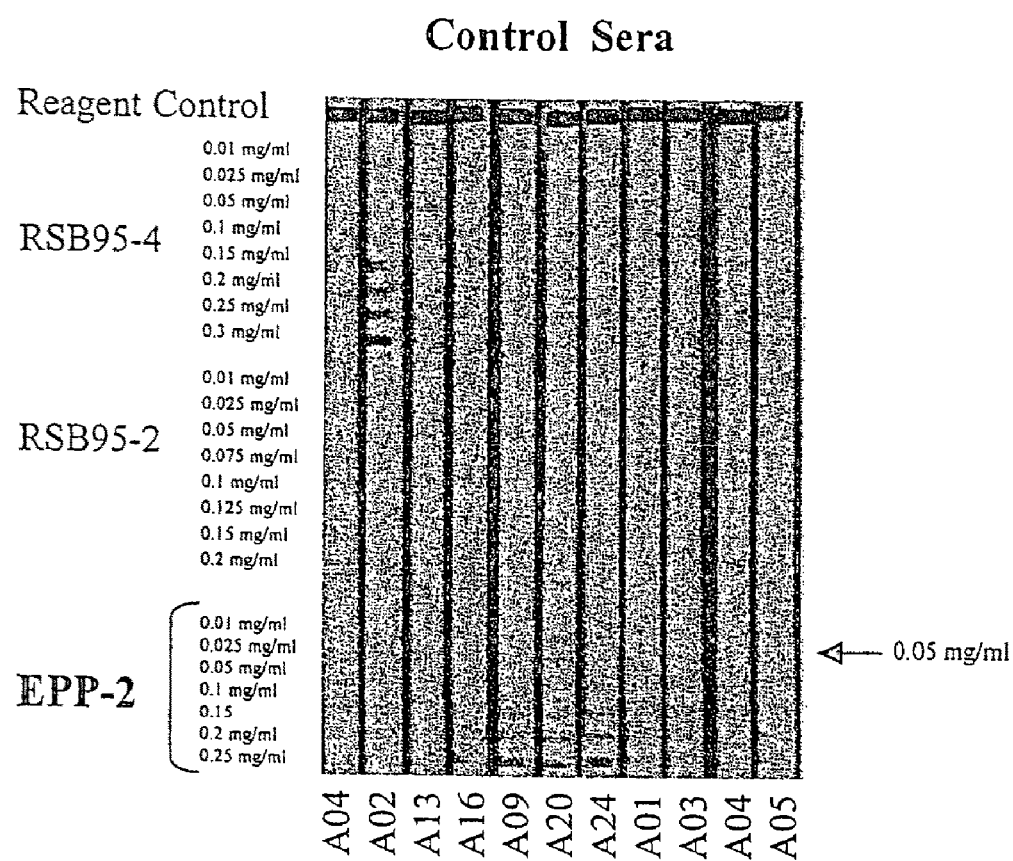

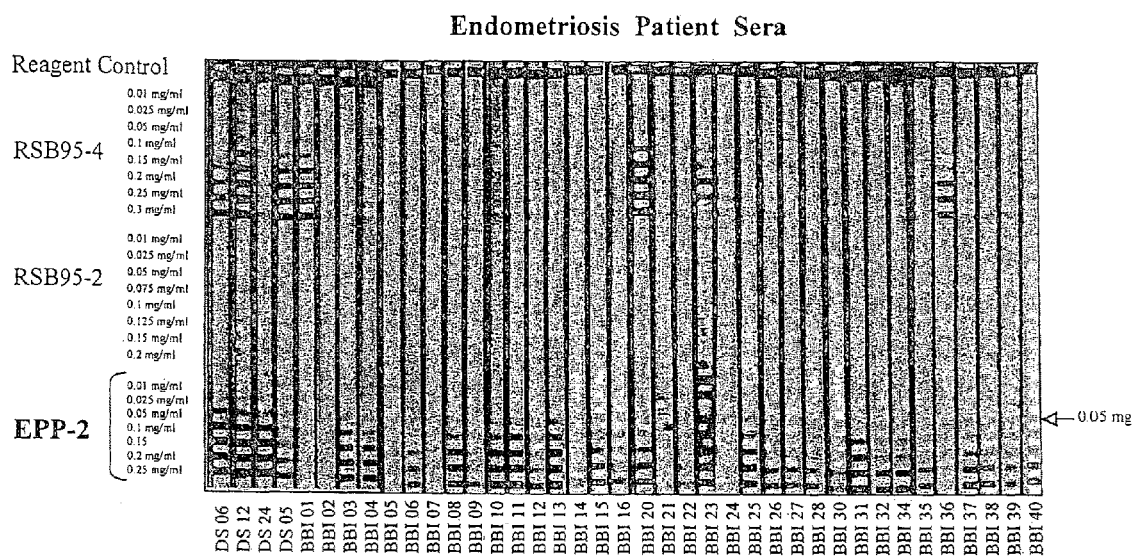
Figure 17B. Reactivity of endometriosis patient sera with recombinant EPP-2 on line blots.

METHOD FOR THE DETECTION OF ENDOMETRIOSIS USING AN ME-2 ANTIGEN

This is continuation of application Ser. No. 11/593,975 filed Nov. 6, 2006 now abandoned which is a divisional of application Ser. No. 10/887,540 filed Jul. 7, 2004, abandoned; the disclosures of which are incorporated herein by reference.

INCORPORATION BY REFERENCE OF MATERIAL SUBMITTED ELECTRONICALLY

The entire content of a Sequence Listing titled "Sequence Listing 107-226DC.txt", created on Feb. 18, 2011 and having a size of 15.3 kilobytes, which is being submitted electronically in connection with the present application, is incorporated by reference herein in its entirety.

BACKGROUND OF THE INVENTION

Endometriosis is a female reproductive disorder characterized by the presence of endometrial tissue outside of the normal uterine location. Most frequently the endometriosis tissue is present in the peritoneal cavity, attaching to various tissues and organs in this location. Endometriosis is a benign disease affecting approximately 5 million women in the United States annually with a prevalence of 10 to 15 percent in women of childbearing age. The incidence increases to 60 to 80 percent of women who are infertile or present with pelvic pain (D. Gosselin et al. [1999] Curr. Opin. Onco. Endo. & Metabol. Invest. Drugs 1:31). The conditions that predispose an individual to endometriosis are still unknown. Several authoritative reports suggest that retrograde menstruation may be a key-contributing factor, but this process is thought to be common in most women. This theory has also been questioned recently (D. B. Redwine [2002] Fert. Steril. 78:686) due primarily to the substantial differences that occur between normal or eutopic endometrium and the ectopic tissue found in diseased patients. Consequently, other genetic as well as immunological factors are thought to contribute key roles to the development of the disease in susceptible women. For example, endometriosis is thought to be much more frequent in first degree relatives of affected women when compared to the rest of the population (Coxhead and Thomas [1993] J. Obstet. Gynacol. 13:42). In addition to the frequency, the disease has also been reported to be more severe in women with a first-degree relative with endometriosis (Thomas and Campbell [2000] Gynacol. Obstet. Invest. 50:2). The precise gene(s) involved in the disorder are unknown but the pattern is strongly suspected to be maternal in nature.

Although not life threatening, endometriosis results in substantial abdominal discomfort, and may cause infertility. In fact, such symptoms can be indicative of other feminine health disorders and this makes the diagnosis of endometriosis clinically challenging. This was emphasized in a recent study upon the effects of delayed diagnosis of endometriosis (G. K. Husby et al [2003] Acta. Obstet. Gynecol. Scand. 82:649). These investigators reported delays from 3 to 11 years between the onset of pain and the final diagnosis of endometriosis. In this study women reporting both infertility and pain did not have a significantly shorter delay in diagnosis. Obviously such delays coupled with the symptoms reported lead to the expenditure of considerable economic and psychological resources.

Currently surgical laparoscopy is considered to be the gold standard for diagnosis of endometriosis. During laparoscopy the disease is visually staged using a point system from stage I (minimal disease, 1 to 5 points) to IV (severe disease, >40 points). The points are assigned according to several parameters such as location, size, and depth (superficial versus deep) of the lesions (T. P. Canavan and L. Radosh [2000] Postgrad. Med. 107:213). Some opinions reveal potential hazards with the procedure, and frequently laparoscopy does not result in a definitive diagnosis of the disease (S. Pillai et al. [1996] Am. J. Reprod. Immunol. 35:483). For example, while laparoscopy is not classed as major surgery it still has several features (invasive, expensive, requires anesthesia, and full operating facilities) which together make the process an unfortunate choice for diagnosis at least. In fact, while endometriosis is not a fatal disorder, laparoscopy itself can be life threatening. The trans-abdominal approach has been reported to be responsible for 50% of the complications from this procedure, and injury to major blood vessels can result in mortality of 15% (I. A. Brosens and J. J. Brosens [2000] Eur. J. Obstet. Gynecol. Reprod. Biol. 88:117). Other complaints are that the visual staging of the disease does not correlate with the degree of infertility or the severity or number of symptoms (T. P. Canavan and L. Radosh [2000] Postgrad. Med. 107:213). It has been reported that the place of laparoscopy in the diagnosis of endometriosis should be reassessed (I. A. Brosens and J. J. Brosens [2000] Eur. J. Obstet. Gynecol. Reprod. Biol. 88:117). Rational for this lies in part due to the suggestion by some (P. R. Koninckx [1994] Hum. Reprod. 9:2202) that mild endometriosis is not a disease at all and that all women have endometriosis. Moreover as noted above there are functional aspects (e.g., infertility, abdominal pain, etc.) to stages other than mild disease and these are more commonly being applied to diagnosis. Consequently it has been proposed that the traditional 'gold standard' be replaced with a combination of transvaginal hydrolaparoscopy (THL, a somewhat milder procedure) and magnetic resonance (MR) imaging until suitable biochemical markers have been identified (I. A. Brosens and J. J. Brosens [2000] Eur. J. Obstet. Gynecol. Reprod. Biol. 88:117).

The frequency of endometriosis and the difficulty of diagnosing the disorder together represent ample rationale for experiments designed to identify these serum based biochemical markers. Other discovery phase programs have implied that of potential markers of endometrial disease may exist. For example, levels of the epithelial ovarian-derived antigen CA-125 have been reported to be elevated in serum, peritoneal fluid, and menstrual fluid of endometriosis patients (B. Mol et al. [1998] Fertil. Steril. 70:1101). The marker exhibited good specificity, but the sensitivity is poor with high levels present in patients afflicted with PID, ovarian cancer, or cervical carcinoma. Despite the limitations, the marker may be of use for patients who are likely to have the disease for faster orientation toward laparoscopy, since CA-125 levels do correlate somewhat with the degree of disease and response to treatment (T. P. Canavan and L. Radosh [2000] Postgrad. Med. 107:213).

Also, Sharpe-Timms et al. (Biol. Reprod. [1998] 58:988) have reported that endometriosis lesions secrete a haptoglobin-like protein in a rodent model system. The haptoglobulin was specifically synthesized by endometriosis tissue and was not found in uterine tissue using a sensitive reverse transcriptase PCR technique. This antigen is also interesting in that it has been reported to modulate immune cell functions and could contribute to the pathophysiology of endometriosis Along slightly different lines, D. Gosselin et al. (Curr. Opin. Oncol. Endo. Metabol. Inv. Drugs [1999] 1:31) reported a diagnostic algorithm employing several different combinations of leukocyte markers present upon subsets of T and B cells, macrophages, and NK cells in peripheral blood and endometrium of patients with endometriosis. This formed the foundation for the development of a diagnostic test (Metrio Test) by PROCREA BioSciences, Inc. which is approved by Health Canada. The Metrio Test is based on the assessment of eight proprietary leukocyte subsets by flow cytometry analysis combined with a blood biochemical marker evaluated by ELISA (J. Brosens et al. Obstet. Gynecol. Clin. North Am. [2003] 30:95-114). This test reportedly has a specificity rate of 95% and a sensitivity rate of 61%.

P. Vigano et al. (Obstet. Gynecol. [2000] 95:115-118) report that the soluble form of intercellular adhesion molecule 1 is released by uterine endometrium and such release correlates with the extent (number of implants) of endometriosis in patients. The authors suggest that soluble intercellular adhesion molecule 1 might be of value in evaluating the spread potential of refluxed endometrium. However, soluble intercellular adhesion molecule 1 is also known to be released in other disease states so the potential value of this protein as a marker may be diminished somewhat.

J. Mahnke et al. (Fertil. Sterl. [2000] 73:166-170) evaluated VEGF and IL-6 levels in peritoneal fluid of women with endometriosis and found them to be elevated in patients with advanced disease. The levels of VEGF and IL-6 were lower in normal women and patients with milder disease. Nevertheless, the diagnostic value of these markers is suspect since at least VEGF is known to be a potent angiogenesis factor that is regulated by hypoxia in normal endometrium (A. M. Sharkey et al. J. Clin. Endocrinol. Metab. [2000] 85:402-409).

Matalliotakis and coworkers (Obstet. Gynecol. [2000] 95:810-813) found elevated levels of soluble CD23 in serum of women with endometriosis when compared to a control population. The CD23 levels decreased significantly during treatment with either danazol or leuprolide acetate. There seemed to be no correlation between soluble CD23 levels and the severity of endometriosis in the patients. As noted above for some of the other putative markers, CD23 has been associated with conditions linked to autoantibody production and levels of this protein are elevated in patients with autoimmune diseases.

Overall despite the substantial effort extended by numerous researchers, and also as reported in the publications reviewed above, no truly acceptable marker for endometriosis has been discovered. Yet, the physical and economic impact of the disease, and the difficulty in diagnosing the disorder dictate that the search for suitable markers be continued. Consequently, the activities disclosed in this invention were undertaken to identify markers of endometriosis that can aid physicians in monitoring patients with this illness. Other groups have performed such projects and these discoveries are the subject of numerous patent documents, which differ substantially from the discovery of the ME-5, ME-2 and EPP2 markers described in this invention. In U.S. Patent application 2003/0032044 there is a description of methods for generally detecting reproductive tract disorders by measuring the levels of interleukins IL-13 and IL-15 in specimens. Another U.S. Patent application 2002/0192647 proposes a process for diagnosing angiogenic diseases by measuring a single nucleotide polymorphism in the VEGFR-1 gene. Endometriosis is categorized as one of this group of angiogenic diseases, but it was not the subject of any of the claims. Patent applications 2001/046713 and 2001/044158 describe a method for diagnosis of endometriosis by detecting anti-Tomsen-Frienenreich antibodies in specimens. An issued U.S. Pat. No. 6,376,201 illustrates the use of major histocompatibility complex-class I antigens in diagnosing endometriosis and forming the basis of the Metrio Test as described above. In this patent the MHC-class I antigens are detected in specimens with specific monoclonal antibodies and similar disclosures were described in U.S. Pat. No. 5,618,680 and W.O. 0043789. A method for diagnosing endometriosis is described in U.S. Pat. No. 6,540,980 that involves measurement of eosinophil peroxidase levels. In U.S. Pat. No. 6,525,187 is described an apparently novel, marker of endometriosis which is the target of autoantibodies present in patient serum. Another method for diagnosis of endometriosis is disclosed in U.S. Pat. No. 6,387,629 and this is based upon the measurement of the protease cathepsin S in a clinical sample. A gene encoding an endometrial bleeding associated factor (ebaf) is described in U.S. Pat. No. 6,294,662 and this gene could be useful for diagnosis of endometriosis. However the ebaf gene seems to have better utility in the early diagnosis of selected carcinomas (colon, ovaries, or testis) in a human. In U.S. Pat. No. 5,877,284 another potential marker of endometriosis is described. This marker is a small soluble protein isolated by affinity chromatography from the peritoneal fluid of women with endometriosis, and the protein has chemotactic activity to neutrophils and macrophages. A process for monitoring human endometrial functions is described in U.S. Pat. No. 4,489,166 and it involves the quantitative measurement of progestagen-associated endometrial protein (PEP) in a clinical sample. European Patent No. 1191107 describes a method for diagnosis of endometriosis by measuring a reduction in the levels of one of a group of 15 different human genes. An immunoassay process is described in European Patent No. 0387027 which establishes endometriosis in a patient by evaluating a specimen with an anti-endometriosis monoclonal antibody. A method is described in W.O. 0063675 for diagnosis of endometriosis by measuring increased levels of endometriosis factor in biological fluids of a patient. W.O. 9963116 provides for a method of diagnosing endometriosis by measuring increases in the amount of prothymosin in endometriotic tissue.

U.S. Pat. No. 6,531,277 discloses an endometriosis-specific secretory protein. The document characterized and disclosed human ENDO-1 that is produced by stromal cells of endometriotic tissue. The ENDO-1 protein is 40 to 50 kilodaltons in molecular weight and has an isoelectric point of 4.0 to 5.5. The claims of the document are concerned primarily with a molecular diagnostic assay measuring differences in expression of ENDO-1 mRNA in endometriosis tissue samples. In a related application U.S. 2002/0009718 the invention is extended for measurement of the ENDO-1 glycoprotein in patient samples using immunoassay to establish the presence of endometriosis. Nevertheless, the characteristics of ENDO-1 presented in these documents suggest that it is considerably different from the markers described in the present invention. For example when measured by SDS PAGE and Western blotting the ME-5, ME-2, and EPP2 proteins are about 38, 49, and 9 kilodaltons in size, respectively. Only the ME-2 marker is within the range specified for ENDO-1, but ME-2 has an isoelectric point of 8.8 so it is not a related protein. Also, the isoelectric points of the ME-5 and EPP2 antigens are calculated at 5.7 and 12.5, respectively, which are also well above the range of values specified for the ENDO-1 protein. Moreover the ENDO-1 marker is a member of the haptogloblin family of proteins, but nucleic acid and amino acid sequence comparisons show that the ME-5, ME-2, and EPP2 markers are not related to this family of proteins.

In yet another separate disclosure, U.S. Pat. No. 5,843,673 specifies a method of screening for endometriosis in women by measuring a reduction in the amounts of a 28 to 32 kilodalton molecular weight glycoprotein in peritoneal fluid or serum samples. The protein possesses an isoelectric point of 7.0 to 9.0 and is secreted specifically by stromal cells of endometriotic origin. The glycoprotein disclosed in the document is related to tissue inhibitor of metaloproteinases-1 (TIMP-1) by virtue of amino acid sequence identity measured in the amino terminal region of protein. In the patent it is shown that endometriosis is indicated in a patient who has reduced levels of TIMP-1 present in serum or peritoneal fluid. The ME-5, ME-2, and EPP2 proteins of this invention are not related to TIMP-1 and they have no measurable protein or nucleic acid homology to this family of proteins. In addition, and as noted above, the biochemical properties of the ME-5, ME-2, and EPP2 proteins differ from those of TIMP-1 and each is considerably larger or smaller (at 38, 49, or 9 kilodaltons, respectively) than the range given for TIMP-1. While the isoelectric point of ME-2 is at the upper range of that of TIMP-1, the isoelectric point of ME-5 is 5.7 and EPP2 is 12.5 which are much different.

Another disclosure of protein agents implicated in endometriosis is contained in the document WO 01/32920 in which it is assumed that a total of 33 genes and their protein products are associated with the disease. These putative endometriosis markers were identified by comparing the pattern of gene expression in diseased endometrial relative to that of normal tissue. This differential display reverse transcriptase polymerase chain reaction employed in the document is a purely genetic screening approach designed to identify disease-associated genes based upon differences in the expression levels of mRNAs. The mRNA populations compared are usually normal healthy endometrium and the diseased counterpart, ideally both isolated from a single patient suffering from the illness. This technology ignores the functional activity of the proteins encoded by the mRNAs, and does not interrogate specimens based on disease hallmarks, symptoms, or the body's response to the illness. The latter strategies are arguably better approaches for marker discovery as discussed below. The individual nucleic acid sequences identified in the document fall into the general groups of; protease or protease inhibitor, tumor suppressor protein, immune system proteins, inflammatory response proteins, enzymes, lipid binding proteins, transcription factors, and matrix or cell adhesion molecules. All of the genes in WO 01/32920 are known and the nucleic acid sequences appear in the public databases allowing them to be identified. The individual nucleic acid sequences identified and implicated as somehow being involved in endometriosis are: cathepsin D, AEBP-1, stromelysin-3, cystatin B, protease inhibitor 1, sFRP4, gelsolin, IGFBP-3, dual specificity phosphatase 1, PAEP, immunoglobulin A chain, ferritin, complement component 3, pro-alpha-1 type III collagen, proline 4-hydroxylase, alpha-2 type I collagen, claudin-4, melanoma adhesion protein, procollagen C-endopeptidase enhancer, nascent-polypeptide-associated complex alpha polypeptide, elongation factor 1 alpha (EF-1α), vitamin D3 25 hydroxylase, CSRP-1, steroidogenic acute regulatory protein, apolipoprotein E, transcobalamin II, prosaposin, early growth response 1 (EGR1), ribosomal protein S6, adenosine deaminase RNA-specific protein, RAD21, guanine nucleotide binding protein beta polypeptide 2-like 1 (RACK1), and podocalyxin (and see references within WO 01/32920). Overall the diagnosis of endometriosis with the above agents would involve assessing the level of expression of the gene. The ME-5, ME-2, and EPP2 proteins and the nucleic acids described in this invention are also known and appear in the databases (see Example 1, below). However, none of the ME-5, ME-2, or EPP2 sequences fall into any of the groups listed above nor do they correspond to any of the designated agents either by computer-assisted homology comparison or predicted function based upon the presence of recognizable motifs present in the protein sequence. A similar gene expression-based strategy was employed in the discoveries documented by S. Baban et al. in US Patent Application 2002/0127555 in which 14 genes were found to be overexpressed in endometriosis patients relative to disease-free females. The overexpressed genes were NADH dehydrogenase, hUCCi, Paralemmin, citrate transport protein. HIF1-alpha, ARNT, Glut-1, MnSOD, GPx, ATP synthase, c-jun, Cx43, HSP 70, and cox2. In addition, 19 genes were reported in this document to be underexpressed in endometriosis patients relative to disease-free females. The genes underexpressed in diseased endometrial tissues were Cap43, RNA helicase, CO3, FKHR, AK3, catalase, GST, eNOS, 12S rRNA, T1227H, CO2, aconitase, ANT-1, Bcl-2, COUP-TF, IL-1 beta, HSP 90, GPx4, and GRP78. Yet another gene expression strategy was described by H. Hess-Stumpp et al. In US Patent Application 2003/0077589 resulting in the discovery of 15 genes that are overexpressed in endometriosis. The overexpressed genes were fibronectin, IGFBP-2, transmembrane receptor PTK7, platelet-derived growth factor alpha, collagen type XVIII alpha 1, subtilisin-like protein (PACE4), laminin M chain (merosin), elastin, collagen type IV alpha 2, p27 interferon alpha-inducible gene, reticulocalbin, aldehyde dehydrogenase 6, gravin, nidogen, and phospholipase C epsilon. Again, as stated above, the ME-5, ME-2, and EPP2 protein and nucleic acid sequences are not related to any of the genes described in the latter two patents.

Taken together and comparing the results of these three documents, it is interesting that all of them used similar but not identical gene expression strategies to identify a total of 62 genes which are overexpressed in endometriosis and 19 genes that are underexpressed. The implication is therefore that the 81 described genes are related to or involved in endometrial disease. Surprisingly, among these three independent studies, no single human gene or class of genes was consistently found to be associated with endometriosis. Ostensibly if a gene were overexpressed because of changes occurring in endometriosis tissue relative to the normal counterpart, then it would be expected to reproducibly be identified in all studies that assess the gene expression profile of diseased tissue. This does not seem to occur in the otherwise well-designed projects, and brings into question strategies for marker discovery based only on gene expression profiling technologies.

The document WO 94/28021 describes endometrial proteins, antigenic compounds, and methods of detecting endometriosis. The disclosure encompasses endometriosis-specific proteins defined by molecular weight and isoelectric point. Many of the claims presented are based only on size, but others specify a molecular weight and isoelectric point. The principal endometriosis antigen of the document and which is described in the initial claim has a molecular weight of 64 kilodaltons and an isoelectric point of 3.5. The antigen is used to measure antibodies in specimens obtained from endometriosis patients and also can itself be measured directly for its presence in patient samples. In addition, a larger molecular weight endometriosis protein of 94 kilodaltons with an isoelectric point of 3.5 is also described presumably to be used in the same formats as the smaller antigen. The document also claims nucleic acids for these proteins, however these sequences do not appear in enough detail to allow for comparison to the ME-5, ME-2, and EPP2 protein and nucleic acids of this invention. A small amount of amino acid sequence is presented in WO 94/28021, but there are only 17 residues shown in the document and of these over half are ambiguous. Although similar applications are envisioned for the ME-5, ME-2, and EPP2 protein described in this invention, the antigens described above do not compare in any reported properties to those of the three endometriosis antigens presented here. Initially, none of the unambiguous residues of amino terminal protein sequence are present in the corresponding regions of ME-5, ME-2, and EPP2. In addition, the ME-5, ME-2, and EPP2 proteins are 38, 49, and 9 kilodaltons in size, which are considerably smaller than the antigens described in the document outlined above. Moreover the isoelectric points of ME-5, ME-2, and EPP2 are 5.7, 8.8, and 12.5 which are considerably greater than described for the other proteins. It must be concluded that the endometrial ME-5, ME-2, and EPP2 antigens of this invention have little in common with the proteins described in WO 94/28021.

Methods and reagents for diagnosis of endometriosis are described in NZ 232801 (also application EP-A-0 387 027) essentially by measuring an endometriosis antigen in a patient specimen using an anti-endometriosis antibody. Various antigens are described in the document ranging in molecular weight from 50 to 173 kilodaltons but no additional characterization of the proteins was performed. These proteins were isolated as a mixture from the culture medium and cytoplasm of 2774 ovarian carcinoma cells, and can be obtained from other cultured cell lines as well. Also described in the disclosure is an anti-endometrial antibody, which is a human IgM monoclonal originally isolated because it reacted with ovarian cancer-associated antigens. Isolation of the antibody was apparently through a set of activities that were unrelated to endometriosis and the ovarian cancer antigen targets apparently were not well characterized. The antibody was made by fusion of patient lymphocytes with a heteromyeloma, and apparently the reactivity of the monoclonal with endometrial antigens was discovered subsequently. Regardless, based on the criteria presented it is unlikely that any of the proteins of NZ 232801 are the same as the smaller ME-5, ME-2, and EPP2 proteins of this invention.

Another series of endometrial antigens reactive with anti-endometrial antibodies is described in WO 92/18535 and these are also characterized by molecular weight on SDS PAGE analysis. The described protein antigen fragments were isolated from the cytoplasm of epithelial adenocarcinoma cells and are described as useful for detection of endometrial antibodies which are indicative of endometriosis. The antigens are cytoplasmic proteins with sizes of 63 to 67, 33 to 37, 40 to 44, 31 to 35, and 57 to 64 kilodaltons. The designations likely refer to a single protein species, but the size ranges were presented in the document to reflect the inherent inaccuracy (±10%) for the SDS PAGE assay method used. Apparently the preferred proteins for use are the 33 to 37, 40 to 44, and the 57 to 59 kilodalton proteins. The 33 to 37 and 40 to 44 proteins seemed to be present in most of the cell lines that were studied in the document for use as sources of antigen, while the 57 to 59 protein fragments originates from the T47D breast carcinoma cell line. The document describes the use of these proteins individually (or mixed) immobilized on solid support to measure endometrial antibodies. Of course similar applications are envisioned for the ME-5, ME-2, and EPP2 antigens, however with the exception of possibly the 33 to 37 kilodalton fragments there is little else presented in this document that compares to disclosures in WO 92/18535.

SUMMARY OF THE INVENTION

A recombinant polynucleotide comprising an isolated nucleotide sequence from SEQ ID NO:2 encoding a polypeptide epitope of at least 5 amino acids of ME-5 (SEQ ID NO:3), wherein the epitope specifically binds to antibodies from subjects diagnosed with endometriosis.

A purified, recombinant ME-5 polypeptide whose amino acid sequence is substantially identical to that of SEQ ID NO:3 or an allelic variant of SEQ ID NO:3.

A purified polypeptide comprising an epitope of at least 5 amino acids of ME-5 (SEQ ID NO:3), wherein the epitope specifically binds to antibodies from subjects diagnosed with endometriosis.

A composition consisting essentially of an antibody that specifically binds to an epitope of ME-5 polypeptide (SEQ ID NO:3).

A method for detecting a ME-5 polypeptide (SEQ ID NO:3) in a sample, comprising the steps of:
  (a) contacting the sample with an antibody that specifically binds to an epitope of the ME-5 polypeptide and
  (b) detecting specific binding between the antibody and ME-5 polypeptide;
whereby specific binding provides a detection of ME-5 polypeptide in the sample.

A method for diagnosing endometriosis in a human subject comprising the steps of:
  (a) detecting a test amount of an antibody that specifically binds to an epitope of ME-5 polypeptide (SEQ ID NO:3) in a sample from the subject; and
  (b) comparing the test amount with a normal range of the antibody in a control sample from a subject who does not suffer from endometriosis,
whereby a test amount above the normal range provides a positive indication in the diagnosis of endometriosis.

A recombinant polynucleotide comprising an isolated nucleotide sequence from SEQ ID NO:5 encoding a polypeptide epitope of at least 5 amino acids of ME-2 (SEQ ID NO:6), wherein the epitope specifically binds to antibodies from subjects diagnosed with endometriosis.

A purified, recombinant ME-2 polypeptide whose amino acid sequence is identical to that of SEQ ID NO:6 or an allelic variant of SEQ ID NO:6.

A purified polypeptide comprising an epitope of at least 5 amino acids of ME-2 (SEQ ID NO:6), wherein the epitope specifically binds to antibodies from subjects diagnosed with endometriosis.

A composition consisting essentially of an antibody that specifically binds to an epitope of ME-2 polypeptide (SEQ ID NO:6).

A method for detecting a ME-2 polypeptide (SEQ ID NO:6) in a sample, comprising the steps of:
  (a) contacting the sample with an antibody that specifically binds to an epitope of the ME-2 polypeptide and
  (b) detecting specific binding between the antibody and ME-2 polypeptide;
whereby specific binding provides a detection of ME-2 polypeptide in the sample.

A method for diagnosing endometriosis in a human subject comprising the steps of:
  (a) detecting a test amount of an antibody that specifically binds to an epitope of ME-2 polypeptide (SEQ ID NO:6) in a sample from the subject; and
  (b) comparing the test amount with a normal range of the antibody in a control sample from a subject who does not suffer from endometriosis,
whereby a test amount above the normal range provides a positive indication in the diagnosis of endometriosis.

A recombinant polynucleotide comprising an isolated nucleotide sequence from SEQ ID NO:8 encoding a polypeptide epitope of at least 5 amino acids of EPP2 (SEQ ID NO:9), wherein the epitope specifically binds to antibodies from subjects diagnosed with endometriosis.

A purified, recombinant EPP2 polypeptide whose amino acid sequence is identical to that of SEQ ID NO:9 or an allelic variant of SEQ ID NO:9.

A purified polypeptide comprising an epitope of at least 5 amino acids of EPP2 (SEQ ID NO:9), wherein the epitope specifically binds to antibodies from subjects diagnosed with endometriosis.

A composition consisting essentially of an antibody that specifically binds to an epitope of EPP2 polypeptide (SEQ ID NO:9).

A method for detecting a EPP2 polypeptide (SEQ ID NO:9) in a sample, comprising the steps of:
 (a) contacting the sample with an antibody that specifically binds to an epitope of the EPP2 polypeptide and
 (b) detecting specific binding between the antibody and EPP2 polypeptide;
whereby specific binding provides a detection of EPP2 polypeptide in the sample.

A method for diagnosing endometriosis in a human subject comprising the steps of:
 (a) detecting a test amount of an antibody that specifically binds to an epitope of EPP2 polypeptide (SEQ ID NO:9) in a sample from the subject; and
 (b) comparing the test amount with a normal range of the antibody in a control sample from a subject who does not suffer from endometriosis, whereby a test amount above the normal range provides a positive indication in the diagnosis of endometriosis.

A composition containing at least one of
 a purified, recombinant ME-5 polypeptide whose amino acid sequence is substantially identical to that of SEQ ID NO:3 or an allelic variant of SEQ ID NO:3;
 a purified, recombinant ME-2 polypeptide whose amino acid sequence is substantially identical to that of SEQ ID NO:6 or an allelic variant of SEQ ID NO:6; and
 a purified, recombinant EPP2 polypeptide whose amino acid sequence is substantially identical to that of SEQ ID NO:9 or an allelic variant of SEQ ID NO:9.

A composition containing at least one of
 a purified polypeptide comprising an epitope of at least 5 amino acids of ME-5 (SEQ ID NO:3);
 a purified polypeptide comprising an epitope of at least 5 amino acids of ME-2 (SEQ ID NO:6), and
 a purified polypeptide comprising an epitope of at least 5 amino acids of EPP2 (SEC) ID NO:9),
wherein said epitopes specifically bind to antibodies from subjects diagnosed with endometriosis.

A method for diagnosing endometriosis in a human subject comprising the steps of:
 (a) detecting a test amount of an antibody that specifically binds to at least one of ME-5 (SEQ ID NO:3) polypeptide, ME-2 (SEQ ID NO:6) polypeptide; and EPP2 (SEQ ID NO:9) polypeptide in a sample from the subject; and
 (b) comparing the test amount with a normal range of the antibody in a control sample from a subject who does not suffer from endometriosis,
whereby a test amount above the normal range provides a positive indication in the diagnosis of endometriosis.

As shown in the documents cited above, a number of discoveries have been documented for candidate markers of endometriosis. None of those correspond to the ME-5, ME-2, or EPP2 proteins and nucleic acid sequences of the present invention. Consequently the ME-5, ME-2, and EPP2 proteins of this invention represent novel new markers for endometriosis and the targets of anti-endometrial antibodies produced by women suffering from the disorder. The discovery of the ME-5, ME-2, and EPP2 markers of this invention was predicated upon the knowledge that women suffering from endometriosis have defects in their immune systems. It is assumed that some immune system problems may be manifest in the presence of autoantibodies directed towards endometrial antigens. Others (S. Pillai et al. [1998] Am. J. Reprod. Immunol. 39:235; Van Voorhis and Stovall [1997] J. Reprod. Immunol. 33:239) have discussed such a situation. Clearly, this represents an attractive means of identifying candidate markers of the disease and as useful tools for monitoring patients with endometriosis. Recently, a summary of the accuracy of serum markers for the diagnosis of endometriosis showed endometrial antibodies to be among the best markers with sensitivity of 74% to 83% and specificity of 79% to 100% (J. Brosens et al. 2003] Obstet. Gynecol. Clin. North Am. 30:95). However the antibodies were not measured against discrete isolated antigens such as ME-5, ME-2, and EPP2 for example.

In initiating a program to identify antigens that may be useful markers of endometriosis (and thus helpful in monitoring women that suffer the disorder) some assumptions were made regarding this disease. First, as noted above, it was assumed that immune system defects occur in these women which enable them to make antibodies directed towards specific endometrial antigens. Second these serum antibodies could be used as tools to identify the antigens, and these proteins in part would form the foundation of immunodiagnostic test systems for monitoring patients with the disorder. The strategy for identification of endometriosis markers was to use patient serum to immunoscreen an endometrial tissue cDNA expression library. Candidate clones would be completely characterized for development of an immunoassay suitable for monitoring patients in a clinical environment.

DETAILED DESCRIPTION OF THE PREFERRED EMBODIMENTS

A total of three endometrial proteins are described that react with antibodies present in the serum of endometriosis patients. The ME-5 endometriosis marker is specified by a mRNA of about 1.4 kb, of which 1,302 nucleotides is disclosed in this invention. The protein predicted from this sequence is 303 amino acids in size and has a calculated molecular weight of about 35,000 daltons. The natural protein product has a molecular weight of about 38 kD as measured by Western blot with a specific monoclonal antibody. The protein was particularly abundant in ovary tissue which, taken with the isolation from endometrial tissue is strongly supportive of its presence in reproductive tissues and as a marker of reproductive disease. In immunoblotting experiments with immobilized recombinant ME-5 antigen, a number of endometriosis patients were evaluated and the signals generated were considerably stronger than that obtained with a number of control patients.

The ME-2 endometriosis marker is specified by a mRNA of about 2.0 kb of which 1,353 nucleotides is disclosed in this invention. The protein predicted from this sequence is 393 amino acids in size and has a calculated molecular weight of about 45,000 Daltons. In immunoblotting experiments with immobilized recombinant ME-2 antigen evaluated with a number of endometriosis patients the signal generated was considerably stronger than that obtained with a number of control patients.

The EPP2 endometriosis marker is specified by a mRNA of about 1.0 kb of which 891 nucleotides is disclosed in this invention. The protein predicted from this sequence is 99 amino acids in size and has a calculated molecular weight of about 9,300 Daltons. In immunoblotting experiments with immobilized recombinant EPP2 antigen evaluated with a number of endometriosis patients the signal generated was considerably stronger than that obtained with a number of control patients.

Details of these and other issues related to the ME-5, ME-2, and EPP2 endometriosis markers and their nucleic acids are contained in the examples below.

Clearly as cited by the documents presented above, a number of discoveries have been documented for candidate markers of endometriosis. None of those correspond to the ME-5, ME-2, or EPP2 proteins and nucleic acid sequences disclosed herein. Consequently the ME-5, ME-2, and EPP2 proteins of this invention represent novel new markers for endometriosis and the targets of anti-endometrial antibodies produced by women suffering from the disorder. The discovery of the ME-5, ME-2, and EPP2 markers in this invention was predicated upon the knowledge that women suffering from endometriosis have defects in their immune systems. It is assumed that some immune system problems may be manifest in the presence of autoantibodies directed towards endometrial antigens. Others (S. Pillai et al. [1998] Am. J. Reprod. Immunol. 39:235; Van Voorhis and Stovall [1997] J. Reprod. Immunol. 33:239) have discussed such a situation. Clearly, this represents an attractive means of identifying candidate markers of the disease and as Useful tools for monitoring patients with endometriosis. Recently, a summary of the accuracy of serum markers for the diagnosis of endometriosis showed endometrial antibodies to be among the best markers with sensitivity of 74% to 83% and specificity of 79% to 100% (J. Brosens et al. 2003] Obstet. Gynecol. Clin. North Am. 30:95). However the antibodies were not measured against discrete isolated antigens such as ME-5, ME-2, and EPP2 for example.

In initiating a program to identify antigens that may be useful markers of endometriosis (and thus helpful in monitoring women that suffer the disorder) some assumptions were made regarding this disease. First, as noted above, it was assumed that immune system defects occur in these women which enable them to make antibodies directed towards specific endometrial antigens. Second these serum antibodies could be used as tools to identify the antigens, and these proteins in part would form the foundation of immunodiagnostic test systems for monitoring patients with the disorder. The strategy for identification of endometriosis markers was to use patient serum to immunoscreen an endometrial tissue cDNA expression library. Candidate clones would be completely characterized for development of an immunoassay suitable for monitoring patients in a clinical environment.

DESCRIPTION OF THE DRAWINGS

FIGS. 1A, 1B, and 1C show the nucleotide sequence (SEQ ID NO:1) for the isolated ME-5 cDNA, the nucleotide sequence of the coding region (SEQ ID NO:2) of this ME-5cDNA, and the deduced amino acid sequence (SEQ ID NO:3) of the protein encoded by the nucleotide sequence of the ME-5 cDNA. In FIG. 1A there is a 112 base pair 5' untranslated sequence upstream of the predicted ATG start codon. Also in FIG. 1A is a 254 base pair 3' untranslated region downstream of the TGA stop codon. The 3' untranslated region terminates at a stretch of dT corresponding to the poly A tail of the mRNA. The start Codon (ATG) and the translation stop codon (TGA) are presented in bold type in the cDNA sequence of FIGS. 1A and B.

FIGS. 2A, 2B, and 2C show the nucleotide sequence (SEQ ID NO:4) for the isolated ME-2 cDNA, the nucleotide sequence of the coding region (SEQ ID NO:5) of this ME-2 cDNA, and the deduced amino acid sequence (SEQ ID NO:6) of the protein encoded by the nucleotide sequence of the ME-2 cDNA. In FIG. 2A there is a 54 base pair 5' untranslated sequence upstream of the predicted ATG start codon. Also in FIG. 2A is a 95 base pair 3' untranslated region downstream of the TAG stop codon. The 3' untranslated region terminates at a stretch of dT corresponding to the poly A tail of the mRNA. The start codon (ATG) and the translation stop codon (TAG) are presented in bold type in the cDNA sequence of FIGS. 2A and B.

FIGS. 3A, 3B, and 3C show the nucleotide sequence (SEQ ID NO:7) for the isolated EPP2 cDNA, the nucleotide sequence of the coding region (SEQ ID NO:8) of this EPP2 cDNA, and the deduced amino acid sequence (SEQ ID NO:9) of the protein encoded by the nucleotide sequence of the EPP2 cDNA. In FIG. 3A there is a 45 base pair 5' untranslated sequence upstream of the predicted ATG start codon. Also in FIG. 3A is a 522 base pair 3' untranslated region downstream of the TAA stop codon. The 3' untranslated region terminates at a stretch of dT corresponding to the poly A tail of the mRNA. The start codon (ATG) and the translation stop codon (TAA) are presented in bold type in the cDNA sequence of FIGS. 3A and B.

FIG. 4 demonstrates the pattern of ME-5 mRNA expression in various human tissues. A commercial Northern blot (BD Biosciences; San Diego, Calif.) was hybridized with the complete $^{32}$P-labeled ME-5 coding sequence of FIG. 1B. Conditions of hybridization and washing were as described by the manufacturer. Hybridizing bands were observed corresponding to a mRNA of about 1,400 nucleotides (migrates just slower than the 1,350 nucleotide marker) as well as another larger but perhaps less abundant message of 1,800 to 2,000 nucleotides (migrating just ahead of the 2,400 nucleotide marker). The ME-5 sequence seems to be expressed most abundantly in prostate, testis and uterus tissues, but lower amounts were detected in the other tissues evaluated (spleen, thymus, small intestine, colon and peripheral blood leukocyte).

FIG. 5 demonstrates the pattern of ME-2 mRNA expression in various human tissues. A commercial Northern blot (BD Biosciences; San Diego, Calif.) was hybridized with the complete $^{32}$P-labeled ME-2 coding sequence of FIG. 2B. Conditions of hybridization and washing were as described by the manufacturer. Hybridizing bands were observed corresponding to a mRNA of about 2,000 nucleotides (migrates about mid way between the 2,400 nucleotide and the 1,350 nucleotide markers). No other strongly hybridizing bands were detected upon the blot. The ME-2 sequence seems to be expressed most abundantly in prostate and testis tissues. Moderate levels are detectable in spleen, uterus, small intestine, colon, and peripheral blood leukocyte tissues. In this experiment lower amounts of hybridization were observed in thymus tissue.

FIG. 6 demonstrates the pattern of EPP2 mRNA expression in various human tissues. A commercial Northern blot (BD Biosciences; San Diego, Calif.) was hybridized with the complete $^{32}$P-labeled EPP2 coding sequence of FIG. 3B. Conditions of hybridization and washing were as described by the manufacturer. Hybridizing bands were observed corresponding to a mRNA of about 1,000 nucleotides (migrates just faster than the 1,350 nucleotide marker). The EPP2 sequence seems to be expressed most abundantly in prostate, testis, colon and peripheral blood leukocyte. Lesser amounts of signal were visualized in spleen, thymus, and small intestine tissues, but little or no signal was detected in uterus tissue.

FIG. 7 shows the pattern of expression of recombinant ME-5 in an insect cell host. The ME-5 cDNA was cloned for expression as a 6× histidine-tagged recombinant protein in insect cells. A culture of Sf9 insect cells expressing recombinant ME-5 was prepared and lysed. The culture medium, PBS wash, and the soluble and insoluble fractions of the cell lysate were analyzed by SDS PAGE and staining (left panel) of the gel with GelCode blue (Pierce Chemicals; Rockford, Ill.). The expression samples were also evaluated by Western blotting (right panel) with an anti-HisG mouse monoclonal antibody (Invitrogen; Carlsbad, Calif.) followed by an $^{125}$I-labeled rabbit anti-mouse IgG secondary antibody. The recombinant protein was obscured by the multiplicity of protein bands in the stained gel at left, but a band of about 38 kD was clearly detected by the Western blot. This confirmed the presence of a 6× His-tagged protein with the approximate molecular weight expected for the recombinant ME-5 antigen. No recombinant ME-5 protein was detectable in the cell culture medium, but some was present in the PBS used to wash the insect cells prior to lysis. Most of the recombinant ME-5 protein seemed to be present in the soluble fraction of the insect cell lysate, but some was associated with the insoluble material.

FIG. 8 shows the pattern of expression of recombinant ME-2 in an insect cell host. The ME-2 cDNA was cloned for expression as a 6× histidine-tagged recombinant protein in insect cells. A culture of Sf9 insect cells expressing recombinant ME-2 was prepared and lysed. The culture medium, PBS wash, and the soluble and insoluble fractions of the cell lysate were analyzed by SDS PAGE and staining (left panel) of the gel with GelCode blue (Pierce Chemicals; Rockford, Ill.). The expression samples were also evaluated by Western blotting (right panel) with an anti-HisG mouse monoclonal antibody (Invitrogen; Carlsbad, Calif.) followed by an $^{125}$I-labeled rabbit anti-mouse IgG secondary antibody. The recombinant protein was obscured by the multiplicity of protein bands in the stained gel at left, but a band of about 49 kD was clearly detected by the Western blot. This confirmed the presence of a 6× His-tagged protein with the approximate molecular weight expected for the recombinant ME-2 protein. No recombinant ME-2 protein was detectable in the cell culture medium, but some was present in the PBS used to wash the insect cells prior to lysis. Approximately equal amounts of the recombinant ME-2 protein seemed to be distributed between the soluble and insoluble fractions of the insect cell lysate.

FIG. 9 shows the pattern of expression of recombinant EPP2 in an insect cell host. The EPP2 cDNA was cloned for expression as a 6× histidine-tagged recombinant protein in insect cells. A culture of Sf9 insect cells expressing recombinant EPP2 was prepared and lysed. The culture medium, PBS wash, and the soluble and insoluble fractions of the cell lysate were analyzed by SDS PAGE and staining (left panel) of the gel with GelCode blue (Pierce Chemicals; Rockford, Ill.). The expression samples were also evaluated by Western blotting (right panel) with an anti-HisG mouse monoclonal antibody (Invitrogen; Carlsbad, Calif.) followed by an $^{125}$I-labeled rabbit anti-mouse IgG secondary antibody. The recombinant protein was obscured by the multiplicity of protein bands in the stained gel at left, but a band of about 9 kD was clearly detected by the Western blot. This confirmed the presence of a 6× His-tagged protein with the approximate molecular weight expected for the recombinant EPP2 protein. No recombinant EPP2 protein was detectable in the cell culture medium, nor was any measurable amount present in the PBS used to wash the insect cells prior to lysis. Approximately equal amounts of the recombinant EPP2 protein seemed to be distributed between the soluble and the insoluble fractions of the insect cell lysate.

FIG. 10 shows the isolation of the recombinant 6×-tagged ME-5 protein using immobilized metal affinity chromatography (IMAC). Recombinant ME-5 protein was expressed in Sf9 insect cells and the cells were lysed in IMAC column binding buffer. The soluble fraction of the insect cells (Lysate) was loaded onto a column of Chelating Sepharose Fast Flow (Amersham Biosciences; Piscataway, N.J.) that had been charged with nickel ions. The lysate was captured after passing through the column resin (breakthrough) and the column was washed extensively with IMAC wash buffer. The recombinant ME-5 bound to the resin was eluted from the column with buffer containing imidazole. Samples of the lysate, breakthrough, wash, and elution were analyzed by SDS PAGE and Western blot as described above. The stained gel showed the complexity of the insect cell lysate, which resulted in a smear of protein for this and the breakthrough samples. A reasonable amount of non-binding protein contaminants were washed away with the A20 Column buffer, and a nice band corresponding to a 38 kD protein was present among the material eluted from the column with imidazol. Western blotting of these samples showed good levels of the recombinant ME-5 protein in the lysate, and in the breakthrough showing that in this particular experiment the amount of ME-5 exceeded the binding capacity for the column. Perhaps a trace of ME-5 was in the A20 Column buffer wash used to remove bound impurities from the Sepharose. The Western showed intense anti-HisG antibody reactivity with the eluted and partially purified 38 kD ME-5 antigen.

FIG. 11 shows the isolation of the recombinant 6×-tagged ME-2 protein using immobilized metal affinity chromatography (IMAC). Recombinant ME-2 protein was expressed in Sf9 insect cells and the cells were lysed in IMAC column binding buffer. The soluble fraction of the insect cells (Lysate) was loaded onto a column of Chelating Sepharose Fast Flow (Amersham Biosciences; Piscataway, N.J.) that had been charged with nickel ions. The lysate was captured after passing through the column resin (break-through) and the column was washed extensively with IMAC wash buffers A10, A15, and A20. The recombinant ME-2 bound to the resin was eluted from the column with buffer containing imidazole. Samples of the lysate, breakthrough, wash, and elution were analyzed by SDS PAGE and Western blot as described above. The stained gel showed the complexity of the insect cell lysate, which resulted in a smear of protein for this, and the break-through samples. A substantial amount of non-binding protein contaminants were washed from the resin with the A10, A15, and A20 Column Wash buffers. Finally, a nice band corresponding to a 49 kD protein was present among the material eluted from the column with imidazol. Western blotting of these samples showed good levels of the recombinant ME-2 protein in the lysate, and some also in the break-through showing that in this particular run the amount of ME-2 may have exceeded the binding capacity for the column. Perhaps a trace of ME-2 was present in the A10 Column Wash buffer, but stronger signals were detected in the A15 and A20 Column Wash buffers wash used to remove bound impurities from the Sepharose. The Western showed intense anti-HisG antibody reactivity with the eluted and partially purified 49 kD ME-2 antigen.

FIG. 12 shows the isolation of the recombinant 6×-tagged EPP2 protein using immobilized metal affinity chromatography (IMAC). Recombinant EPP2 protein was expressed in Sf9 insect cells and the cells were lysed in denaturing IMAC column binding buffer. The insect cell lysate was loaded onto a column of Chelating Sepharose Fast Flow (Amersham Biosciences; Piscataway, N.J.) that had been charged with nickel ions. The lysate was captured after passing through the column resin (break-through) and the column was washed extensively with A10, A15, A20, A25, and A30 IMAC wash buffers. The recombinant EPP2 bound to the resin was eluted from the column with buffer containing imidazole. Samples of the lysate, break-through, washes, and elution were analyzed by SDS PAGE and Western blot as described above. The stained gel showed the complexity of the insect cell lysate, which resulted in a smear of protein. In addition, the break-through and the A10 Column Wash samples contained a substantial amount of material that did not bind to the column matrix. Very little protein contaminants were washed away with the A15, A20, A25, and A30 Column Wash buffers as visualized from the stained gel. A very nice band corresponding to a 9 kD protein was present among the material eluted from the column with imidazol. Western blotting of these samples showed detectable levels of the recombinant EPP2 protein in the lysate. Little or no EPP2 was present in the break-through, A10, or A15 samples showing that in this particular run the EPP2 bound to the column pretty well. Perhaps a trace of EPP2 was detected in the in the A20, A25, and A30 Column Wash buffers used to remove bound impurities from the Sepharose. The Western showed intense anti-HisG antibody reactivity with the eluted 9 kD EPP2 antigen.

FIG. 13 shows Western blot analysis of isolated recombinant ME-5 protein, as well as the native ME-5 antigen present in RL95-2 endometrial carcinoma cells. Cultured RL95-2 cells were lysed and a sample of the soluble fraction electrophoresed in a 4% to 20% Tris Glycine SDS PAGE gel (Invitrogen; Carlsbad, Calif.). A sample of recombinant ME-5 isolated by IMAC from Sf9 insect cells was included on the gel as a positive control for the anti-ME-5 antibody. Western blotting was performed with the 2D1 anti-ME-5 monoclonal antibody followed by an $^{125}$I-labeled rabbit anti-mouse IgG secondary antibody. A clear band of reactivity was observed (right lane) among the RL95-2 proteins that seemed to migrate with a molecular weight that was slightly greater than the insect cell recombinant.

FIG. 14 is a Western blot showing ME-5 native antigen expression in various human tissues. Tissue protein extracts in SDS PAGE sample buffer (protein medleys: BD Biosciences; San Diego, Calif.) were separated in SDS PAGE gels and Western blotting done as described in FIG. 13. The native ME-5 antigen seems to be ubiquitously present in all tissues examined, but it appears to be slightly more abundant in heart, liver, ovary and kidney extracts.

FIGS. 15A and 15B show representative line immunoblots illustrating the ability of recombinant ME-5 to react with antibodies present in serum obtained from endometriosis patients, but not in normal control sera. Each strip contains immobilized antigens that were slotted onto the membrane at different concentrations. The protein concentrations for ME-5 are 0.018, 0.036, 0.072, and 0.144 milligrams per milliliter (mg/ml). The optimal concentration for discrimination between patients and controls was 0.036 mg/ml as designated by the arrow at the right of the line blot strips. One advantage of the line immunoblot assay is that many different proteins can be interrogated on a single strip, and additional unrelated proteins are present on the strips that act as internal controls. A reagent control (mouse anti-human IgG monoclonal) is included on each strip to act as a positive control. Each strip was incubated with serum from a normal person (control) or from a patient with confirmed endometriosis. Line blot patterns for a total of 11 controls (A6, A7, A8, A9, A10, A14, A15, A16, A17, A18, A21) are shown in FIG. 15A. In addition, 23 endometriosis patients (DS01, DS02, DS03, DS04, DS05, DS06, DS07, DS08, DS10, DS11, DS12, DS13, DS27, DS28, DS29, DS30, DS31, DS32, DS33, DS34, DS36, DS38, DS39) are shown in FIG. 15B. The intensity of staining of each band is indicative of the reactivity of the tested serum with ME-5. In this selected lineblot panel, ME-5 at a concentration of 0.036 mg/ml detected 18 endometriosis patients as positive (DS01, DS03, DS05, DS06, DS10, DS11, DS12, DS27, DS28, DS29, DS30, DS31, DS32, DS33, DS34, DS36, DS38, and DS39). In addition, 5 endometriosis patients (DS02, DS04, DS07, DS08, and DS13) yielded patterns of reactivity that were a bit lower. Among the 11 normal controls, ME-5 clearly did not react with nine of them (A6, A7, A8, A10, A15, A16, A17, A18, A21). There may have been detectable signals seen for two of the normal controls (A9, A14), but these were very light relative to the patterns seen with sera from the endometriosis patients and are interpreted as negative.

FIGS. 16A and 16B show representative line immunoblots illustrating the ability of recombinant ME-2 to react with antibodies present in serum obtained from endometriosis patients, but not in normal control sera. Each strip contains immobilized antigens that were slotted onto the membrane at different concentrations. The protein concentrations of ME-2 applied to the strips are 0.009 (for endometriosis sera, only), 0.018, 0.036, 0.072, and 0.144 (for control sera, only) milligrams per milliliter (mg/ml). The optimal concentration for discrimination between patients and controls was set at 0.018 mg/ml as designated by the arrow at the right of the line blot strips. One advantage of the line immunoblot assay is that many different proteins can be interrogated on a single strip for reactivity with antibodies, and additional unrelated proteins are present on the strips that act as internal controls. A reagent control (mouse anti-human IgG monoclonal) is included on each strip to capture human IgG and act as a positive control. Each strip was incubated with serum from a normal person (control) or from a patient with confirmed endometriosis. Line blot patterns for a total of 11 controls (A01, A02, A03, A06, A08, A15, A20, A21, A22, A23, and A24) are shown in FIG. 16A. In addition, 21 endometriosis patients (DS10, DS11, DS12, DS13, DS14, DS17, DS19, DS20, DS21, DS22, DS24, DS25, DS26, DS27, DS28, DS29, DS30, DS31, DS32, DS33, and DS35) are shown in FIG. 16B. The intensity of staining of each band is indicative of the reactivity of the tested serum with ME-2. In this selected lineblot panel, ME-2 at a concentration of 0.018 mg/ml detected 15 endometriosis patients as positive (DS012, DS17, DS19, DS20, DS21, DS22, DS24, DS25, DS26, DS27, DS28, DS30, DS31, DS33, and DS35). In addition, 6 endometriosis patients (DS10, DS11, DS13, DS14, DS29, and DS32) yielded patterns of reactivity that were a bit lower. Among the 11 normal controls, ME-2 did not react with any of them at the 0.018 mg/ml cutoff applied to endometriosis patients.

FIGS. 17A and 17B show representative line immunoblots illustrating the ability of recombinant EPP2 to react with antibodies present in serum obtained from endometriosis patients, but not in normal control sera. Each strip contains immobilized antigens that were slotted onto the membrane at different concentrations. The protein concentrations for EPP2 are 0.01, 0.025, 0.05, 0.1, 0.15, 0.2, and 025 milligrams per milliliter. The optimal concentration for discrimination between patients and controls was 0.05 mg/ml as designated by the arrow at the right of the line blot strips. One advantage of the line immunoblot assay is that many different proteins can be interrogated on a single strip, and additional unrelated proteins are present on the strips that act as internal controls.

A reagent control (mouse anti-human IgG monoclonal) is included on each strip to capture human IgG in the sample and act as a positive control. Each strip was incubated with serum from a normal person (control) or from a patient with confirmed endometriosis. Line blot patterns for a total of 11 controls (A01, A02, A03, A04, A05, A09, A13, A14, A16, A20, and A24) are shown in FIG. 17A. In addition, 39 endometriosis patients (DS06, DS12, DS24, DS05, BBI01, BBI02, BBI03, BBI04, BBI05, BBI06, BBI07, BBI08, BBI09, BBI10, BBI11, BBI12, BBI13, BBI14, BBI15, BBI16, BBI20, BBI21, BBI22, BBI23, BBI24, BBI25, BBI26, BBI27, BBI28, BBI30, BBI31, BBI32, BBI34, BBI35, BBI36, BBI37, BBI38, BBI39, and BBI40) are shown in FIG. 17B. The intensity of staining of each band is indicative of the reactivity of the tested serum with EPP2. In this selected lineblot panel, EPP2 at a concentration of 0.05 mg/ml detected 33 endometriosis patients as positive (DS06, DS12, DS24, DS05, BBI02, BBI03, BBI04, BBI06, BBI07, BBI08, BBI09, BBI10, BBI11, BBI12, BBI13, BBI15, BBI16, BBI20, BBI22, BBI23, BBI25, BBI26, BBI27, BBI28, BBI30, BBI31, BBI32, BBI34, BBI35, BBI37, BBI38, BBI39, and BBI40). In addition, 6 endometriosis patients (BBI01, BBI05, BBI14, BBI21, BBI24, and BBI36) yielded patterns of reactivity that were much lower. Among the 11 normal controls, EPP2 did not react strongly with any of them at the 0.05 mg/ml cut off.

"Polypeptide" refers to a polymer composed of amino acid residues, related naturally occurring structural variants, and synthetic non-naturally occurring analogs thereof linked via peptide bonds, related naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to the substitution in a polypeptide of an amino acid with a functionally similar amino acid. It is to be understood that the claims encompass conservative substitution. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Allelic Variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

This invention provides methods for diagnosing endometriosis in a subject by detecting in a sample from the subject a diagnostic amount of an antibody that specifically binds to ME-2, ME-5 or EPP2 polypeptide. Suitable patient samples include, without limitation, saliva, blood or a blood product (e.g., serum), peritoneal fluid, urine, menstrual fluid, vaginal secretion. The antibodies can be detected by any of the methods for detecting proteins described herein. However, sandwich type assays are particularly useful. In one version, all antibodies are captured onto a solid phase, for example using protein A, and antibodies specific for ME-2, ME-5 or EPP2 are detected using a directly or indirectly labeled ME-2, ME-5 or EPP2 or polypeptide fragment of it having an epitope of ME-2, ME-5 or EPP2. In another version of the assay, ME-2, ME-5 or EPP2 or an antigenic fragment of it can be used as the capture molecule and captured antibodies can be detected.

ME-2, ME-5 or EPP2 that is shed into the peritoneal fluid of women with endometriosis is useful in methods of diagnosing endometriosis. These methods include detecting ME-2, ME-5 or EPP2 in a biological sample of a subject. Suitable samples include, without limitation, saliva, blood or a blood product (e.g., serum), urine, menstrual fluid, vaginal secretion and, in particular, peritoneal fluid. ME-2, ME-5 or EPP2 can be detected by any of the methods described herein. Any detection of ME-2, ME-5 or EPP2 above a normal range is a positive sign in the diagnosis of endometriosis.

The phrase "substantially identical," in the context of two nucleic acids or polypeptides, refers to two or more sequences or sub-sequences that have at least 60%, 80%, 90%, 95% or 98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

The invention disclosed herein is the isolation of human cDNA molecules that encode three distinct endometrial proteins, and characterization of the corresponding antigens. These cDNA and the corresponding antigens have been designated ME-5, ME-2, and EPP2 and the proteins expressed from them are the targets of autoantibodies present in the serum of women who suffer from endometriosis. These features of the ME-5, ME-2, and EPP2 proteins makes them useful markers for diagnosis of endometrial disease and this is shown in detail in the Examples below.

Example 1

Identification and Cloning of the ME-5, ME-2, and EPP2 cDNAS

The endometriosis tissue cDNA library was generated using poly A$^+$ RNA isolated from a deep embedded endometriosis tissue specimen donated by Professor Philip Koninckx at the Catholic University of Leuven. Total RNA was isolated from the tissue using Trizol reagent (Biorad Laboratories; Hercules, Calif.), and poly A+ RNA was prepared by hybridization to oligo poly T coupled magnetic particles using a commercial kit (PolyATract; Promega; Madison, Wis.). Library construction was carried out using the Lambda ZAP® II vector system following instructions obtained from the supplier (Stratagene; San Diego, Calif.). The initial ME-5 and ME-2 cDNA clones were identified by immunoscreening using, as primary antibody, a single endometriosis patient serum specimen obtained from a woman diagnosed with mild disease. This serum was adsorbed of nonspecific anti-*E. coli*/lambda phage antibodies by diluting the sera 1:50 in a commercial *E. coli* phage lysate (Stratagene; San Diego, Calif.) according to the protocol provided by the supplier. In a separate series of experiments the initial EPP2 cDNA clone was identified in similar immunoscreening protocol except that, as primary antibody, a pool of ten endometriosis patient serum specimens was used. The sera in this pool were from women with various stages of endometrial disease. Again the serum was adsorbed of non-specific anti-*E. coli*/lambda phage antibodies by dilution with a commercial *E. coli* phage lysate (Stratagene; San Diego, Calif.) as described above. The second antibody for all screening experiments was $^{125}$I-labeled monoclonal antibody reactive with human immunoglobulin. Negative control human serum was used to screen the clones in parallel to verify the reactivity. Immunoreactive clones were plaque-purified three times and rescued by in vivo excision into the pBluescript® SK(−) phagemid vector using methods supplied by the manufacturer (Stratagene; San Diego, Calif.).

Example 2

Characterization of ME-5, ME-2, and EPP2 cDNA and Protein

Sequence analysis of both strands of each of the original isolated ME-5, ME-2, and EPP2 clones was performed upon an ABI Biosystems 373 DNA Sequencer (PE Applied Biosystems; Foster City, Calif.). The nucleic acid sequences so generated were analyzed using Bionet software to identify nucleic acid and protein characteristics and for homology comparisons with nucleic acid and protein sequences present in the database.

The ME-5 cDNA sequence is presented in FIG. 1A (SEQ ID NO:1) and it is 1,279 base pairs in size excluding the poly dA track. A 5' noncoding sequence of 112 base pairs was identified just upstream of the suspected ATG start codon. There is a 3' non coding sequence of 254 base pairs down stream of the TGA stop codon and this is followed by a stretch of dA residues that would correspond to the poly A tail at the 3' end of the mRNA. Both the start and stop codon are highlighted in bold type in FIGS. 1A and 1B. The ME-5 coding sequence is shown in FIG. 1B (SEQ ID NO:2) as predicted from the entire isolated cDNA sequence (FIG. 1A). The coding region is 912 base pairs in size, including the start and stop codons. The cDNA codes for a predicted protein of 303 amino acids shown in FIG. 1C (SEQ ID NO:3) and the calculated molecular weight was about 35,000 Daltons. The translation product is slightly acidic with a calculated isoelectric value of 5.7.

Computer-assisted database searches (National Center for Biotechnology Information [NCBI] Basic Local Alignment Search Tool [BLAST]) was used to perform homology comparisons with sequences contained within the GenBank nucleic acid database. It was discovered that two other laboratories working on different projects independently isolated an essentially identical cDNA molecule.

First Scanlan and coworkers isolated the identical 1-NY-CO-7 cDNA using a process described in a paper: "*Characterization of human colon cancer antigens recognized by autologous antibodies*" published by Scanlan et al. [Int. J. Cancer 76, 652-658 (1998)]. The approach used by these individuals was similar to that employed for discovery of the ME-5 cDNA in that these investigators screened colorectal cancer cDNA libraries with serum from colorectal cancer patients. Comparing the ME-5 sequence with that of 1-NY-CO-7 revealed a substantial number of differences between the two. First, in the manuscript the 1-NY-CO-7 mRNA sequence was reported to be 1.22 kb perhaps slightly smaller than the ME-5 sequence of this invention. Second, the 1-NY-CO-7 protein was reported to be 356 amino acids on size which is considerably larger than the predicted ME-5 protein. Finally, there were three base mismatches in the carboxy terminal portion of the two sequences and two of these resulted in amino acid changes. The nucleotide changes were at nucleotide 807 (C->G [occurs in $3^{rd}$ position of codon with no amino acid change->proline]), 814 (C->G [arginine->glycine]), and 838 (C->T [leucine->phenylalanine]) relative to the ME-5 coding domain. The authors commented that the 1-NY-CO-7 sequence was novel (little or no homologies with DNA sequences listed in the Gen Bank/EMBO data bases with the exception of expressed sequence tags), and the protein as having tetratricopeptide repeats (TPR, see below). The 1-NY-CO-7 sequence did not appear among those colon-specific sequences that were characterized in the paper, rather it was a direct submission to GenBank without further characterization of the nucleic acid or protein. When the 1-NY-CO-7 GenBank sequences were compared to that of ME-5 they were identical except for the three nucleotide mismatches described above.

Second, Ballinger and coworkers identified the identical Carboxy terminus of Hsp70-interacting protein (CHIP) using a drastically different process described in a paper published: "*Identification of CHIP, a novel tetratricopeptide repeat-containing protein that interacts with heat shock proteins and negatively reglates chaperone functions*" Ballinger et al. [*Mol. Cell. Biol.* 19, 4535-4545 (1999)]. In this paper the authors were interested in isolating novel tetratricopeptide repeat-containing proteins. The CHIP sequence was identified by screening a cardiac cDNA library with the cDNA sequence for the human CyP-40 protein at different stringency's. A low stringency hybridization (42° C.) yielded 12 clones that did not hybridize at higher stringency (55° C.). Characterization of the clones revealed 8 of them corresponded to human CyP-40, and 4 clones encoded CHIP that was a sequence with no homology to known genes. Characterization of CHIP revealed that it interacts with both Hsc70 and Hsp70 by binding to the carboxy terminus of these proteins through sequences within the amino terminus of CHIP. Interestingly recombinant CHIP inhibited the Hsp40-stimulated ATPase activity of Hsc70 and Hsp70 suggesting that it regulated the forward reaction of the substrate-binding cycle.

Both of these sequences have near perfect homology with the ME-5 nucleic acid and protein sequences of this invention. However, the anticipated usefulness of ME-5 in the diagnosis of endometriosis was not contemplated by the aforementioned papers.

The ME-2 cDNA sequence is presented in FIG. 2A (SEQ ID NO:4) and it is 1,332 base pairs in size excluding the poly dA track. A 5' noncoding sequence of 54 base pairs was identified just upstream of the suspected ATG start codon. There is a 3' non coding sequence of 95 base pairs down stream of the TAG stop codon and this is followed by a stretch of dA residues that would correspond to the poly A tail at the 3' end of the mRNA. Both the start and stop codon are highlighted in bold type in FIGS. 2A and 2B. The ME-2 coding sequence is shown in FIG. 2B (SEQ ID NO:5) as predicted from the entire isolated cDNA sequence (FIG. 2A). The coding region is 1182 base pairs in size, including the start and stop codons. The cDNA codes for a predicted protein of 393 amino acids shown in FIG. 2C (SEQ ID NO:6) and the calculated molecular weight was about 45,000 Daltons. The translation product is slightly acidic with a calculated isoelectric value of 8.8.

Computer-assisted database searches (National Center for Biotechnology Information [NCBI] Basic Local Alignment Search Tool [BLAST]) was used to perform homology comparisons with the ME-2 cDNA with sequences contained within the GenBank nucleic acid database. It was discovered that while there are several submissions by groups involved with analysis of the human genome sequence all documents are direct submissions. Moreover, none of these submissions have been published in the scientific literature, and all refer to "unknown protein" or "hypothetical protein" or "unnamed protein product" and not to a defined product or function. These can be found in accession numbers GI:12652526, GI:22761484, and GI:24431994 for example. Therefore even though sequences corresponding to the ME-2 cDNA and protein are present in the public domain, the nature is not known and the involvement of the protein in endometriosis is certainly not-anticipated by this public information. Consequently, the ME-2 cDNA and protein sequences are unique and exclusively implicated in the human disease of endometriosis by the disclosures contained in this invention.

The EPP2 cDNA sequence is presented in FIG. 3A (SEQ ID NO:7) and it is 868 base pairs in size excluding the poly dA track. A 5' noncoding sequence of 45 base pairs was identified just upstream of the suspected ATG start codon. There is a 3' non coding sequence of 522 base pairs down stream of the TAA stop codon and this is followed by a stretch of dA residues that would correspond to the poly A tail at the 3' end of the mRNA. Both the start and stop codon are highlighted in bold type in FIGS. 3A and 3B. The EPP2 coding sequence is shown in FIG. 3B (SEQ ID NO:8) as predicted from the entire isolated cDNA sequence (FIG. 3A). The coding region is 300 base pairs in size, including the start and stop codons. The cDNA codes for a predicted protein of 99 amino acids shown in FIG. 3C (SEQ ID NO:9) and the calculated molecular weight was approximately 9300 Daltons. Interestingly 18 of the amino acids are arginine residues therefore the translation product is very basic with a calculated isoelectric value of 12.5.

Computer-assisted database searches (National Center for Biotechnology Information [NCBI] Basic Local Alignment Search Tool [BLAST]) was used to perform homology comparisons with the EPP2 cDNA with sequences contained within the GenBank nucleic acid database. In the fashion described above for ME-2, it was discovered that EPP2 was also represented by several direct submissions from groups involved with analysis of the human genome sequence. Moreover, as described above, none of these submissions have been published in the scientific literature, and all refer to "unknown protein" or "hypothetical protein" or "unnamed protein product" and not to a defined product or function. These can be found in accession numbers GI:12652993, GI:24308450, and GI:20892293 for example. Therefore even though sequences corresponding to the EPP2 cDNA and protein are present in the public domain the nature is not known and the involvement of the protein in endometriosis is certainly not anticipated by this public information. Consequently, the EPP2 cDNA and protein sequences are unique and exclusively implicated in the human disease of endometriosis by the disclosures contained in this invention.

Example 3

Northern Blotting with Radiolabeled ME-5, ME-2, and EPP2 Probes: mRNA Character and Expression Pattern Gene expression profile of ME-5 from normal human tissues was done by performing Northern blot analysis with a commercial Multiple Tissue Northern Blot (BD Biosciences; San Diego, Calif.), the results of which are presented in FIG. 4. The commercial Northern blot contained RNA from the following tissues: spleen, thymus, prostate, testis, uterus, small intestine, colon (no mucosa), and peripheral blood leukocyte. The entire 912 base pair coding sequence was isolated by electrophoresis in a low melting agarose gel, and labeled with $^{32}$P by random priming. The $^{32}$P-labeled ME-5 probe was used for hybridization to the Northern blot using the procedure supplied by the manufacturer. After washing the blot was exposed to X-ray film. Upon development of the film a band at about 1.4 kb on the Northern blot corresponds to the ME-5 transcript of the expected size (FIG. 4). The transcript can be seen in all tissues and is particularly abundant in prostate, testis and uterus tissues.

Gene expression profile of ME-2 from normal human tissues was done by performing Northern blot analysis with a commercial Multiple Tissue Northern Blot (BD Biosciences; San Diego, Calif.), the results of which are presented in FIG. 5. The commercial Northern blot contained RNA from the following tissues: spleen, thymus, prostate, testis, uterus, small intestine, colon (no mucosa), and peripheral blood leukocyte. The entire 1182 base pair coding sequence was isolated by electrophoresis in a low melting agarose gel, and labeled with $^{32}$P by random priming. The $^{32}$P-labeled ME-2 probe was used for hybridization to the Northern blot using the procedure supplied by the manufacturer. After washing the blot was exposed to X-ray film. Upon development of the film a band at about 2.0 kb on the Northern blot corresponds to the ME-2 transcript hybridizing to the labeled probe (FIG. 5). The transcript can be seen in all tissues and is particularly abundant in prostate and testis. In addition, good levels of hybridization were observed amount the RNAs expressed in spleen; uterus, small intestine, colon, and peripheral blood lymphocyte tissues. Interestingly, despite the pattern observed with the peripheral blood lymphocytes, relatively little signal could be detected in thymus tissue.

Gene expression profile of EPP2 from normal human tissues was done by performing Northern blot analysis with a commercial Multiple Tissue Northern Blot (BD Biosciences; San Diego, Calif.), the results of which are presented in FIG. 6. The commercial Northern blot contained RNA from the following tissues: spleen, thymus, prostate, testis, uterus, small intestine, colon (no mucosa), and peripheral blood leukocyte. The entire 300 base pair EPP2 coding sequence was isolated by electrophoresis in a low melting agarose gel, and labeled with $^{32}$P by random priming. The $^{32}$P-labeled EPP2 probe was used for hybridization to the Northern blot using the procedure supplied by the manufacturer. After washing the blot was exposed to X-ray film. Upon development of the film a band at about 1.0 kb on the Northern blot corresponds to the EPP2 transcript hybridizing to the labeled probe (FIG. 6). The transcript can be seen in all tissues and is most abundant in prostate, testis, colon, and peripheral blood lymphocyte tissues. In addition, the transcript is present but the relative levels of hybridization are lower among the RNAs expressed in spleen, thymus, uterus, and small intestine tissues.

Example 4

Expression of Recombinant ME-5, ME-2, and EPP2 Proteins in an Insect Cell Host

The ME-5 antigen was cloned for expression as a 6× histidine-tagged fusion protein in insect cells. The sequence of the ME-5 cDNA insert was generated by PCR amplification using specific primers that flanked the 912 by coding region. Unique sites for the Bam HI and Eco RI restriction enzymes were incorporated into the primers to maintain the ME-5 reading frame with the vector sequences. The PCR amplicons were digested with the Bam HI and Eco RI restriction enzymes (Stratagene; San Diego, Calif.) and purified by agarose gel electrophoresis. The insect cell transfer vector Blue Bac His2a (Stratagene; San Diego, Calif.) was also digested with the restriction enzymes Barn HI and Eco RI and treated with calf intestine alkaline phosphatase. The ME-5 cDNA insert was ligated with the vector and competent bacteria transformed. Individual isolated clones were grown, plasmid DNA isolated, and digested with the restriction enzymes Bam HI and Eco RI. Clones producing a band of about 900 by in addition to the linear vector were chosen. Several candidates were further characterized by DNA sequence analysis to verify that no changes occurred during the process of PCR amplification and cloning. One clone was confirmed to have no mutations and this was used for development of recombinant baculovirus vectors. Recombinant baculoviruses were generated by cotransfection of Sf9 insect cells with baculovirus DNA and the ME-5 transfer vector. The baculoviruses were isolated by plaque purification and used to evaluate expression patterns in pilot cultures. The recombinant baculovirus virus and pilot scale cultures were evaluated for expression patterns. One recombinant baculovirus clone was identified which expressed an antigen of approximately 38 kD, which was detected in both the soluble and the insoluble fraction of the insect cell lysates. The clone was expanded into large-scale virus stocks for expression of recombinant ME-5 protein. This was used to infect a large-scale culture of Sf9 insect cells. The pattern of expression is illustrated in FIG. 7, and is best visualized by the Western blot analysis (FIG. 7). The presence of recombinant ME-5 was confirmed with a commercial anti-HisG monoclonal antibody (Invitrogen; Carlsbad, Calif.) followed by an $^{125}$I-labeled rabbit anti-mouse IgG secondary antibody. This confirms the presence of a 6× histidine-tagged protein of approximately 38 kD which is the molecular weight expected for ME-5. The recombinant was detected in both the soluble and the insoluble fraction of the insect cell lysates, but slightly more antigen seems to be localized in the soluble fraction. In addition some antigen was present in the PBS used to wash the infected cells prior to the lysis.

The ME-2 antigen was cloned for expression as a 6× histidine-tagged fusion protein in insect cells as described above for the ME-5 activity. The sequence of the ME-2 cDNA insert was generated by PCR amplification using specific primers that flanked the 1182 by coding region. Unique sites for the Bam HI and Eco RI restriction enzymes were incorporated into the primers to maintain the ME-2 reading frame with the vector sequences. The PCR amplicons were digested with the Bam HI and Eco RI restriction enzymes (Stratagene; San Diego, Calif.) and purified by agarose gel electrophoresis. The insect cell transfer vector Blue Bac His2a (Stratagene; San Diego, Calif.) was also digested with the restriction enzymes Bam HI and Eco RI and treated with calf intestine alkaline phosphatase. The ME-2 cDNA insert was ligated with the vector and competent bacteria transformed. Individual isolated clones were grown, plasmid DNA isolated, and digested with the restriction enzymes Bam HI and Eco RI. Clones producing a band of about 1100 by in addition to the linear vector were chosen. Several candidates were further characterized by DNA sequence analysis to verify that no changes occurred during the process of PCR amplification and cloning. One clone was confirmed to have no mutations and this was used for development of recombinant baculovirus vectors. Recombinant baculoviruses were generated by cotransfection of Sf9 insect cells with baculovirus DNA and the ME-2 transfer vector. The baculoviruses were isolated by plaque purification and used to evaluate expression patterns in pilot cultures. The recombinant baculovirus virus and pilot scale cultures were evaluated for expression patterns. One recombinant baculovirus clone was identified which expressed an antigen of approximately 49 kD, which was detected in both the soluble and the insoluble fraction of the insect cell lysates. The clone was expanded into large-scale virus stocks for expression of recombinant ME-2 protein. This was used to infect a large-scale culture of Sf9 insect cells. The pattern of expression is illustrated in FIG. 8, and is best visualized by the Western blot analysis (FIG. 8). The presence of recombinant ME-2 was confirmed with a commercial anti-HisG monoclonal antibody (Invitrogen; Carlsbad, Calif.) followed by an $^{125}$I-labeled rabbit anti-mouse IgG secondary antibody. This confirms the presence of a 6× histidine-tagged protein of approximately 49 kD which is the molecular weight expected for ME-2. The recombinant was detected in both the soluble and the insoluble fraction of the insect cell lysates, but slightly more antigen seems to be localized in the soluble fraction. In addition some antigen was present in the PBS used to wash the infected cells prior to the lysis.

The EPP2 antigen was cloned for expression as a 6× histidine-tagged fusion protein in insect cells as described above. The sequence of the EPP2 cDNA insert was generated by PCR amplification using specific primers that flanked the 300 by coding region. Unique sites for the Bam HI and Eco RI restriction enzymes were incorporated into the primers to maintain the EPP2 reading frame with the vector sequences. The PCR amplicons were digested with the Bam HI and Eco RI restriction enzymes (Stratagene; San Diego, Calif.) and purified by agarose gel electrophoresis. The insect cell transfer vector Blue Bac His2a (Stratagene; San Diego, Calif.) was also digested with the restriction enzymes Bam HI and Eco RI and treated with calf intestine alkaline phosphatase. The EPP2 cDNA insert was ligated with the vector and competent bacteria transformed. Individual isolated clones were grown, plasmid DNA isolated, and digested with the restriction enzymes Bam HI and Eco RI. Clones producing a band of about 300 by in addition to the linear vector were chosen. Several candidates were further characterized by DNA sequence analysis to verify that no changes occurred during the process of PCR amplification and cloning. One clone was confirmed to have no mutations and this was used for development of recombinant baculovirus vectors. Recombinant baculoviruses were generated by cotransfection of Sf9 insect cells with baculovirus DNA and the EPP2 transfer vector. The baculoviruses were isolated by plaque purification and used to evaluate expression patterns in pilot cultures. The recombinant baculovirus virus and pilot scale cultures were evaluated for expression patterns. One recombinant baculovirus clone was identified which expressed an antigen of approximately 9 kD, which was detected in both the soluble and the insoluble fraction of the insect cell lysates. The clone was expanded into large-scale virus stocks for expression of recombinant EPP2 protein. This was used to infect a large-scale culture of Sf9 insect cells. The pattern of expression is illustrated in FIG. 9, and is best visualized by the Western blot analysis (FIG. 9). The presence of recombinant EPP2 was confirmed with a commercial anti-HisG monoclonal antibody (Invitrogen; Carlsbad, Calif.) followed by an $^{125}$I-labeled rabbit anti-mouse IgG secondary antibody. This confirms the presence of a 6× histidine-tagged protein of approximately 9 kD which is the molecular weight expected for EPP2. The recombinant was detected in both the soluble and the insoluble fraction of the insect cell lysates, but slightly more antigen seems to be localized in the soluble fraction. In contrast to the patterns seen with the ME-5 and ME-2 protein expression, no EPP2 antigen was present in the PBS used to wash the infected cells prior to the lysis.

Example 5

Purification of Recombinant ME-5, ME-2, and EPP2 Protein from Insect Cells

Additional studies of the ME-5, ME-2, and EPP2 antigens require substantial amounts of isolated protein. Specifically, these are needed for evaluating the reactivity of the ME-5, ME-2, and EPP2 proteins with endometriosis patient serum specimens to establish clinical relevance. The recombinant ME-5, ME-2, and EPP2 antigens were isolated from the soluble fraction or the whole cell lysate by immobilized metal affinity chromatography (IMAC).

Recombinant ME-5 antigen was isolated from the soluble fraction of the insect cell lysate. Briefly, ME-5 recombinant baculovirus-infected insect cells were harvested after three days of infection by centrifugation. The cells were washed twice with PBS and the cell pellet frozen for one hour at −70° C. After thawing the cell pellet was suspended in binding buffer (500 mM NaCl, 20 mM Tris-HCl, pH 8.0) supplemented with protease inhibitor cocktail for mammalian tissues (Sigma; St. Louis, Mo.). The lysate was sonicated, and centrifuged at 18,000 rpm, 4° C. for 20 minutes to separate the soluble and insoluble fractions. The soluble fraction was dialyzed against binding buffer, and centrifuged at 18,000 rpm, 4° C. to remove impurities that might affect the performance of the column. Nickel-charged chelating Sepharose resin (Amersham Biosciences; Piscataway, N.J.) was equilibrated twice with 2× column volume of binding buffer. The resin was incubated with the ME-5 insect cell lysate for 20 minutes on a rocker at room temperature. The resin/lysate mixture is loaded on a column and washed with 40 column volumes of A20 Column Wash buffer (20 mM imidazole; 500 mM NaCl; 20 mM Tris-HCl, pH 8.0). Bound ME-5 protein was eluted from the column with elution buffer (500 mM imidazole; 500 mM NaCl; 20 mM Tris-HCl, pH 7.5). Protease inhibitor cocktail was added to the pooled elution fractions and protein concentration measured by BCA assay (Pierce; Rockford, Ill.) using a BSA standard curve. The eluted protein samples are analyzed upon SDS PAGE followed by staining with Coomassie blue or transfer to nitrocellulose and Western blotting as shown in FIG. 10. Such isolated ME-5 protein preparations are divided into aliquots and stored at −20° C. with 30% glycerol.

Recombinant ME-2 antigen was also isolated from the soluble fraction of the insect cell lysate. Briefly, ME-2 recombinant baculovirus-infected insect cells were harvested after three days of infection by centrifugation. The cells were washed with PBS and the cells lysed as described above. After dialysis the soluble fraction was allowed to bind to nickel-charged chelating Sepharose resin (Amersham Biosciences; Piscataway, N.J.) for 20 minutes at room temperature. The resin/lysate mixture is loaded on a column and washed sequentially with denaturing binding buffer A10 (10 mM imidazole, 1 M NaCl, 20 mM Tris-HCl, pH 8.0, 10% glycerol, 6 M Urea), A15 (buffer A10 containing 15 mM imidazole), and A20 (buffer A10 with 20 mM imidazole). Bound ME-2 protein was eluted from the column with elution buffer (500 mM imidazole; 500 mM NaCl; 20 mM Tris-HCl, pH 7.5). Protease inhibitor cocktail was added to the pooled elution fractions and protein concentration measured by BCA assay (Pierce; Rockford, Ill.) using a BSA standard curve. The eluted protein samples are analyzed upon SDS PAGE followed by staining with Coomassie blue or transfer to nitrocellulose and Western blotting as shown in FIG. 11. Such isolated ME-2 protein preparations are divided into aliquots and stored at −20° C. with 30% glycerol.

Recombinant EPP2 antigen was isolated from the whole insect cell lysate as follows. The EPP2 recombinant baculovirus-infected insect cells were harvested after three days of infection by centrifugation. The cells were washed twice with PBS and the cell pellet frozen for one hour at −70° C. After thawing the cell pellet was suspended in denaturing binding buffer (750 mM NaCl; 20 mM Tris-HCl, pH 8.0; 10% glycerol; 6 M guanidine HCl) supplemented with protease inhibitor cocktail for mammalian tissues (Sigma; St. Louis, Mo.). The lysate was sonicated, and centrifuged to separate the soluble and insoluble fractions. The soluble fraction was allowed to bind to nickel-charged chelating Sepharose resin (Amersham Biosciences; Piscataway, N.J.) for 20 minutes at room temperature. The resin is loaded on a column and washed sequentially with denaturing binding buffer A10 (10 mM imidazole, 1 M NaCl, 20 mM Tris-HCl, pH 8.0, 10. % glycerol, 6 M Urea), A15 (buffer A10 with 15 mM imidazole), A20 (buffer A10 with 20 mM imidazole), A25 (buffer A10 with 25 mM imidazole), and A30 (same as buffer A10 but with 30 mM imidazole). The isolated EPP2 protein is eluted with denaturing elution buffer (250 mM imidazole, 1 M NaCl, 20 mM Tris-HCl, pH 7.5, 10% glycerol, 6 M Urea). Protease inhibitor cocktail was added to the pooled elution fractions and EPP2 protein is dialyzed against 0.2 M bicarbonate buffer with 0.5 M NaCl and cysteine/cystine to remove the urea. After dialysis the samples are concentrated if needed on Aquacide and the protein concentration measured by BCA assay (Pierce; Rockford, Ill.) using a BSA standard curve. The isolated EPP2 protein samples are analyzed upon SDS PAGE followed by Coomassie and Western blotting as shown in FIG. 12. Protein samples are stored at −20° C. with 30% glycerol. Such isolated EPP2 protein preparations are divided into aliquots and stored at −20° C. with 30% glycerol.

Example 6

Antibody Development

Monoclonal antibodies to the ME-5 protein were produced using standard methods (G. Galfre et al. [1977] Nature 266: 550) with modifications (V. T. Oi and L. A. Herzenberg [1980] In B. B. Mishell and S. M. Shiigi [eds.] Selected Method in Cellular Immunology [San Francisco: W.H. Freeman]). Such monoclonal antibody reagents are valuable for additional studies of the ME-5 protein character, and to assist in development of immunoassays for determining the clinical significance of the protein in endometriosis patients. Mice (BALB/c) were immunized with isolated recombinant ME-5 antigen and the antibody response to the antigen monitored in these animals by ELISA and Western blot techniques with the animal's serum. When the antibody response was significant the animals were boosted with another immunization with the ME-5 antigen. Three days later the spleen was removed from an animal and the immune-cells isolated from the organ. The isolated spleen cells were fused with the immunoglobulin non-producing Sp2/0 mouse myeloma cell line (M. Shulman et al. [1978] Nature 276:269). The resulting hybridoma cells were selected in culture medium containing HAT reagents. Candidate hybridoma cells were cloned a minimum of two times by limiting dilution and the clones screened by ELISA using isolated ME-5 antigen. One hybridoma cell line designated 2D1 was found to react particularly well with the isolated ME-5 antigen and this was selected for additional experiments.

Example 7

Identification of Native ME-5 Antigen and Tissue Distribution

Initially the 2D1 monoclonal was used in Western blotting experiments upon protein extracts obtained from cultured RL95-2 endometrial carcinoma cells. Cultured RL95-2 cells were lysed by sonication, and insoluble debris removed by centrifugation. A portion of the soluble fraction was analyzed on SDS PAGE gels adjacent to a sample of isolated recombinant ME-5 protein. FIG. 13 shows the pattern of Western blot analysis obtained with the anti-ME-5 2D1 monoclonal antibody. The monoclonal reacted well with the isolated recombinant antigen and 2D1 reactivity was seen at an estimated molecular weight of 38 kD. In the RL95-2 protein extract there was a clear band of reactivity with the natural ME-5 protein that appeared to be slightly larger than the isolated recombinant.

These studies of the natural ME-5 antigen were expanded to include tissue extracts obtained from various human organs. In these Western blotting experiments various tissues were studied including human spleen, brain, lung, heart, liver, ovary, placenta, testis, skeletal muscle, and kidney. Samples of commercially available human tissue protein extracts (Protein Medleys: BD Biosciences; San Diego, Calif.) were separated by electrophoresis on SDS PAGE gels using instructions provided by the manufacturer. The protein extracts were evaluated by Western blot using the anti-ME-5 2D1 monoclonal as primary antibody and the immune complexes were detected with a $^{125}$I-labeled anti-mouse antibody. The results are shown in FIG. 14 and there was a strong band of reactivity with the isolated recombinant ME-5 protein included as a control. In addition, natural ME-5 protein seems to be present in nearly all of the tissues examined, and appropriately the protein seems to be present at the highest concentrations in ovary tissue. The presence of the ME-5 protein in other reproductive tissue is taken to imply that the antigen may naturally be expressed at high levels in this class of organs. It is therefore likely that ME-5 may have a major role in regulation of functions occurring in the reproductive system. Consequently ME-5 would be more likely to be the target of anti-endometrial antibodies generated during endometriosis. Good levels of expression were also registered in heart, liver, and kidney tissue extracts. This is also encouraging because the CHIP protein discussed in Example 2 was isolated from a cardiac cDNA library. Somewhat lower, but detectable levels of natural ME-5 were found in most of the remaining tissue extracts.

Example 8

Clinical Findings: Reactivity of the ME-5, ME-2, and EPP2 Antigens with Endometriosis Patient Sera The clinical significance of the ME-5, ME-2 and EPP2 proteins were evaluated using line immunoblotting studies to measure reactivity with antibodies present in the serum of endometriosis patients. These line blotting experiments were designed to identify IgG antibodies in human serum reactive with the recombinant proteins. Briefly, the line blot utilizes the ME-5, ME-2, and EPP2 recombinant protein antigens which are immobilized on a nitrocellulose membrane in a discrete location and in the form of a line spanning the surface. In addition, a reagent control line is included to verify that the specific assay conditions have been followed. After cutting the membrane into a number of individual strips these are incubated with individual patient serum, and patient IgG binds to antigens immobilized in the discrete lines. Immune complexes are visualized by incubating the strips with enzyme-labeled anti-human IgG antibodies and a subsequent substrate reaction. When evaluating these experiments, the strips treated with control sera were compared to the strips incubated with endometriosis patient sera to facilitate analysis of the intensity of staining of each band. The patient serum specimen showing reactivity with the ME-5, ME-2, and EPP2 antigens is considered positive if the intensity of the signal is stronger than that obtained with the protein on the control patient strips.

Some representative lineblot strips containing ME-5 antigen treated with normal control patient serum are shown in FIG. 15A. In contrast, the pattern of reactivity of representative endometriosis patients with similar strips is shown in FIG. 15B. Sera from endometriosis patients consistently react much more strongly with the ME-5 protein when compared to control sera (compare patterns of 15A and 15B). Generally a particular concentration of the ME-5 recombinant is signaled out which offers the best discrimination of reactivity for antibodies in endometriosis patients relative to controls. In these experiments, and others to be summarized later, this concentration was 0.036 milligrams of ME-5 per milliliter. At this value, few if any control patients react, but reactivity of the endometriosis patients was substantial.

In this experiment a total of 47 endometriosis patients sera (Diagnostic Support; Boston, Mass.) were evaluated along with 24 negative controls. Some representative data are shown in the figures discussed above, and the reactivity of all the endometriosis patient sera with the recombinant ME-5 antigen is summarized in Table 1. The control reactivity is presented in Table 2. A total of 27 of the endometriosis patients were strongly positive in this experiment. Moreover, most of those patient sera that seemed to be below the 0.036 milligrams of ME-5 per milliliter cut off definitely reacted better with higher concentrations of antigen compared to the negative control sera as noted above. None of the control specimens had had very much antibody reactivity to the ME-5 antigen as measured by line blot. Therefore, the marker ME-5 reacted with at least 57% of the endometriosis patient sera evaluated in this experiment, and overall the pattern of reactivity of sera from endometriosis patients was considerably stronger with the ME-5 protein when compared to the patterns observed with control sera.

Some representative lineblot strips containing the ME-2 antigen and treated with normal control patient serum are shown in FIG. 16A. In contrast, the pattern of reactivity of representative endometriosis patients with similar strips is shown in FIG. 16B. Sera from endometriosis patients consistently react much more strongly with the ME-2 protein when compared to control sera (compare patterns of 16A and 16B). Generally a particular concentration of the ME-2 recombinant is signaled out which offers the best discrimination of reactivity for antibodies in endometriosis patients relative to controls. In these experiments, and others to be summarized later, this concentration was 0.018 milligrams of ME-2 per milliliter. At this value, few if any control patients react, but reactivity of the endometriosis patients was substantial.

In this experiment a total of 47 endometriosis patients sera (Diagnostic Support; Boston, Mass.) were evaluated for reactivity with the ME-2 antigen along with 24 negative controls. Some representative data are shown in the figures discussed above, and the reactivity of all the endometriosis patient sera with the recombinant ME-2 antigen is summarized in Table 3. The control patient reactivity is presented in Table 4. A total of 25 of the endometriosis patients were strongly positive in this experiment. Moreover, most of those patient sera that seemed to be below the 0.018 milligrams of ME-2 per milliliter cut off definitely reacted better with higher concentrations of antigen compared to the negative control sera as noted above. None of the control specimens had very much antibody reactivity to the ME-2 antigen as measured by line blot. Therefore, the marker ME-2 reacted with at least 53% of the endometriosis patient sera evaluated in this experiment, and overall the pattern of reactivity of sera from endometriosis patients was considerably stronger with the ME-2 protein when compared to the patterns observed with control sera. This is further exemplified by the fact that a two-fold higher concentration (0.144 mg/ml) of the ME-2 antigen was evaluated for reactivity with control sera, and the signal intensity observed for this was considerably lower than that generated with endometriosis sera at lower protein levels.

As noted for the activities described above, the patient serum specimen showing reactivity with EPP2 antigen is considered positive if the intensity of the signal is stronger than that obtained with the protein on the control patient strips. Also noted above is that when evaluating these experiments, the strips treated with control sera were compared to the strips incubated with endometriosis patient sera to facilitate analysis of the intensity of staining of each band. Some representative lineblot strips showing the reactivity of recombinant EPP2 with normal control patient serum are shown in FIG. 17A. In contrast, the pattern of reactivity of representative endometriosis patients with similar strips is shown in FIG. 17B. Generally sera from endometriosis patients react much more strongly with the EPP2 protein when compared to control sera (compare patterns of 17A and 17B). Generally a particular concentration of the EPP2 recombinant is signaled out which offers the best discrimination of reactivity for antibodies in endometriosis patients relative to controls. In these experiments, and others to be summarized later, this concentration was 0.05 milligrams of EPP2 per milliliter. At this value, few if any control patients react, but reactivity of the endometriosis patients was substantial.

In this experiment a total of 90 endometriosis patients sera (Diagnostic Support; Boston, Mass. and Boston Biomedica; Boston) were evaluated along with 24 negative controls. Some representative data are shown in the figures discussed above, and the reactivity of all endometriosis patient sera with the recombinant EPP2 antigen is summarized in Table 5. The control patient reactivity presented in Table 6. A total of 55 of the endometriosis patients were strongly positive in this experiment. Moreover, most of those patient sera that seemed to be below the 0.05 milligrams of EPP2 per milliliter cut off definitely reacted better with higher concentrations of antigen compared to the negative control sera as noted above. None of the control specimens had very much antibody reactivity to the EPP2 antigen as measured by line blot. Therefore, the marker EPP2 reacted with at least 61% of the endometriosis patient sera evaluated in this experiment, and overall the pattern of reactivity of sera from endometriosis patients was considerably stronger with the EPP2 protein when compared to the patterns observed with control sera.

Overall the pattern of reactivity for the individual ME-5, ME-2, and EPP2 antigens was between 53% and 61% and this seems sufficient to be useful as a diagnostic marker for endometriosis. However, upon examination of the results summarized in Tables 1, 3, and 5 it is clear that different endometriosis patients do not react in the same way with each of the 3 antigens. Therefore, if the pattern of reactivity of endometriosis patient serum is considered for each of the 3 antigens then this panel of markers makes the utility as a diagnostic test even more convincing. For example, 47 patients were evaluated with each of the ME-5, ME-2, and EPP2 antigens and the pattern of reactivity with antibodies in one or more specimens is summarized in Table 7. Taken together, more that 83% of the sera tested contain antibodies which react with at least one of the ME-5, ME-2, or EPP2 antigens. Consequently if the three antigens were to be considered together as a panel for diagnostic testing then the frequency of antibodies in endometriosis patients that react with them is considerable.

TABLE 1

Overall pattern of ME-5 reactivity with 47 endometriosis patients.

| Serum | ME-5 Rxn. |
|---|---|
| DS01 | + |
| DS02 | − |
| DS03 | + |
| DS04 | − |
| DS05 | + |
| DS06 | + |
| DS07 | − |
| DS08 | − |
| DS09 | + |
| DS10 | + |
| DS11 | + |
| DS12 | + |
| DS13 | − |
| DS14 | + |
| DS15 | − |
| DS16 | + |
| DS17 | + |
| DS18 | − |
| DS19 | − |
| DS20 | − |
| DS21 | − |
| DS25 | − |
| DS26 | − |
| DS27 | + |
| DS28 | + |
| DS29 | + |
| DS30 | + |
| DS31 | + |
| DS32 | + |
| DS33 | + |
| DS34 | + |
| DS35 | − |
| DS36 | + |
| DS37 | − |
| DS38 | + |
| DS39 | + |
| DS40 | + |
| DS41 | − |
| DS42 | + |
| DS43 | + |
| DS44 | + |
| DS45 | + |
| DS46 | − |
| DS47 | − |
| DS48 | − |
| DS49 | − |
| DS50 | − |

Endometriosis patient serum specimens were obtained from a commercial supplier (Diagnostic Support; Boston, MA) and evaluated for reactivity with recombinant ME-5 antigen by line blot.

TABLE 2

Overall pattern of ME-5 reactivity with 24 control patient sera.

| Serum | ME-5 Rxn. |
|---|---|
| A1 | − |
| A2 | − |
| A3 | ± |
| A4 | − |

TABLE 2-continued

Overall pattern of ME-5 reactivity with 24 control patient sera.

| Serum | ME-5 Rxn. |
|---|---|
| A5 | − |
| A6 | − |
| A7 | − |
| A8 | − |
| A9 | ± |
| A10 | − |
| A11 | − |
| A12 | ± |
| A13 | ± |
| A14 | ± |
| A15 | − |
| A16 | − |
| A17 | − |
| A18 | − |
| A19 | − |
| A20 | ± |
| A21 | − |
| A22 | ± |
| A23 | ± |
| A24 | − |

Control patient serum specimens were obtained from an internal blood draw and evaluated for reactivity with recombinant ME-5 antigen by line blot.

TABLE 3

Overall pattern of ME-2 reactivity with 47 endometriosis patients.

| Serum | ME-2 Rxn. |
|---|---|
| DS01 | − |
| DS02 | − |
| DS03 | − |
| DS04 | − |
| DS0S | − |
| DS06 | + |
| DS07 | − |
| DS08 | − |
| DS09 | − |
| DS10 | − |
| DS11 | − |
| DS12 | + |
| DS13 | − |
| DS14 | − |
| DS15 | − |
| DS16 | − |
| DS17 | + |
| DS18 | − |
| DS19 | + |
| DS20 | + |
| DS21 | + |
| DS25 | + |
| DS26 | + |
| DS27 | + |
| DS28 | + |
| DS29 | − |
| DS30 | + |
| DS31 | + |
| DS32 | − |
| DS33 | + |
| DS34 | − |
| DS35 | + |
| DS36 | + |
| DS37 | − |
| DS38 | + |
| DS39 | + |
| DS40 | + |
| DS41 | − |
| DS42 | + |
| DS43 | + |
| DS44 | + |
| DS45 | + |
| DS46 | + |
| DS47 | − |
| DS48 | − |

TABLE 3-continued

Overall pattern of ME-2 reactivity with 47 endometriosis patients.

| Serum | ME-2 Rxn. |
|---|---|
| DS49 | + |
| DS50 | + |

Endometriosis patient serum specimens were obtained from a commercial supplier (Diagnostic Support; Boston, MA) and evaluated for reactivity with recombinant ME-2 antigen by line blot.

TABLE 4

Overall pattern of ME-2 reactivity with 24 control patient sera.

| Serum | ME-2 Rxn. |
|---|---|
| A1 | − |
| A2 | − |
| A3 | − |
| A4 | ± |
| A5 | − |
| A6 | − |
| A7 | − |
| A8 | − |
| A9 | ± |
| A10 | − |
| A11 | − |
| A12 | − |
| A13 | − |
| A14 | ± |
| A15 | − |
| A16 | − |
| A17 | − |
| A18 | ± |
| A19 | − |
| A20 | ± |
| A21 | − |
| A22 | − |
| A23 | − |
| A24 | − |

Control patient serum specimens were obtained from an internal blood draw and evaluated for reactivity with recombinant ME-2 antigen by line blot.

TABLE 5

Overall pattern of EPP2 reactivity with 90 endometriosis patients.

| Serum | EPP2 Rxn. |
|---|---|
| DS01 | − |
| DS02 | − |
| DS03 | + |
| DS04 | − |
| DS05 | + |
| DS06 | + |
| DS07 | − |
| DS08 | − |
| DS09 | − |
| DS10 | − |
| DS11 | − |
| DS12 | + |
| DS13 | − |
| DS14 | − |
| DS15 | + |
| DS16 | − |
| DS17 | − |
| DS18 | − |
| DS19 | + |
| DS20 | + |
| DS21 | + |
| DS22 | + |
| DS23 | − |
| DS24 | + |
| DS25 | − |
| DS26 | − |
| DS27 | + |

TABLE 5-continued

Overall pattern of EPP2 reactivity with 90 endometriosis patients.

| Serum | EPP2 Rxn. |
|---|---|
| DS28 | + |
| DS29 | + |
| DS30 | + |
| DS31 | + |
| DS32 | + |
| DS33 | + |
| DS34 | − |
| DS35 | + |
| DS36 | − |
| DS37 | − |
| DS38 | − |
| DS39 | − |
| DS40 | + |
| DS41 | − |
| DS42 | + |
| DS43 | + |
| DS44 | + |
| DS45 | + |
| DS46 | + |
| DS47 | + |
| DS48 | + |
| DS49 | − |
| DS50 | − |
| BBI01 | − |
| BBI02 | + |
| BBI03 | + |
| BBI04 | + |
| BBI05 | − |
| BBI06 | + |
| BBI07 | + |
| BBI08 | + |
| BBI09 | + |
| BBI10 | + |
| BBI11 | + |
| BBI12 | + |
| BBI13 | + |
| BBI14 | − |
| BBI15 | + |
| BBI16 | + |
| BBI17 | − |
| BBI18 | − |
| BBI19 | − |
| BBI20 | + |
| BBI21 | − |
| BBI22 | + |
| BBI23 | + |
| BBI24 | − |
| BBI25 | + |
| BBI26 | + |
| BBI27 | + |
| BBI28 | + |
| BBI29 | − |
| BBI30 | + |
| BBI31 | + |
| BBI32 | + |
| BBI33 | − |
| BBI34 | + |
| BBI35 | + |
| BBI36 | − |
| BBI37 | + |
| BBI38 | + |
| BBI39 | + |
| BBI40 | + |

Endometriosis patient serum specimens were obtained from a commercial supplier (Diagnostic Support; Boston, MA) and evaluated for reactivity with recombinant EPP2 antigen by line blot.

TABLE 6

Overall pattern of EPP2 reactivity with 24 control patient sera.

| Serum | EPP2 Rxn. |
|---|---|
| A1 | − |
| A2 | − |
| A3 | − |
| A4 | − |
| A5 | − |
| A6 | − |
| A7 | − |
| A8 | − |
| A9 | ± |
| A10 | − |
| A11 | − |
| A12 | − |
| A13 | − |
| A14 | − |
| A15 | − |
| A16 | − |
| A17 | − |
| A18 | − |
| A19 | − |
| A20 | ± |
| A21 | − |
| A22 | − |
| A23 | − |
| A24 | ± |

Control patient serum specimens were obtained from an internal blood draw and evaluated for reactivity with recombinant EPP2 antigen by line blot.

TABLE 7

Summary of the combined pattern of the panel of ME-5, ME-2, or EPP2 reactivity with 47 endometriosis patients.

| Serum | Panel Reactivity |
|---|---|
| DS01 | + |
| DS02 | − |
| DS03 | + |
| DS04 | − |
| DS05 | + |
| DS06 | + |
| DS07 | − |
| DS08 | − |
| DS09 | + |
| DS10 | + |
| DS11 | + |
| DS12 | + |
| DS13 | − |
| DS14 | + |
| DS15 | + |
| DS16 | + |
| DS17 | + |
| DS18 | − |
| DS19 | + |
| DS20 | + |
| DS21 | + |
| DS25 | + |
| DS26 | + |
| DS27 | + |
| DS28 | + |
| DS29 | + |
| DS30 | + |
| DS31 | + |
| DS32 | + |
| DS33 | + |
| DS34 | + |
| DS35 | + |
| DS36 | + |
| DS37 | − |
| DS38 | + |
| DS39 | + |
| DS40 | + |
| DS41 | − |
| DS42 | + |
| DS43 | + |
| DS44 | + |

TABLE 7-continued

Summary of the combined pattern of the panel of ME-5, ME-2, or EPP2 reactivity with 47 endometriosis patients.

| Serum | Panel Reactivity |
|---|---|
| DS45 | + |
| DS46 | − |
| DS47 | + |
| DS48 | + |
| DS49 | + |
| DS50 | + |

A total of 47 endometriosis patient serum specimens were evaluated for reactivity with each of the three antigens as shown in tables 1, 3, and 5. The overall reactivity of each of these patients with one or more of the markers is summarized.

The invention claimed is:

1. A method for diagnosing endometriosis in a human subject comprising the steps of:
   (a) detecting a test amount of an antibody that specifically binds to SEQ ID NO:6 polypeptide or a truncated peptide comprising an epitope of SEQ ID NO: 6, in a sample from the subject; and
   (b) comparing the test amount with a normal range of the antibody in a control, sample from a subject who does not suffer from endometriosis, whereby a test amount above the normal range provides a positive indication in the diagnosis of endometriosis.

2. The method of claim 1, wherein the sample comprises blood serum.

3. The method of claim 1 or 2, wherein the step of detecting comprises capturing the antibody from the sample with an immobilized peptide where said peptide is SEQ ID NO: 6 or a peptide comprising an epitope of SEQ ID NO: 6 and detecting captured antibody.

4. The method of claim 1 wherein said polypeptide has amino acid sequences identical to SEQ ID NO: 6.

5. The method of claim 1 wherein said peptide is a truncated peptide comprising an epitope of SEQ ID NO: 6.

6. The method of claim 1 wherein said SEQ ID NO: 6 polypeptide is produced by recombinant means.

7. The method of claim 1 wherein said truncated peptide of SEQ ID NO: 6 is produced by recombinant means.

* * * * *

SEQUENCE LISTING

<160> NUMBER OF SEQ ID NOS: 9

<210> SEQ ID NO 1
<211> LENGTH: 1302
<212> TYPE: DNA
<213> ORGANISM: Homo sapiens

<400> SEQUENCE: 1

```
ccgggaatga agggccaagg atcgcgggct cgggctgcgg ggctccggct gcgggcgctg      60
ggccgcgagg cgcggagctt gggagcggag cccaggccgt gccgcgcggc gcatgaaggg     120
caaggaggag aaggagggcg gcgcacggct gggcgctggc ggcggaagcc ccgagaagag     180
cccgagcgcg caggagctca aggagcaggg caatcgtctg ttcgtgggcc gaaagtaccc     240
ggaggcggcg gcctgctacg gccgcgcgat caccccggaac ccgctggtgg ccgtgtatta     300
caccaaccgg gccttgtgct acctgaagat gcagcagcac gagcaggccc tggccgactg     360
ccggcgcgcc ctggagctgg acgggcagtc tgtgaaggcg cacttcttcc tggggcagtg     420
ccagctggag atggagagct atgatgaggc catcgccaat ctgcagcgag cttacagcct     480
ggccaaggag cagcggctga acttcgggga cgacatcccc agcgctcttc gaatcgcgaa     540
gaagaagcgc tggaacagca ttgaggagcg gcgcatccac caggagagcg agctgcactc     600
ctacctctcc aggctcattg ccgcggagcg tgagagggag ctggaagagt gccagcgaaa     660
ccacgagggt gatgaggacg acagccacgt ccgggcccag caggcctgca ttgaggccaa     720
gcacgacaag tacatggcgg acatggacga gcttttttct caggtggatg agaagaggaa     780
gaagcgagac atccccgact acctgtgtgg caagatcagc tttgagctga tgcgggagcc     840
gtgcatcacg cccagtggca tcacctacga ccgcaaggac atcgaggagc acctgcagcg     900
tgtgggtcat tttgaccccg tgaccggag cccctgacc caggaacagc tcatcccaa      960
cttggctatg aaggaggtta ttgacgcatt catctctgag aatggctggg tggaggacta    1020
ctgaggttcc ctgccctacc tggcgtcctg gtccagggga gccctgggca gaagcccccg    1080
gcccctatac atagtttatg ttcctggcca ccccgaccgc ttcccccaag ttctgctgtt    1140
ggactctgga ctgtttcccc tctcagcatc gcttttgctg ggccgtgatc gtccccttt     1200
gtgggctgga aaagcaggtg agggtgggct gggctgaggc cattgccgcc actatctgtg    1260
taataaaatc cgtgagcacg aaaaaaaaaa aaaaaaaaa aa                         1302
```

<210> SEQ ID NO 2
<211> LENGTH: 912
<212> TYPE: DNA
<213> ORGANISM: Homo sapiens

<400> SEQUENCE: 2

```
atgaaggcca aggaggagaa ggagggcggc gcacggctgg gcgctggcgg cggaagcccc      60
gagaagagcc cgagcgcgca ggagctcaag gagcagggca atcgtctgtt cgtgggccga     120
aagtacccgg aggcggcggc ctgctacggc cgcgcgatca cccggaaccc gctggtggcc     180
gtgtattaca ccaaccgggc cttgtgctac ctgaagatgc agcagcacga gcaggccctg     240
gccgactgcc ggcgcgccct ggagctggac gggcagtctg tgaaggcgca cttcttcctg     300 ggcagtgcc agctggagat ggagagctat gatgaggcca tcgccaatct gcagcgagct     360
tacagcctgg ccaaggagca gcggctgaac ttcggggacg acatccccag cgctcttcga     420
atcgcgaaga gaagcgctg gaacagcatt gaggagcggc gcatccacca ggagagcgag     480
ctgcactcct acctctccag gctcattgcc gcggagcgtg agggagct ggaagagtgc     540 cagcgaaacc acgagggtga tgaggacgac agccacgtcc gggcccagca ggcctgcatt     600
gaggccaagc acgacaagta catggcggac atggacgagc tttttttctca ggtggatgag     660 aagaggaaga agcgagacat ccccgactac ctgtgtggca agatcagctt tgagctgatg     720
cgggagccgt gcatcacgcc cagtggcatc acctacgacc gcaaggacat cgaggagcac     780
ctgcagcgtg tgggtcattt tgaccccgtg acccggagcc ccctgaccca ggaacagctc     840
atccccaact tggctatgaa ggaggttatt gacgcattca tctctgagaa tggctgggtg     900
gaggactact ga                                                         912
```

<210> SEQ ID NO 3
<211> LENGTH: 303
<212> TYPE: PRT
<213> ORGANISM: Homo sapiens
<400> SEQUENCE: 3

```
Met Lys Gly Lys Glu Glu Lys Glu Gly Gly Ala Arg Leu Gly Ala Gly
  1               5                  10                  15

Gly Gly Ser Pro Glu Lys Ser Pro Ser Ala Gln Glu Leu Lys Glu Gln
             20                  25                  30

Gly Asn Arg Leu Phe Val Gly Arg Lys Tyr Pro Glu Ala Ala Ala Cys
         35                  40                  45

Tyr Gly Arg Ala Ile Thr Arg Asn Pro Leu Val Ala Val Tyr Tyr Thr
     50                  55                  60

Asn Arg Ala Leu Cys Tyr Leu Lys Met Gln Gln His Glu Gln Ala Leu
 65                  70                  75                  80

Ala Asp Cys Arg Arg Ala Leu Glu Leu Asp Gly Gln Ser Val Lys Ala
                 85                  90                  95

His Phe Phe Leu Gly Gln Cys Gln Leu Glu Met Glu Ser Tyr Asp Glu
            100                 105                 110

Ala Ile Ala Asn Leu Gln Arg Ala Tyr Ser Leu Ala Lys Glu Gln Arg
        115                 120                 125

Leu Asn Phe Gly Asp Asp Ile Pro Ser Ala Leu Arg Ile Ala Lys Lys
    130                 135                 140

Lys Arg Trp Asn Ser Ile Glu Glu Arg Arg Ile His Gln Glu Ser Glu
145                 150                 155                 160

Leu His Ser Tyr Leu Ser Arg Leu Ile Ala Ala Glu Arg Glu Arg Glu
                165                 170                 175

Leu Glu Glu Cys Gln Arg Asn His Glu Gly Asp Glu Asp Ser His
            180                 185                 190

Val Arg Ala Gln Gln Ala Cys Ile Glu Ala Lys His Asp Lys Tyr Met
        195                 200                 205

Ala Asp Met Asp Glu Leu Phe Ser Gln Val Asp Glu Lys Arg Lys Lys
```

```
                210                 215                 220
Arg Asp Ile Pro Asp Tyr Leu Cys Gly Lys Ile Ser Phe Glu Leu Met
225                 230                 235                 240

Arg Glu Pro Cys Ile Thr Pro Ser Gly Ile Thr Tyr Asp Arg Lys Asp
                245                 250                 255

Ile Glu Glu His Leu Gln Arg Val Gly His Phe Asp Pro Val Thr Arg
                260                 265                 270

Ser Pro Leu Thr Gln Glu Gln Leu Ile Pro Asn Leu Ala Met Lys Glu
                275                 280                 285

Val Ile Asp Ala Phe Ile Ser Glu Asn Gly Trp Val Glu Asp Tyr
                290                 295                 300

<210> SEQ ID NO 4
<211> LENGTH: 1353
<212> TYPE: DNA
<213> ORGANISM: Homo sapiens

<400> SEQUENCE: 4
ctgacatgca gccctctgga ccccgaggtt ggaccctact gtgacacacc taccatgcgg      60
acactcttca acctcctctg gcttgccctg gcctgcagcc ctgttcacac taccctgtca     120
aagtcagatg ccaaaaaagc cgcctcaaag acgctgctgg agaagagtca gttttcagat     180
aagccggtgc aagaccgggg tttggtggtg acggacctca agctgagagt gtggttctt      240 gagcatcgca gctactgctc ggcaaaggcc cggacagac actttgctgg ggatgtactg      300
ggctatgtca ctccatggaa cagccatggc tacgatgtca ccaaggtctt tgggagcaag     360
ttcacacaga tctcacccgt ctggctgcag ctgaagagac gtggccgtga tgtgtttgag     420
gtcacgggcc tccacgacgt ggaccaaggg tggatgcgag ctgtcaggaa gcatgccaag     480
ggcctgcaca tagtgcctcg gctcctgttt gaggactgga cttacgatga tttccggaac     540
gtcttagaca gtgaggatga tagaggag ctgagcaaga ccgtggtcca ggtggcaaag     600
aaccagcatt cgacggcttt cgtggtggag gtctggaacc agctgctaag ccagaagcgc     660
gtgggcctca tccacatgct cacccacttg gccgaggctc tgcaccaggc ccggctgctg     720
gccctcctgg tcatcccgcc tgccatcacc cccgggaccg accagctggg catgttcacg     780
cacaaggagt ttgagcagct ggcccccgtg ctggatggtt tcagcctcat gacctacgac     840
tactctacag cgcatcagcc tggccctaat gcacccctgt cctgggttcg agcctgcgtc     900
caggtcctgg acccgaagtc caagtggcga agcaaaatcc tcctggggct caacttctat     960
ggtatggact acgcgacctc caaggatgcc cgtgagcctg ttgtcggggc caggtacatc    1020
cagacactga aggaccacag gccccggatg tgtgggaca gccaggcctc agagcacttc    1080
ttcgagtaca agaagagccg cagtgggagg cacgtcgtct ctacccaac cctgaagtcc    1140 ctgcaggtgc ggctggagct ggcccggag ctgggcgttg gggtctctat ctgggagctg    1200
ggccagggcc tgaactactt ctacgacctg ctctaggtgg cattgcggc ctccgcggtg    1260 gacgtgttct tttctaatgc catggagtga gtgagcaggt gtgaaataca ggcctccact    1320
ccgtttgctg tgaaaaaaaa aaaaaaaaaa aaa                                  1353

<210> SEQ ID NO 5
<211> LENGTH: 1182
<212> TYPE: DNA
<213> ORGANISM: Homo sapiens

<400> SEQUENCE: 5
atgcggacac tcttcaacct cctctggctt gccctggcct gcagccctgt tcacactacc       60
```

-continued

```
ctgtcaaagt cagatgccaa aaaagccgcc tcaaagacgc tgctggagaa gagtcagttt      120
tcagataagc cggtgcaaga ccggggtttg gtggtgacgg acctcaaagc tgagagtgtg      180
gttcttgagc atcgcagcta ctgctcggca aaggcccggg acagacactt tgctggggat      240
gtactgggct atgtcactcc atggaacagc catggctacg atgtcaccaa ggtctttggg      300
agcaagttca cacagatctc acccgtctgg ctgcagctga agagacgtgg ccgtgagatg      360
tttgaggtca cgggcctcca cgacgtggac caagggtgga tgcgagctgt caggaagcat      420
gccaagggcc tgcacatagt gcctcggctc ctgtttgagg actggactta cgatgatttc      480
cggaacgtct tagacagtga ggatgagata gaggagctga gcaagaccgt ggtccaggtg      540
gcaaagaacc agcatttcga cggcttcgtg gtggaggtct ggaaccagct gctaagccag      600
aagcgcgtgg gcctcatcca catgctcacc cacttggccg aggctctgca ccaggcccgg      660
ctgctggccc tcctggtcat cccgcctgcc atcacccccg ggaccgacca gctgggcatg      720
ttcacgcaca aggagtttga gcagctggcc ccgtgctgg atggtttcag cctcatgacc      780
tacgactact ctacagcgca tcagcctggc cctaatgcac ccctgtcctg ggttcgagcc      840
tgcgtccagg tcctggaccc gaagtccaag tggcgaagca aaatcctcct ggggctcaac      900
ttctatggta tggactacgc gacctccaag gatgcccgtg agcctgttgt cggggccagg      960
tacatccaga cactgaagga ccacaggccc cggatggtgt gggacagcca ggcctcagag     1020
cacttcttcg agtacaagaa gagccgcagt gggaggcacg tcgtcttcta cccaaccctg     1080
aagtccctgc aggtgcggct ggagctggcc cgggagctgg gcgttggggt ctctatctgg     1140
gagctgggcc agggcctgaa ctacttctac gacctgctct ag                         1182
```

<210> SEQ ID NO 6
<211> LENGTH: 393
<212> TYPE: PRT
<213> ORGANISM: Homo sapiens

<400> SEQUENCE: 6

```
Met Arg Thr Leu Phe Asn Leu Leu Trp Leu Ala Leu Ala Cys Ser Pro
1               5                   10                  15

Val His Thr Thr Leu Ser Lys Ser Asp Ala Lys Ala Ala Ser Lys
        20                  25                  30

Thr Leu Leu Glu Lys Ser Gln Phe Ser Asp Lys Pro Val Gln Asp Arg
    35                  40                  45

Gly Leu Val Val Thr Asp Leu Lys Ala Glu Ser Val Val Leu Glu His
50                  55                  60

Arg Ser Tyr Cys Ser Ala Lys Ala Arg Asp Arg His Phe Ala Gly Asp
65                  70                  75                  80

Val Leu Gly Tyr Val Thr Pro Trp Asn Ser His Gly Tyr Asp Val Thr
                85                  90                  95

Lys Val Phe Gly Ser Lys Phe Thr Gln Ile Ser Pro Val Trp Leu Gln
            100                 105                 110

Leu Lys Arg Arg Gly Arg Glu Met Phe Glu Val Thr Gly Leu His Asp
        115                 120                 125

Val Asp Gln Gly Trp Met Arg Ala Val Arg Lys His Ala Lys Gly Leu
    130                 135                 140

His Ile Val Pro Arg Leu Leu Phe Glu Asp Trp Thr Tyr Asp Asp Phe
145                 150                 155                 160

Arg Asn Val Leu Asp Ser Glu Asp Glu Ile Glu Glu Leu Ser Lys Thr
                165                 170                 175
```

-continued

```
Val Val Gln Val Ala Lys Asn Gln His Phe Asp Gly Phe Val Val Glu
            180                 185                 190
Val Trp Asn Gln Leu Leu Ser Gln Lys Arg Val Gly Leu Ile His Met
        195                 200                 205
Leu Thr His Leu Ala Glu Ala Leu His Gln Ala Arg Leu Leu Ala Leu
    210                 215                 220
Leu Val Ile Pro Pro Ala Ile Thr Pro Gly Thr Asp Gln Leu Gly Met
225                 230                 235                 240
Phe Thr His Lys Glu Phe Glu Gln Leu Ala Pro Val Leu Asp Gly Phe
                245                 250                 255
Ser Leu Met Thr Tyr Asp Tyr Ser Thr Ala His Gln Pro Gly Pro Asn
            260                 265                 270
Ala Pro Leu Ser Trp Val Arg Ala Cys Val Gln Val Leu Asp Pro Lys
        275                 280                 285
Ser Lys Trp Arg Ser Lys Ile Leu Leu Gly Leu Asn Phe Tyr Gly Met
    290                 295                 300
Asp Tyr Ala Thr Ser Lys Asp Ala Arg Glu Pro Val Val Gly Ala Arg
305                 310                 315                 320
Tyr Ile Gln Thr Leu Lys Asp His Arg Pro Arg Met Val Trp Asp Ser
                325                 330                 335
Gln Ala Ser Glu His Phe Phe Glu Tyr Lys Lys Ser Arg Ser Gly Arg
            340                 345                 350
His Val Val Phe Tyr Pro Thr Leu Lys Ser Leu Gln Val Arg Leu Glu
        355                 360                 365
Leu Ala Arg Glu Leu Gly Val Gly Val Ser Ile Trp Glu Leu Gly Gln
    370                 375                 380
Gly Leu Asn Tyr Phe Tyr Asp Leu Leu
385                 390

<210> SEQ ID NO 7
<211> LENGTH: 891
<212> TYPE: DNA
<213> ORGANISM: Homo sapiens

<400> SEQUENCE: 7
cggaagacga gggcggcgag gtcgggttcc gggcgcttgg agaagatggt gctgcggcgg      60
ctgctggccg ccctgctgca cagcccgcag ctggtggaac gtctgtcaga gtcgcggcct     120
atccgacgtg cggcgcagct cacggccttc gcactgctgc aggcccagct gcggggccag     180
gacgcggccc gccgcctgca ggacctcgcg gctgggcccg tgggctccct gtgccgccgc     240
gctgagcgat ttagagacgc cttcacccag gagctacgcc gcggcctccg aggccgctcg     300
gggccaccac caggtagcca gagggcccct ggcgcaaaca tttaatcctg gctgtgcgg      360
ggccgaagcc gcttgctttt ccttccgggc tctacagtgg catcaatgtg agggggtcat     420
tccgggcact gcgcgcggct tcgaatcccg actgggattg ttggcctgca gacatcccac     480
gcataagagc ctaggccaga ccgcccgctc cgttgaagtc ttgtgattgg acaagacaca     540
gtgtggagaa agacccctaa gcctaacaga gatgaaggta ggctgggtcc agacacggca     600
cctacggaga gccacggacc gaagccagag agcctttcct ctgcaagtgg gactgaaact     660
cttgacagat gctgctcaat ctgactggta tagcaggaca gttaattcca gggacgatat     720
ggatgaaaag acaaccctac agctgccaaa ttcctttgat taaatgtgtg agctggttga     780
taggcatgag tgtgatactt ctcaggcaag atgtgttaag aataccgggg actgtaggcc     840
tatggtaata ataaacacgt attttatgaa aaaaaaaaaa aaaaaaaaaa a              891
```

```
<210> SEQ ID NO 8
<211> LENGTH: 300
<212> TYPE: DNA
<213> ORGANISM: Homo sapiens

<400> SEQUENCE: 8
atggtgctgc ggcggctgct ggccgccctg ctgcacagcc cgcagctggt ggaacgtctg      60
tcagagtcgc ggcctatccg acgtgcggcg cagctcacgg ccttcgcact gctgcaggcc     120
cagctgcggg ccaggacgc ggcccgccgc ctgcaggacc tcgcggctgg gcccgtgggc     180
tccctgtgcc gccgcgctga gcgatttaga gacgccttca cccaggagct acgccgcggc     240
ctccgaggcc gctcggggcc accaccaggt agccagaggg gccctggcgc aaacatttaa     300

<210> SEQ ID NO 9
<211> LENGTH: 99
<212> TYPE: PRT
<213> ORGANISM: Homo sapiens

<400> SEQUENCE: 9

Met Val Leu Arg Arg Leu Leu Ala Ala Leu Leu His Ser Pro Gln Leu
1               5                   10                  15

Val Glu Arg Leu Ser Glu Ser Arg Pro Ile Arg Arg Ala Ala Gln Leu
            20                  25                  30

Thr Ala Phe Ala Leu Leu Gln Ala Gln Leu Arg Gly Gln Asp Ala Ala
        35                  40                  45

Arg Arg Leu Gln Asp Leu Ala Ala Gly Pro Val Gly Ser Leu Cys Arg
    50                  55                  60

Arg Ala Glu Arg Phe Arg Asp Ala Phe Thr Gln Glu Leu Arg Arg Gly
65                  70                  75                  80

Leu Arg Gly Arg Ser Gly Pro Pro Pro Gly Ser Gln Arg Gly Pro Gly
                85                  90                  95

Ala Asn Ile
```